US008821885B2

(12) United States Patent
Fischer et al.

(10) Patent No.: US 8,821,885 B2
(45) Date of Patent: Sep. 2, 2014

(54) IMMUNOGENIC COMPOSITIONS AND METHODS

(75) Inventors: Gerald W. Fischer, Bethesda, MD (US); Luke T. Daum, San Antonio, TX (US)

(73) Assignee: Longhorn Vaccines & Diagnostics, LLC, Bethesda, MD (US)

( * ) Notice: Subject to any disclaimer, the term of this patent is extended or adjusted under 35 U.S.C. 154(b) by 47 days.

(21) Appl. No.: 12/199,729

(22) Filed: Aug. 27, 2008

(65) Prior Publication Data

US 2009/0081202 A1  Mar. 26, 2009

Related U.S. Application Data

(60) Provisional application No. 60/968,145, filed on Aug. 27, 2007.

(51) Int. Cl.
| | | |
|---|---|---|
| *A61K 39/42* | (2006.01) | |
| *C07K 16/10* | (2006.01) | |
| *C07H 21/04* | (2006.01) | |
| *A61K 39/145* | (2006.01) | |
| *A61P 31/16* | (2006.01) | |
| *A61P 37/00* | (2006.01) | |
| *C12N 5/10* | (2006.01) | |
| *C12N 15/63* | (2006.01) | |
| *C12N 7/01* | (2006.01) | |
| *A61K 39/09* | (2006.01) | |
| *A61K 39/085* | (2006.01) | |
| *C07K 14/005* | (2006.01) | |
| *A61K 39/102* | (2006.01) | |
| *A61K 39/12* | (2006.01) | |
| *A61K 39/00* | (2006.01) | |

(52) U.S. Cl.
CPC ......... *A61K 39/085* (2013.01); *A61K 2039/543* (2013.01); *A61K 39/092* (2013.01); *A61K 2039/5252* (2013.01); *A61K 2039/70* (2013.01); *C12N 2760/16122* (2013.01); *A61K 2039/545* (2013.01); *A61K 2039/6037* (2013.01); *C07K 14/005* (2013.01); *A61K 39/102* (2013.01); *A61K 39/12* (2013.01); *A61K 39/145* (2013.01); *C12N 2760/16134* (2013.01)
USPC .............. 424/185.1; 424/184.1; 424/192.1; 424/201.1; 424/202.1; 424/278.1; 424/130.1; 435/235.1; 435/320.1; 435/325; 530/387.1; 536/23.1

(58) Field of Classification Search
CPC ............... G01N 33/56983; A61K 2039/6075; A61K 2039/70; A61K 39/295; C07K 2319/00; C07K 14/005; C07K 14/11; C12N 2760/16134
USPC .............. 424/130.1, 184.1; 435/235.1, 320.1, 435/325; 530/387.1, 389.4; 536/23.1
See application file for complete search history.

(56) References Cited

U.S. PATENT DOCUMENTS

| | | |
|---|---|---|
| 4,116,777 A | 9/1978 | Takatsy et al. |
| 4,315,073 A | 2/1982 | Brown et al. |
| 4,355,102 A | 10/1982 | Quash |
| 4,356,170 A | 10/1982 | Jennings et al. |
| 4,372,945 A | 2/1983 | Likhite |
| 4,474,757 A | 10/1984 | Arnon et al. |
| 4,578,770 A | 3/1986 | Mitani |
| 4,588,680 A | 5/1986 | Bucher et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,668,476 A | 5/1987 | Bridgham et al. |
| 4,746,490 A | 5/1988 | Saneii |
| 4,816,513 A | 3/1989 | Bridgham et al. |
| 4,981,782 A | 1/1991 | Judd et al. |
| 5,136,019 A | 8/1992 | Judd et al. |
| 5,168,039 A | 12/1992 | Crawford et al. |
| 5,186,898 A | 2/1993 | Bridgham et al. |
| 5,187,060 A | 2/1993 | Cerutti et al. |
| 5,243,030 A | 9/1993 | Judd et al. |
| 5,252,458 A | 10/1993 | Liav et al. |
| 5,290,686 A | 3/1994 | Kendal et al. |
| 5,316,910 A | 5/1994 | Rota et al. |
| 5,589,174 A | 12/1996 | Okuno et al. |
| 5,612,037 A * | 3/1997 | Huebner et al. ........... 424/194.1 |
| 5,631,350 A | 5/1997 | Okuno et al. |
| 5,663,055 A | 9/1997 | Turner et al. |
| 5,719,020 A | 2/1998 | Liav et al. |
| 5,736,333 A | 4/1998 | Livak et al. |

(Continued)

FOREIGN PATENT DOCUMENTS

| | | |
|---|---|---|
| EP | 0313224 | 4/1989 |
| EP | 0621339 | 10/1994 |

(Continued)

OTHER PUBLICATIONS

Lederman et al. Molecular Immunology 1991, vol. 28, No. 11, pp. 1171-1181.*

(Continued)

*Primary Examiner* — Benjamin P Blumel
*Assistant Examiner* — Rachel Gill
(74) *Attorney, Agent, or Firm* — Remenick PLLC

(57) ABSTRACT

The invention is directed to immunogenic compositions, and methods for their use in the formulation and administration of therapeutic and prophylactic pharmaceutical agents. In particular, the invention provides immunogenic compositions and methods for preventing, treating, and/or ameliorating microbial infection, including, for example, influenza, or one or more symptoms thereof.

33 Claims, 24 Drawing Sheets

(56) References Cited

U.S. PATENT DOCUMENTS

| | | | |
|---|---|---|---|
| 5,766,841 A | 6/1998 | Liav et al. | |
| 5,945,515 A | 8/1999 | Chomczynski | |
| 5,958,379 A | 9/1999 | Regenold et al. | |
| 6,015,664 A | 1/2000 | Henrickson et al. | |
| 6,136,585 A * | 10/2000 | Ball et al. | 435/236 |
| 6,168,915 B1 | 1/2001 | Scholl et al. | |
| 6,242,582 B1 | 6/2001 | Reece et al. | |
| 6,280,928 B1 | 8/2001 | Scholl et al. | |
| 6,306,582 B1 | 10/2001 | Scholl et al. | |
| 6,376,172 B1 | 4/2002 | Scholl et al. | |
| 6,406,842 B2 | 6/2002 | Scholl et al. | |
| 6,458,577 B1 | 10/2002 | Huang | |
| 6,495,316 B1 | 12/2002 | Scholl et al. | |
| 6,500,432 B1 | 12/2002 | Dalemans et al. | |
| 6,503,745 B1 | 1/2003 | Chand et al. | |
| 6,573,080 B2 | 6/2003 | Scholl et al. | |
| 6,602,510 B1 | 8/2003 | Fikes et al. | |
| 6,603,908 B2 | 8/2003 | Dallas et al. | |
| 6,610,474 B1 | 8/2003 | Huang | |
| 6,627,396 B1 | 9/2003 | Swanson et al. | |
| 6,680,308 B1 | 1/2004 | Hassan | |
| 6,689,363 B1 * | 2/2004 | Sette et al. | 424/189.1 |
| 6,720,409 B2 | 4/2004 | Okuno et al. | |
| 6,734,292 B1 | 5/2004 | Omura et al. | |
| 6,811,971 B2 | 11/2004 | Klepp et al. | |
| 6,855,321 B1 * | 2/2005 | Rappuoli et al. | 424/192.1 |
| 6,875,600 B2 | 4/2005 | Scholl et al. | |
| 6,881,835 B2 | 4/2005 | Bai et al. | |
| 6,893,814 B2 | 5/2005 | Swanson et al. | |
| 6,946,291 B2 | 9/2005 | Scholl et al. | |
| 7,122,640 B2 | 10/2006 | Gjerde et al. | |
| 7,223,409 B2 | 5/2007 | Nagata et al. | |
| 7,351,413 B2 | 4/2008 | Page et al. | |
| 7,361,352 B2 | 4/2008 | Birkett et al. | |
| 7,494,771 B2 | 2/2009 | Picard et al. | |
| 7,718,402 B2 | 5/2010 | Gayral et al. | |
| 7,767,804 B2 | 8/2010 | Bair, Jr. et al. | |
| 8,084,443 B2 | 12/2011 | Fischer et al. | |
| 8,293,467 B2 | 10/2012 | Fischer et al. | |
| 2001/0021501 A1 | 9/2001 | Scholl et al. | |
| 2001/0034022 A1 | 10/2001 | Scholl et al. | |
| 2001/0036628 A1 | 11/2001 | Scholl et al. | |
| 2002/0054882 A1 | 5/2002 | Okuno et al. | |
| 2002/0055094 A1 | 5/2002 | Reece et al. | |
| 2002/0081567 A1 | 6/2002 | Henrickson et al. | |
| 2002/0169140 A1 | 11/2002 | Prendergast | |
| 2003/0054337 A1 * | 3/2003 | Birkett | 435/5 |
| 2003/0119209 A1 | 6/2003 | Kaylor et al. | |
| 2003/0143566 A1 | 7/2003 | Helftenbein | |
| 2003/0203357 A1 | 10/2003 | Huang | |
| 2003/0215796 A1 | 11/2003 | Scholl et al. | |
| 2003/0219442 A1 | 11/2003 | Mikayama et al. | |
| 2004/0009126 A1 | 1/2004 | Pilkiewicz et al. | |
| 2004/0071757 A1 | 4/2004 | Rolf | |
| 2004/0082549 A1 | 4/2004 | Jomaa | |
| 2004/0086849 A1 | 5/2004 | Shimasaki et al. | |
| 2004/0101869 A1 | 5/2004 | Berg et al. | |
| 2004/0126789 A1 | 7/2004 | Park et al. | |
| 2004/0142319 A1 | 7/2004 | Yu et al. | |
| 2004/0170965 A1 | 9/2004 | Scholl et al. | |
| 2004/0214272 A1 * | 10/2004 | La Rosa et al. | 435/69.1 |
| 2004/0223976 A1 * | 11/2004 | Bianchi et al. | 424/186.1 |
| 2005/0009008 A1 | 1/2005 | Robinson et al. | |
| 2005/0042229 A1 | 2/2005 | Yang et al. | |
| 2005/0090009 A1 | 4/2005 | Cormier et al. | |
| 2005/0112656 A1 | 5/2005 | Iwaki | |
| 2005/0169941 A1 | 8/2005 | Lees | |
| 2005/0170334 A1 | 8/2005 | Mikayama et al. | |
| 2005/0181357 A1 | 8/2005 | Peiris et al. | |
| 2005/0187213 A1 | 8/2005 | Lang et al. | |
| 2005/0227269 A1 | 10/2005 | Lloyd et al. | |
| 2006/0014185 A1 | 1/2006 | Ollikka et al. | |
| 2006/0105468 A1 | 5/2006 | Winkler et al. | |
| 2006/0121468 A1 * | 6/2006 | Allnutt et al. | 435/6 |
| 2006/0217338 A1 * | 9/2006 | Lu et al. | 514/44 |
| 2006/0286557 A1 | 12/2006 | Basehore et al. | |
| 2007/0172835 A1 | 7/2007 | McBride et al. | |
| 2007/0196388 A1 | 8/2007 | Dowling et al. | |
| 2007/0202497 A1 | 8/2007 | Renuart et al. | |
| 2007/0202511 A1 | 8/2007 | Chen et al. | |
| 2007/0286871 A1 * | 12/2007 | Hickle et al. | 424/202.1 |
| 2008/0032921 A1 * | 2/2008 | Alexander et al. | 514/2 |
| 2008/0050737 A1 | 2/2008 | Arieli et al. | |
| 2008/0260763 A1 * | 10/2008 | Felgner et al. | 424/186.1 |
| 2009/0092582 A1 * | 4/2009 | Bogin et al. | 424/85.5 |
| 2009/0098527 A1 | 4/2009 | Fischer et al. | |
| 2009/0233309 A1 | 9/2009 | Fischer | |
| 2009/0312285 A1 | 12/2009 | Fischer | |
| 2010/0009343 A1 | 1/2010 | Fischer | |
| 2010/0055672 A1 | 3/2010 | Saghbini | |
| 2010/0151477 A1 | 6/2010 | Cawthon | |
| 2010/0311739 A1 | 12/2010 | Gunaratnan et al. | |
| 2011/0117128 A1 * | 5/2011 | Powell et al. | 424/210.1 |
| 2011/0159497 A1 | 6/2011 | Lee et al. | |
| 2011/0182974 A1 * | 7/2011 | Ben-Yedidia et al. | 424/450 |
| 2012/0014972 A1 * | 1/2012 | Hodges et al. | 424/159.1 |
| 2012/0177701 A1 * | 7/2012 | Ilyinskii et al. | 424/400 |
| 2012/0244527 A1 | 9/2012 | Trinh et al. | |
| 2013/0039884 A1 * | 2/2013 | Bogin et al. | 424/85.2 |
| 2013/0195909 A1 * | 8/2013 | Fischer et al. | 424/192.1 |

FOREIGN PATENT DOCUMENTS

| | | |
|---|---|---|
| EP | 0675199 | 10/1995 |
| EP | 0726316 | 8/1996 |
| EP | 1081496 | 3/2001 |
| WO | WO 91/02740 | 3/1991 |
| WO | WO9203454 | 3/1992 |
| WO | WO9216619 | 10/1992 |
| WO | WO9409035 | 4/1994 |
| WO | WO9417106 | 8/1994 |
| WO | WO 95/08348 | 3/1995 |
| WO | WO9705248 | 2/1997 |
| WO | WO01/16163 A2 * | 3/2001 |
| WO | WO03026567 | 4/2003 |
| WO | WO 03/053462 | 7/2003 |
| WO | WO03/095646 | 11/2003 |
| WO | WO2004/002451 A2 * | 1/2004 |
| WO | WO2004004658 | 1/2004 |
| WO | WO 2004/043407 | 5/2004 |
| WO | WO2004055205 | 7/2004 |
| WO | WO2004072270 | 8/2004 |
| WO | WO2004084876 | 10/2004 |
| WO | WO 2005010186 | 2/2005 |
| WO | WO 2005/042784 | 5/2005 |
| WO | WO2005075642 | 8/2005 |
| WO | WO2005085274 | 9/2005 |
| WO | WO2006/041933 A2 * | 4/2006 |
| WO | WO 2006/138444 | 12/2006 |
| WO | WO2007051036 | 3/2007 |
| WO | WO 2007/051036 | 5/2007 |
| WO | WO 2007/056266 | 5/2007 |
| WO | WO2007056266 | 5/2007 |
| WO | WO 2007/091030 | 8/2007 |
| WO | WO2007133682 | 11/2007 |
| WO | WO2008079463 | 7/2008 |
| WO | WO2009085355 | 7/2009 |

OTHER PUBLICATIONS

Chien et al. J. Clin. Microbiol. 1999, vol. 37, No. 5, 1393-1397.*
Ishioka GY, Fikes J, Hermanson G, Livingston B, Crimi C, Qin M, del Guercio MF, Oseroff C, Dahlberg C, Alexander J, Chesnut RW, Sette A. Utilization of MHC class I transgenic mice for development of minigene DNA vaccines encoding multiple HLA-restricted CTL epitopes. J Immunol. Apr. 1, 1999;162(7):3915-25.*
Arend et al. Infection and Immunity, 2000, vol. 68, No. 6, pp. 3314-3321.*
De Folette et al. Vaccine Jun. 12, 2006, vol. 24, No. 44-46, pp. 6597-6601.*
Galarza et al. Viral Immunity 2005, vol. 18, No. 2, pp. 365-372.*
Shapira M, Jibson M, Muller G, Arnon R. Immunity and protection against influenza virus by synthetic peptide corresponding to

(56) References Cited

OTHER PUBLICATIONS antigenic sites of hemagglutinin. Proc Natl Acad Sci U S A. Apr. 1984;81(8):2461-5.*
Shah S, Raghupathy R, Singh O, Talwar GP, Sodhi A. Prior immunity to a carrier enhances antibody responses to hCG in recipients of an hCG-carrier conjugate vaccine. Vaccine. Aug. 6, 1999;17(23-24):3116-23. PubMed PMID: 10462248.*
"Influenza: Immunogenicity and Vaccine Efficacy." Centers for Disease Control and Prevention (CDC) Pink Sheet. pp. 151-172. May 7, 2012.*
"Tetanus: Immunogenicity and Vaccine Efficacy." Centers for Disease Control and Prevention (CDC) Pink Sheet. pp. 291-300. May 7, 2012.*
Chamnanpood,P., Chamnanpood,C., Sanguansermsri,P. and Sanguansermsri,D. Characterization of HPAI H5N1 in Thailand: Jul.-Sep. 2004. NCBI GenBank Direct Submission. Apr. 25, 2005. Deposit No. AAY41867.*
Fairweather,N.F., Lyness,V.A., Pickard,D.J., Allen,G, Thomson,R.O. Cloning, nucleotide sequencing, and expression of tetanus toxin fragment C in *Escherichia coli*. NCBI GenBank Dep. No. AAA23282. Apr. 26, 1993.*
Hsu CT, Ting CY, Ting CJ, Chen TY, Lin CP, Whang-Peng J, Hwang J. Vaccination against gonadotropin-releasing hormone (GnRH) using toxin receptor-binding domain-conjugated GnRH repeats. Cancer Res. Jul. 15, 2000;60(14):3701-5.*
Johansson J, Hellman L. Modifications increasing the efficacy of recombinant vaccines; marked increase in antibody titers with moderately repetitive variants of a therapeutic allergy vaccine. Vaccine. Feb. 19, 2007;25(9):1676-82. Epub Nov. 13, 2006.*
Yankai Z, Rong Y, Yi H, Wentao L, Rongyue C, Ming Y, Taiming L, Jingjing L, Jie W. Ten tandem repeats of beta-hCG 109-118 enhance immunogenicity and anti-tumor effects of beta-hCG C-terminal peptide carried by mycobacterial heat-shock protein HSP65. Biochem Biophys Res Commun. Jul. 14, 2006;345(4)1365-71. Epub May 11, 2006.*
Geysen, et al., "Use of Peptide Synthesis to Probe Viral Antigens for Epitopes to a Resolution of a Single Amino Acid," *Proc. Natl. Acad. Sci.*, 81, pp. 3998-4002 (1984).
Valmori, et al., "Use of Human Universally Antigenic Tetanus Toxin T Cell Epitopes as Carriers for Human Vaccination," *J. of Immunol.*, 149(2), pp. 717-721 (1992).
Tolman, et al., "Cyclic V3-Loop Related HIV-1 Conjugate Vaccines," *Int. J. Peptide Protein Res.*, 41, pp. 455-466 (1993).
Conley, et al., "Immunogenicity of Synthetic HIV-1 Gp120 V3-Loop Peptide-Conjugate Immunogens," *Vaccine*, 12(5), pp. 445-451 (1994).
Schneider, et al., "Induction of CD8+T Cells Using Heterologous Prime-Boost Immunisation Strategies," *Immunol. Rev.*, 170, pp. 29-38 (1999).
Tanghe, et al., "Improved Immunogenicity and Protective Efficacy of a Tuberculosis DNA Vaccine Encoding Ag85 by Protein Boosting," *Infect. and Immun.*, 69(5), pp. 3041-3047 (2001).
Gonzalo, et al., "A Heterologous Prime-Boost Regime Using DNA and Recombinant Vaccinia Virus Expressing the *Leishmania infantum* P36/LACK Antigen Protects BALB/c Mice From Cutaneous Leishmaniasis," *Vaccine*, 20, pp. 1226-1231 (2002).
Meyer, et al., "Complement-Mediated Enhancement of Antibody Function for Neutralization of Pseudotype Virus Containing Hepatitis C Virus E2 Chimeric Glycoprotein," *J. of Virol.*, 76(5), pp. 2150-2158 (2002).
Robinson, "New Hope for an AIDSs Vaccine," *Nat. Rev. Immunol.*, 2, pp. 239-250 (Apr. 2002).
Lu, et al., "Multiepitope Trojan Antigen Peptide Vaccines for the Induction of Antitumor CTL and Th Immune Responses," *J. of Immunol.*, 172, pp. 4575-4582 (2004).
Westerfeld, et al., "Peptides Delivered by Immunostimulating Reconstituted Influenza Virosomes," *J. of Peptide Sci.*, 11(11), pp. 707-712 (2005).
Gerhard, et al., "Prospects for Universal Influenza Virus," *Emerging Infectious Diseases*, 12(4), pp. 569-574 (Apr. 2006).

Luo, "Structural Biology: Antiviral Drugs Fit for a Purpose," *Nature*, 443, pp. 37-38 (Sep. 1, 2006).
PepTcell Ltd., "Technology," http://www.peptcell.com/technology.aspx (2007).
Stoloff, et al., "Synthetic Multi-Epitope Peptides Identified in Silico Induce Protective Immunity Against Multiple Influenza Serotypes," *Eur. J. of Immunol.*, 37(9), pp. 2441-2449 (Aug. 2, 2007).
Depla, et al., "Rational Design of a Multiepitope Vaccine Encoding T-Lymphocyte Epitopes for Treatment of Chronic Hepatitis B Virus Infections," *J. of Virol.*, 82(1), pp. 435-450 (Jan. 2008).
Blow, et al., "Viral Nucleic Acid Stabilization by RNA Extraction Reagent," *J. of Viral. Meth.*, 150, pp. 41-44 (Apr. 2, 2008).
Henke et al., "Betaine Improves the PCR Amplification of GC-Rich DNA Sequences," Nucleic Acids Research 25(19): 3957-3958 (1997).
Yue et al., "Detection of rifampin-resistant *Mycobacterium tuberculosis* strains by using a specialized oligonucleotide microarray," Diagnostic Microbiology and Infectious Disease, 48(1): 47-54 (2004).
Canadian Office Action for application No. 2697373, dated Feb. 19, 2013.
CA Office action for PCT/US08/78499, dated Mar. 29, 2012.
Miyazaki, et al., "Development of a monolithic silica extraction top for the analysis of proteins," J. Chromatogr. A., 1043(1): 19-25 (2004) [abstract only].
PCT Patentability Report for PCT/US2012/35253, dated Sep. 21, 2012.
Taiwan Office Action dated Aug. 20, 2012.
PCT Search Report for PCT/US13/32354, dated May 31, 2013.
Chinese Office Action for Application No. 201080028416.4.
Chinese Search Report for Application No. 201080028416.4.
IL Exam Report for PCT/US2007/078025, dated Mar. 7, 2013.
EPO Exam Report for EP12180376, dated Feb. 8, 2013.
Canadian Office Action for application No. 2759028, dated Apr. 12, 2013.
"Development of an Internal Positive Control for Rapid Diagnosis of Avian Influenza, etc.", A.Das, et al., Journal of Clinical Microbiology, Sep. 2006, vol. 44, No. 9, pp. 3065-3073.
De Moreau de Gerbehaye, A.I. et al., "Stable Hepatitis C Virus RNA Detection by RT-PCR During Four Days Storage," BioMed Central, BMC Infectious Diseases, 2:22 (2002).
"Evaluation of PCR Testing of Ethanol-Fixed Nasal Swab Specimens, etc." A.Krafft, et al., Journal of Clinical Microbiology, Apr. 2005, vol. 43, No. 4, pp. 1768-1775.
"Abstracts—27th Annual Meeting for the European Society for Paediatric Infectious Disease, Brussels, Belgium, Jun. 9-13, 2009," The Ped. Infect. Dis. J., 28(6):e1, e75, e229 (Jun. 2009).
"AgPath-ID One-Step RT-PCR Kit," Applied Biosystems, available at http://www.abion.com/techlib/prot/bp_1005.pdf (last visited Aug. 24, 2009).
Lin, B., et al., "Broad-Spectrum Respiratory Tract Pathogen Identification Using Resequencing DNA Microarrays." Genome Res., 16:527-35 (2006).
Buck et al. BioTechniques vol. 27, pp. 528-536, Sep. 1999.
Wolff, C. et al, "Single-Tube Nested PCR With Room-Temperature-Stable Reagents," Cold Spring Harbor Laboratory Press, PCR Methods and Appl., 4:376-79 (1995).
Schultz, C.L., et al., "A Lysis, Storage, and Transportation Buffer for Long-Term, Room-Temperature Preservation of Human Clinical Lymphoid Tissue Samples Yielding High Molecular Weight Genomic DNA Suitable for Molecular Diagnosis," Am. J. Clin. Pathol., 111(6):748-52 (1999).
Characterization of Novel Influenza 2005.
"Collecting, Preserving, Shipping Specimens for the Diagnosis of Avian Influenza (H5N1) Virus Infection: Guide for Field Operations," WHO/CDS/EPR/ARO/2006.1 (2006).
Daum, et al., Abstract—"A Molecular Transport Medium (MTM) for Pathogen Inactivation, Ambient Transport and Preservation of RNA from Clinical Samples," ICAAC, Boston, MA, Sep. 12-15, 2010.
Daum, et al., Abstract and Poster—"Development of a Real Time Reverse-Transcription PCR (RRT-PCR) Assay for Detection of

(56) References Cited

OTHER PUBLICATIONS

Influenza A H1N1 2009 From Clinical Respiratory Specimens," Pediatric Infectious Disease Conference ESPID, Nice, France, May 5-8, 2009.
Daum, et al., Abstract and Poster—"Development of a Real Time Reverse-Transcription PCR (RRT-PCR) Assay for Detection of Influenza A H1N1 2009 from Clinical Respiratory Specimens," Pediatric Infectious Disease Conference ESPID, Nice, France, May 5-8, 2010.
De Silva at al. Influenza A virus (A/Nonthaburi/102/2009(H1N1)) segment 4 hemagglutinin (HA) gene, partial cds. Genbank Accession No. GQ 132184.1, submitted May 9, 2009.
Spackman, E., et al., "Development of a Real-Time Reverse Transcriptase PCR Assay for Type A Influenza Vrius and the Avian H5 and H7 Hemagglutinin Subtypes," J. Clinic. Mirobiol., 40(9): 3256-60 (2002).
Hindiyeh et al. Journal of Clinical Microbiology, vol. 43, No. 2, pp. 589-595, Feb. 2005.
J. Mahoney et al., "Multiplex RT-PCR for detecting nineteen respiratory viruses," Journal of Clinical Virology, vol. 36, Jan. 1, 2006, p. S9.
"Adamantane Resistance Among Influenza, etc.", JAMA, Feb. 22, 2006, vol. 295, No. 8, pp. 891-894.
"KOD Hot Start DNA Polymerase," Novagen, available at http://www.emdbiosciences.com/ProductDisplay.asp?catno=71086 (last visited Aug. 24, 2009).
Kutyavin et al. 3'-Minor groove binder-DNA probes increase sequence specificity at PCR extension temperatures. Nucleic Acid Res. (2000) vol. 28, No. 2, pp. 655-661.
"Genetic and Antigenic Analysis of the First A/New Calendonia, etc.", L.Daum, et al., Emerging Infectious Diseases, vol. 8, No. 4, Apr. 2002, pp. 408-412.
Canas, L.C., "Clinical Laboratory: Selection, Collection and Transport of Specimens for Viral Cultures." Department of the Air Force, Air Force Institute of Operational Health (AFIOH), Epidemiological Surveillance Division, SDE O1 44/5001, Virol. Proc. Man., 1-8 (2005).
Daum L.T., et al., "Molecular Analysis of Isolates From Influenza B Outbreaks in the U.S. and Nepal, 2005," Arch. of Virol., 151:1863-1874 (2006).
Daum, L.T. et al., "Real-Time RT-PCR Assays for Type and Subtype Detection of Influenza A and B Viruses," Influenza & Other Resp. Viruses 1(4): 167-75 (2007).
Daum, L.T., et al., "Abstract—Quantification of Influenza A Virus From Nasal and Lung Tissue of Cotton Rats Using Real-Time RT-PCR and Culture," 26th Annual Meeting of the European Society for Pediatric Infectious Diseases, Graz, Austria (2008).
Daum, L.T., et al., "Abstract—Development and Clinical Evaluation of Rapid Real-Time RT-PCR Assays for Detection of Influenza A and B Viruses," 26th Annual Meeting of the European Society for Pediatric Infectious Diseases, Graz, Austria (2008).
Daum, L.T., et al., "Poster—A Novel Specimen Collection Solution for Molecular Diagnostic Applications," The Pediatric Academic Societies (PAS) Annual Meeting, Honolulu, HI (2008).
Daum, L.T., et al., "Poster—A Rapid, Simplified Collection-to-Detection System for Typing and Subtyping Influenza Viruses Using Real-Time RT-PCR and Culture," American Society for Microbiology (ASM) Conference on Emerging Technologies of Medical Importance for the Diagnosis of Infectious Diseases and the Detection of Pathogenic Microbes, Beijing, China (2008).
Daum, L.T., et al., "Poster—Real-Time RT-PCR Detection of Influenza A Virus in Asymptomatic Culture-Negative Cotton Rats," The Pediatric Academic Societies (PAS) Annual Meeting, Honolulu, HI (2008).
Daum, L.T., et al., "A Rapid, Single-Step Multiplex Reverse Transcription—PCR Assay for the Detection of Human H1N1, H3N2 and B Influenza Viruses." J. of Clinic. Virol., 25(3): 345-50 (2002).
Daum, L.T., et al., "Real-Time RT-PCR Detection of Influenza Virus Within Symptomatic and Asymptomatic Family Members," The 48th Annual IDSA/ICAAC, Washington D.C. (2008).
Lowe et al. A computer program for selection of oligonucleotide primers for polymerase chain reactions. Nucleic Acids Research (1990) vol. 18, No. 7, pp. 1757-1761.
Luke T. Daum et al., "Detection and Molecular Characterization of Clinical Influenza A and B Viruses from Original Nasal Wash Specimens Preserved in PrimeStore," (2008).
Luke T. Daum et al., "Portugal Meeting Poster (Introduction, Materials, and Methods, Results, Discussion)," (2008).
"Luminex Confirms Effectiveness of xTAG Respiratory Viral Panel for Swine Flu Surveillance," Medical News Today, available at http://www.medicalnewstoday.com/printerfriendlynews.php?newsid=148498 (May 1, 2009).
"Luminex Receives FDA Clearance for an Update to the xTAG Respiratory Panel Insert Package Insert to Include Data from Two New Publications on 2009 Influenza A/H1N1," available at http://phx.corporate-ir.net/phoenix.zhtml?c=79403&p=irol-newsArticle&ID=1307416&highlight= (Jul. 14, 2009).
Borns, M. et al., "Most Accurate PCR Enzyme Inproved With Hot Start Feature," Biocompare, available at http://www.biocompare.com/technicalarticle/212/Most-Accurate-PCR-Enzyme-Improved-With-Hot-Start-Feature-from-Startagene.html (last visited Aug. 24, 2009).
Denhart, M., and Doraiswamy, V., "Master Your PCR Domain!" Promega Notes, 78: 9-12 (2001).
Master Your PCR Domain.
"Tools of Biochemistry 5A—Ways to Isolate and Purify Proteins and Other Macromolecules", Matthews, et al., Biochemistry, Second Edition, 1996, pp. 152-155.
Tortora, et al., "Tools of Biochemistry 5A—Ways to Isolate and Purify Proteins and Other Macromolecules," Microbiology—An Introduction, pp. 152-155, 4th Ed., The Benjamin/Cummings Publishing Company, Inc., United States (1992).
Matthews, et al., "Immunofluorescence and Fluorescent Antibody Techniques," Biochemistry, pp. 461-63, 2nd Ed., The Benjamin/Cummings Publishing Company, Inc., United States (1996).
Morre, et al., "RNA Amplification by Nucleic Acid Sequence-Based Amplification with an Internal Standard Enables Reliable Detection of *Chlamydia trachomatis* in Cervical Scrapings and Urine Samples," *J. of Clinical Microbiol*, 34(12): 3108-3114 (1996).
http://www.ncbi.nim.nih.gov/genomes/FLU/SwineFlu2009.html.
NCBI Influenza Virus Resource "CLE I. GenBank Sequence from Pandemic (H1N1) 2009 Viruses". 1237 pages.
Pheng, O.C. Et al., "Temperature Related Storage Evaluation of an RT-PCR Test Kit for the Detection of Dengue Infection in Mosquitoes," (Research Note), Tropical Biomedicine, 22(1):73-6 (2005).
"Single-Step Method of RNA Isolation by Acid Guanidinium, etc.", P. Chomczyniski, et al., Analytical Biochemistry 162, 1987, pp. 156-159.
Pamphlet—"Prime PCR System"—Longhorn Vaccines & Disagnostics.
"PCR Optimization: Reaction Conditions and Components," Applied Biosystems, Part No. 4371091, Revision C, pp. 1-6 available at http://www.appliedbiosystems.com/cms/groups/mcb_marketing/documents/generaldocuments/cms_042520.pdf (last visited Aug. 24, 2009).
"PCR-Ready Clear Supreme," Syntezza Bioscience Ltd., available at http://www.syntezza.com/egt/PCR-Ready_Clear Supreme.pdf (2006).
European Patent Office, "PCT Notification of Transmittal of the International Search Report and The Written Opinion of the International Searching Authority or the Declaration, PCT International Search Report, PCT Written Opinion of the International Searching Authority—Application No. PCT/US2007/078025," Nov. 13, 2008, 10 pages, Munich.
European Patent Office, "PCT Notification of Transmittal of the International Search Report and the Written Opinion of the International Searching Authority—Application No. PCT/US2008/078499," mailed Aug. 4, 2009, 13 pages.
Ramanujam, R. et al., "Room-Temperature-Stable PCR Reagents," Cold Spring Harbor Laboratory Press, PCR Methods and Appl., 3:75-76 (1993).

(56) References Cited

OTHER PUBLICATIONS

Bright, R.A., et al., "Adamantane Resistance Among Influenza A Viruses Isolated Early During the 2005-2006 Influenza Season in the United States," JAMA, 295(8):891-4 (Feb. 22, 2006).
Fouchier, R.A.M. et al., "Characterization of a Novel Influenza A Virus Hemagglutinin Subtype (H16) Obtained From Black-Headed Gulls," J. of Virol. 79(5):2814-22 (Mar. 2005).
"R.A.P.I.D System," Idaho Technology Inc., available at http://www.idahotech.com/RAPID/Rapid-Water.html (last visited Aug. 24, 2009).
Magari, R.T., Assessing shelf life using real-time and accelerated stability tests, BioPharm Nov. 2003.
Rosenstraus, et al., "An Internal Control for Routine Diagnostic PCR: Design, Properties, and Effect on Clinical Performance," J. of Clinical Microbial, 36(1): 191-197 (1998).
RU 2150281.
Blacksell, S.D. et al., "The Effect of Sample Degradation and RNA Stabilization on Classical Swine Fever Virus RT-PCR and Elisa methods," J. Virol. Methods, 118(1):33-7 (2004).
"Single Tube PCR Kit Manual," Takara Bio Inc., Cat #RR021, V.02.09, pp. 1-6 available at http://www.takara-bio.us/files/manuels/TAK__RR021__TM.pdf (last visited Aug. 24, 2009).
"Taq PCR Master Mix (2x)," USB Corp., (2007).
"TechNotes Newsletter," Applied Biosystems, 14(4):1-37 (2007).
"Immunoflourescence and Fluorescent-Antibody Techniques", Tortora, et al., Microbiology—An Introduction, Fourth Edition, 1992, pp. 461-463.
"USB Taq PCR Master Mix in qPCR," USB Corporation, Tech Tips, 207 (2005).
World Health Organization, "CDC protocol of realtime RTPCR for influenza A (H1N1)," Apr. 28, 2009.
Wiecek, A., "Pocket PCR: The Whole Chain Reaction in His Hand," Biotechniques.com, Oct. 26, 2010.
Wang, Z., et al., "Identifying Influenza Viruses with Resequencing Microarrays," Emerg. Infect. Dis. 12(4):638-46 (2006).
Danila Valmori et al. "Use of human universally antigenic tetanus toxin T cell epitopes as carriers for human vaccination" Journal of Immunology, Jul. 15, 1992.
PCT Search Report for PCT/US10/43546 dated Nov. 16, 2010.
PCT Search Report for PCT/US10/31716 dated Jul. 28, 2010.
PCT Written Opinion for PCT/US10/31716 dated Oct. 25, 2011.
PCT Search Report for PCT/US2008/074521 dated Feb. 13, 2009.
PCT Written Opinion for PCT/US2008/074521 dated May 3, 2009.
PCT Search Report for PCT/US2007/078025 dated Oct. 28, 2008.
PCT Written Opinion for PCT/US2007/078025 dated Mar. 17, 2009.
PCT Search Report for PCT/US2008/078499 dated Jul. 23, 2009.
PCT Written Opinion for PCT/US2008/078499 dated Jul. 4, 2010.
Austalian Exam Report for Application No. 2012239385, dated Oct. 9, 2013.
Austalian Exam Report for Application No. 2012211365, dated Oct. 9, 2013.
Max, et al Reliability of PCR-based detection of occult tumour cells: lessons from real-time RT-PCR.
EP Search Report for Application No. 13175959, dated Nov. 18, 2013.
PCT Search and Patentability Report for PCT/US2013/077038, dated Mar. 10, 2014.
CA Office Action for CA Application No. 2701168, dated Mar. 4, 2014.

\* cited by examiner

Influenza A Virus Genome Segment 7

FIG.2

Conserved Neuraminidase Peptides
H1 and H5 NA

| NA Peptide Sequence | Length | Rationale |
| --- | --- | --- |
| DWSGYSGSFVQHPELTGL (SEQ ID NO:11) | 18 aa | Longest conserved stretch of amino acids in entire NA; located in the NA globular head; Located at position 398-415 at the conserved 3' end. |
| HYEECSCY (SEQ ID NO:7) | 8 aa | Located in the NA globular head active site region; 3 of these aa (H, E, E) are involved in Catalysis of SA; one (first E) contacts SA directly. |
| FVIREPFISCSHLEC (SEQ ID NO:3) | 15 aa | Located in the NA globular 5' end. 2 aa (R and first E) bind Sialic Acid. |

FIG.7

Conserved Epitopes in the Influenza H5,H3, H1 HA Protein

Depicted in Black:
GLY 249
ASN 250
LEU 251(H3/H1)
PHE 251 (H5)
ILE 252
ALA 253
PRO 254

FIG.9

Influenza A (H1N1)

| Sequence Name | < Pos = 262 | |
|---|---|---|
| – + | | |
| Consensus | NGNLIAPRYAFALSRGFGSGIITSNAPMDE | (SEQ ID NO: 58) |
| 10 Sequences | 270 280 290 | |
| A/Texas/1b/2008 | NGNLIAPRYAFALSRGFGSGIINSNAPMDK | (SEQ ID NO: 59) |
| A/Texas/1a/2008 | NGNLIAPRYAFALSRGFGSGIINSNAPMDK | (SEQ ID NO: 60) |
| A/Brisbane/59/2007* | NGNLIAPRYAFALSRGFGSGIINSNAPMDK | (SEQ ID NO: 61) |
| A/Bayern/7/1995 | NGNLIAPWYAFALSRGFGSGIITSNASMGE | (SEQ ID NO: 62) |
| A/Beijing/262/1995* | NGNLIAPWYAFALSRGFGSGIITSNAPMNE | (SEQ ID NO: 63) |
| Solomon Islands.3.2006* | NGNLIAPRYAFALSRGFGSGIINSNAPMDE | (SEQ ID NO: 64) |
| A/New Caledonia/20/1999* | NGNLIAPWYAFALSRGFGSGIITSNAPMDE | (SEQ ID NO: 65) |
| A/Peru/3175/2001 | NGNLIAPRYAFALSRGFGSGIITSNAPMDE | (SEQ ID NO: 66) |
| A/Georgia/2/2003 | NGNLIAPWYAFALSRGFGSGIITSNAPMDE | (SEQ ID NO: 67) |
| A/Saudia Arabia/2231/2001 | NGNLIAPWYAFALSRGFGSGIITSNAPMDE | (SEQ ID NO: 68) |

FIG.26A

Influenza A (H3N2)

| Sequence Name | < Pos = 255 | | |
|---|---|---|---|
| – + Consensus | NSTGNLIAPRGYFKIRSGKSSIMRSDAPIGKCN | | |
| 11 Sequences | 260　　　　　270　　　　　280 | | |
| A/Wisconsin/67/2005* | NSTGNLIAPRGYFKIRSGKSSIMRSDAPIGKCN | (SEQ ID NO: | 69) |
| A/California/7/2004* | NSTGNLIAPRGYFKIRSGKSSIMRSDAPIGKCN | (SEQ ID NO: | 69) |
| A/California/7383/2007 | NSTGNLIAPRGYFKIRSGKSSIMRSDAPIGKCN | (SEQ ID NO: | 69) |
| A/Fujian/411/2002* | NSTGNLIAPRGYFKIRSGKSSIMRSDAPIDKCN | (SEQ ID NO: | 69) |
| A/Japan/217/2007 | NSTGNLIAPRGYFKIRSGKSSIMRSDAPIGKCN | (SEQ ID NO: | 70) |
| A/Kenya/2041/2006 | NSTGNLIAPRGYFKIRSGKSSIMRSDAPIGKCN | (SEQ ID NO: | 69) |
| A/Korea/68/2006 | NSTGNLIAPRGYFKIRSGKSSIMRSDAPIGKCN | (SEQ ID NO: | 69) |
| A/Nepal/6128/2006 | NSTGNLIAPRGYFKIRSGKSSIMRSDAPIGKCK | (SEQ ID NO: | 69) |
| A/Brisbane/10/2007* | NSTGNLIAPRGYFKIRSGKSSIMRSDAPIGKCN | (SEQ ID NO: | 69) |
| A/Texas/78209/2008 | NSTGNLIAPRGYFKIRSGKSSIMRSDAPIGKCN | (SEQ ID NO: | 69) |
| A/Texas/17/2008 | NSTGNLIAPRGYFKIRSGKSSIMRSDAPIGKCN | (SEQ ID NO: | 69) |

FIG. 26B

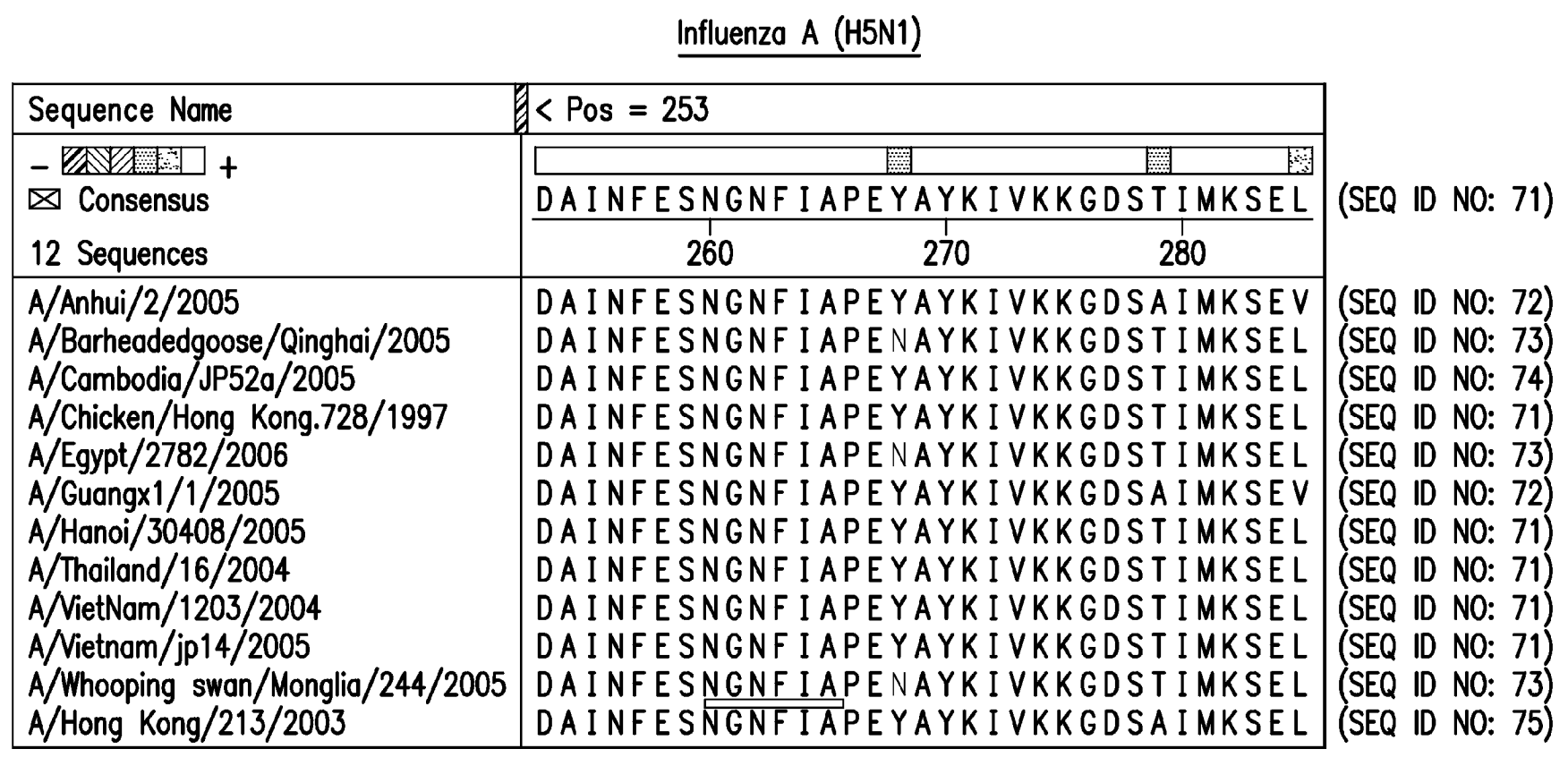

Influenza A (H5N1)

| Sequence Name | < Pos = 253   D A I N F E S N G N F I A P E Y A

```
                          SEQUENCE LISTING

<160> NUMBER OF SEQ ID NOS: 75

<210> SEQ ID NO 1
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 1

Asp Trp Ser Gly Tyr Ser Gly Ser Phe Val Gln His Pro Glu Leu Thr
1               5                   10                  15

Gly Leu Asp

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Glu Thr Pro Ile Arg Asn Glu
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 3

Phe Val Ile Arg Glu Pro Phe Ile Ser Cys Ser His Leu Glu Cys
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Gly Asn Phe Ile Ala Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Gly Asn Leu Phe Ile Ala Pro
1               5

<210> SEQ ID NO 6
<211> LENGTH: 6
<212> TYPE: PRT
```

<213> ORGANISM: Artificial Sequence
<220> FEATURE:
<223> OTHER INFORMATION: Synthetic Peptide

<400> SEQUENCE: 6

Gly Asn Leu Ile Ala Pro
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

His Tyr Glu Glu Cys Ser Cys Tyr
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 8

Leu Leu Thr Glu Val Glu Thr Pro Ile Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Leu Leu Thr Glu Val Glu Thr Pro Ile Arg Asn
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 10

Leu Leu Thr Glu Val Glu Thr Pro Ile Arg Asn Glu
1               5                   10

<210> SEQ ID NO 11
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 11

Asp Trp Ser Gly Tyr Ser Gly Ser Phe Val Gln His Pro Glu Leu Thr
1               5                   10                  15

Gly Leu

<210> SEQ ID NO 12
<211> LENGTH: 9

```
<212> TYPE: PRT
<213> ORGANISM: Artificial Sequence
<220> FEATURE:
<223> OTHER INFORMATION: Synthetic Peptide

<400> SEQUENCE: 12

Glu Val Glu Thr Pro Ile Arg Asn Glu
1               5

<210> SEQ ID NO 13
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 13

Phe Leu Leu Pro Glu Asp Glu Thr Pro Ile Arg Asn Glu Trp Gly Leu
1               5                   10                  15

Leu Thr Asp Asp Glu Thr Pro Ile Arg Tyr Ile Lys Ala Asn Ser Lys
            20                  25                  30

Phe Ile Gly Ile Thr Glu
        35

<210> SEQ ID NO 14
<211> LENGTH: 64
<212> TYPE: PRT
<213> ORGANISM: Artificial Sequence
<220> FEATURE:
<223> OTHER INFORMATION: Synthetic Peptide

<400> SEQUENCE: 14

Gly Asn Leu Phe Ile Ala Pro Gly Asn Leu Phe Ile Ala Pro His Tyr
1               5                   10                  15

Glu Glu Cys Ser Cys Tyr His Tyr Glu Glu Cys Ser Cys Tyr Gln Tyr
            20                  25                  30

Ile Lys Ala Asn Ser Lys Phe Ile Gly Ile Thr Glu His Tyr Glu Glu
            35                  40                  45

Cys Ser Cys Tyr Thr Pro Ile Arg Asn Glu Thr Pro Ile Arg Asn Glu
        50                  55                  60

<210> SEQ ID NO 15
<211> LENGTH: 35
<212> TYPE: PRT
<213> ORGANISM: Artificial Sequence
<220> FEATURE:
<223> OTHER INFORMATION: Synthetic Peptide

<400> SEQUENCE: 15

Gly Asn Leu Phe Ile Ala Pro Gly Asn Leu Phe Ile Ala Pro Gln Tyr
1               5                   10                  15

Ile Lys Ala Asn Ser Lys Phe Ile Gly Ile Thr Glu Gly Asn Leu Phe
            20                  25                  30

Ile Ala Pro
        35

<210> SEQ ID NO 16
<211> LENGTH: 48
<212> TYPE: PRT
<213> ORGANISM: Artificial Sequence
<220> FEATURE:
<223> OTHER INFORMATION: Synthetic Peptide

<400> SEQUENCE: 16
```

```
His Tyr Glu Glu Cys Ser Cys Tyr Asp Trp Ser Gly Tyr Ser Gly Ser
1               5                   10                  15

Phe Val Gln His Pro Glu Leu Thr Gly Leu His Tyr Glu Glu Cys Ser
                20                  25                  30

Cys Tyr Gln Tyr Ile Lys Ala Asn Ser Lys Phe Ile Gly Ile Thr Glu
            35                  40                  45
```

<210> SEQ ID NO 17
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 17

```
Ile Thr Gly Phe Ala Pro Phe Ser Lys Asp Asn Ser Ile Arg Leu Ser
1               5                   10                  15

Ala Gly Gly Asp Ile Trp Val Thr Arg Glu Pro Tyr Val Ser Cys Asp
                20                  25                  30

Pro
```

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

```
Ile Trp Gly Ile His His Pro
1               5
```

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

```
Ile Trp Gly Val His His Pro
1               5
```

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

```
Lys Ser Cys Ile Asn Arg Cys Phe Tyr Val Glu Leu Ile Arg Gly Arg
1               5                   10                  15
```

<210> SEQ ID NO 21
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 21

```
Leu Leu Thr Glu Val Glu Thr Pro Ile Arg Asn Glu Ser Leu Leu Thr
1               5                   10                  15
```

Glu Val Glu Thr Pro Ile Arg Asn Glu Trp Gly
            20                  25

<210> SEQ ID NO 22
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 22

Leu Leu Thr Glu Val Glu Thr Pro Ile Arg Asn Glu Trp
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 23

Leu Leu Thr Glu Val Glu Thr Pro Ile Arg Asn Glu Trp Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 24

Leu Thr Glu Val Glu Thr Pro Ile Arg Asn Glu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Leu Thr Glu Val Glu Thr Pro Ile Arg Asn Glu Trp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 26

Leu Thr Glu Val Glu Thr Pro Ile Arg Asn Glu Trp Gly
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 27

```
Met Ser Leu Leu Thr Glu Val Glu Thr
1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 28

Met Ser Leu Leu Thr Glu Val Glu Thr Pro
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 29

Met Ser Leu Leu Thr Glu Val Glu Thr Pro Ile
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 30

Met Ser Leu Leu Thr Glu Val Glu Thr Pro Ile Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 31

Met Ser Leu Leu Thr Glu Val Glu Thr Pro Ile Arg Asn
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 32

Met Ser Leu Leu Thr Glu Val Glu Thr Pro Ile Arg Asn Glu
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 33

Met Ser Leu Leu Thr Glu Val Glu Thr Pro Ile Arg Asn Glu Thr Pro
```

```
Ile Arg Asn Glu
            20

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 34

Met Ser Leu Leu Thr Glu Val Glu Thr Pro Ile Arg Asn Glu Trp
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 35

Met Ser Leu Leu Thr Glu Val Glu Thr Pro Ile Arg Asn Glu Trp Gly
1               5                   10                  15

<210> SEQ ID NO 36
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 36

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 37
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 37

Ser Leu Leu Thr Glu Val Glu Thr
1               5

<210> SEQ ID NO 38
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 38

Ser Leu Leu Thr Glu Val Glu Thr Pro Ile Arg Asn Glu
1               5                   10

<210> SEQ ID NO 39
<211> LENGTH: 14
<212> TYPE: PRT
<213> ORGANISM: Artificial Sequence
<220> FEATURE:
```

```
<223> OTHER INFORMATION: Synthetic Peptide

<400> SEQUENCE: 39

Ser Leu Leu Thr Glu Val Glu Thr Pro Ile Arg Asn Glu Trp
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 40

Ser Leu Leu Thr Glu Val Glu Thr Pro Ile Arg Asn Glu Trp Gly
1               5                   10                  15

<210> SEQ ID NO 41
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 41

Ser Leu Leu Thr Glu Val Glu Thr Pro Ile Arg Asn Glu Trp Gly Thr
1               5                   10                  15

Pro Ile Arg Asn Glu
            20

<210> SEQ ID NO 42
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 42

Ser Leu Leu Thr Glu Val Glu Thr Pro Ile Arg Asn Glu Trp Gly Thr
1               5                   10                  15

Pro Ile Arg Asn Glu Thr Pro Ile Arg Asn Glu
            20                  25

<210> SEQ ID NO 43
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 43

Ser Leu Leu Thr Glu Val Glu Thr Pro Ile Arg Asn Glu Trp Gly Thr
1               5                   10                  15

Pro Ile Arg Asn Glu Thr Pro Ile Arg Asn Glu Thr Pro Ile Arg Asn
            20                  25                  30

Glu

<210> SEQ ID NO 44
<211> LENGTH: 39
<212> TYPE: PRT
<213> ORGANISM: Artificial Sequence
<220> FEATURE:
<223> OTHER INFORMATION: Synthetic Peptide

<400> SEQUENCE: 44
```

```
Ser Leu Leu Thr Glu Val Glu Thr Pro Ile Arg Asn Glu Trp Gly Leu
1               5                   10                  15

Leu Thr Glu Val Glu Thr Pro Ile Arg Gln Tyr Ile Lys Ala Asn Ser
            20                  25                  30

Lys Phe Ile Gly Ile Thr Glu
        35
```

<210> SEQ ID NO 45
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 45

```
Thr Glu Val Glu Thr Pro Ile Arg Asn Glu
1               5                   10
```

<210> SEQ ID NO 46
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 46

```
Thr Pro Ile Arg Asn Glu
1               5
```

<210> SEQ ID NO 47
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 47

```
Val Glu Thr Pro Ile Arg Asn Glu
1               5
```

<210> SEQ ID NO 48
<211> LENGTH: 52
<212> TYPE: PRT
<213> ORGANISM: Artificial Sequence
<220> FEATURE:
<223> OTHER INFORMATION: Synthetic Peptide

<400> SEQUENCE: 48

```
Val Thr Arg Glu Pro Tyr Val Ser Cys Asp Pro Lys Ser Cys Ile Asn
1               5                   10                  15

Arg Cys Phe Tyr Val Glu Leu Ile Arg Gly Arg Val Thr Arg Glu Pro
            20                  25                  30

Tyr Val Ser Cys Asp Pro Trp Tyr Ile Lys Ala Asn Ser Lys Phe Ile
        35                  40                  45

Gly Ile Thr Glu
    50
```

<210> SEQ ID NO 49
<211> LENGTH: 6
<212> TYPE: PRT
<213> ORGANISM: Artificial Sequence
<220> FEATURE:
<223> OTHER INFORMATION: Synthetic Peptide

```
<400> SEQUENCE: 49

Trp Gly Ile His His Pro
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 50

Trp Gly Val His His Pro
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 51

Tyr Ile Trp Gly Ile His His Pro
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 52

Tyr Ile Trp Gly Val His His Pro
1               5

<210> SEQ ID NO 53
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 53

Gln Tyr Ile Lys Ala Asn Ser Lys Phe Ile Gly Ile Thr Glu
1               5                   10

<210> SEQ ID NO 54
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 54

Pro Ile Arg Asn Glu Trp Gly Cys Arg Cys Asn Asp Ser Ser Asp
1               5                   10                  15

<210> SEQ ID NO 55
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 55
```

```
Ser Ile Glu Leu Glu
1               5

<210> SEQ ID NO 56
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 56

Met Ser Leu Leu Thr Glu Val Glu Thr Tyr Val Leu Ser Ile Val Pro
1               5                   10                  15

<210> SEQ ID NO 57
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 57

Met Gln Arg Phe Lys
1               5

<210> SEQ ID NO 58
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 58

Asn Gly Asn Leu Ile Ala Pro Arg Tyr Ala Phe Ala Leu Ser Arg Gly
1               5                   10                  15

Phe Gly Phe Gly Ile Ile Thr Ser Asn Ala Pro Met Asp Glu
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 59

Asn Gly Asn Leu Ile Ala Pro Arg Tyr Ala Phe Ala Leu Ser Arg Gly
1               5                   10                  15

Phe Gly Phe Gly Ile Ile Asn Ser Asn Ala Pro Met Asp Lys
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 60

Asn Gly Asn Leu Ile Ala Pro Arg Tyr Ala Phe Ala Leu Ser Arg Gly
1               5                   10                  15

Phe Gly Ser Gly Ile Ile Asn Ser Asn Ala Pro Met Asp Lys
            20                  25                  30
```

```
<210> SEQ ID NO 61
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 61

Asn Gly Asn Leu Ile Ala Pro Arg Tyr Ala Phe Ala Leu Ser Arg Gly
1               5                   10                  15

Phe Gly Ser Gly Ile Ile Asn Ser Asn Ala Pro Met Asp Lys
            20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 62

Asn Gly Asn Leu Ile Ala Pro Trp Tyr Ala Phe Ala Leu Ser Arg Gly
1               5                   10                  15

Phe Gly Ser Gly Ile Ile Thr Ser Asn Ala Ser Met Gly Glu
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 63

Asn Gly Asn Leu Ile Ala Pro Trp Tyr Ala Phe Ala Leu Ser Arg Gly
1               5                   10                  15

Phe Gly Ser Gly Ile Ile Thr Ser Asn Ala Pro Met Asn Glu
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 64

Asn Gly Asn Leu Ile Ala Pro Arg Tyr Ala Phe Ala Leu Ser Arg Gly
1               5                   10                  15

Phe Gly Ser Gly Ile Ile Asn Ser Asn Ala Pro Met Asp Glu
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 65

Asn Gly Asn Leu Ile Ala Pro Trp Tyr Ala Phe Ala Leu Ser Arg Gly
1               5                   10                  15

Phe Gly Ser Gly Ile Ile Thr Ser Asn Ala Pro Met Asp Glu
            20                  25                  30
```

<210> SEQ ID NO 66
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 66

Asn Gly Asn Leu Ile Ala Pro Arg Tyr Ala Phe Ala Leu Ser Arg Gly
1               5                   10                  15

Phe Gly Ser Gly Ile Ile Thr Ser Asn Ala Pro Met Asp Glu
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 67

Asn Gly Asn Leu Ile Ala Pro Trp Tyr Ala Phe Ala Leu Ser Arg Gly
1               5                   10                  15

Phe Gly Ser Gly Ile Ile Thr Ser Asn Ala Pro Met Asp Glu
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 68

Asn Gly Asn Leu Ile Ala Pro Trp Tyr Ala Phe Ala Leu Ser Arg Gly
1               5                   10                  15

Phe Gly Ser Gly Ile Ile Thr Ser Asn Ser Pro Met Asp Glu
            20                  25                  30

<210> SEQ ID NO 69
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 69

Asn Ser Thr Gly Asn Leu Ile Ala Pro Arg Gly Tyr Phe Lys Ile Arg
1               5                   10                  15

Ser Gly Lys Ser Ser Ile Met Arg Ser Asp Ala Pro Ile Gly Lys Cys
            20                  25                  30

Asn

<210> SEQ ID NO 70
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 70

Asn Ser Thr Gly Asn Leu Ile Ala Pro Arg Gly Tyr Phe Lys Ile Arg
1               5                   10                  15

Ser Gly Lys Ser Ser Ile Met Arg Ser Asp Ala Pro Ile Gly Lys Cys
            20                  25                  30

Lys

<210> SEQ ID NO 71
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 71

Asp Ala Ile Asn Phe Glu Ser Asn Gly Asn Phe Ile Ala Pro Glu Tyr
1               5                   10                  15

Ala Tyr Lys Ile Val Lys Lys Gly Asp Ser Thr Ile Met Lys Ser Glu
            20                  25                  30

Leu

<210> SEQ ID NO 72
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 72

Asp Ala Ile Asn Phe Glu Ser Asn Gly Asn Phe Ile Ala Pro Glu Tyr
1               5                   10                  15

Ala Tyr Lys Ile Val Lys Lys Gly Asp Ser Ala Ile Met Lys Ser Glu
            20                  25                  30

Val

<210> SEQ ID NO 73
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 73

Asp Ala Ile Asn Phe Glu Ser Asn Gly Asn Phe Ile Ala Pro Glu Asn
1               5                   10                  15

Ala Tyr Lys Ile Val Lys Lys Gly Asp Ser Thr Ile Met Lys Ser Glu
            20                  25                  30

Leu

<210> SEQ ID NO 74
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 74

Asp Ala Ile Asn Phe Glu Ser Asn Gly Asn Phe Ile Ala Pro Glu Tyr
1               5                   10                  15

Ala Tyr Lys Ile Val Lys Lys Gly Asp Ser Thr Ile Met Lys Ser Glu
            20                  25                  30

Leu

<210> SEQ ID NO 75

```
<211> LENGTH: 33
<212> TYPE: PRT
<213> ORGANISM: Artificial Sequence
<220> FEATURE:
<223> OTHER INFORMATION: Synthetic Peptide

<400> SEQUENCE: 75

Asp Ala Ile Asn Phe Glu Ser Asn Gly Asn Phe Ile Ala Pro Glu Tyr
1               5                   10                  15

Ala Tyr Lys Ile Val Lys Lys Gly Asp Ser Ala Ile Met Lys Ser Glu
            20                  25                  30

Leu
```

IMMUNOGENIC COMPOSITIONS AND METHODS

CROSS-REFERENCE TO RELATED APPLICATIONS

The present application claims the benefit of U.S. Provisional Application No. 60/968,145, filed Aug. 27, 2007, the entire contents of which is specifically incorporated herein in its entirety by express reference thereto.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

BACKGROUND OF THE INVENTION

1. Field of the Invention

The present invention relates generally to the fields of medicine and pharmaceuticals. More particularly, it concerns immunogenic compositions, methods of making such compositions, and methods for preventing, treating, ameliorating managing microbial or viral infection, or a symptom thereof, and particularly respiratory infections such as influenza or pneumococcal infection, or a combination of infections. Disclosed are target peptide antigen sequences and other epitopes that are conserved across related microbes, and even unrelated microbes, as well as immunogenic compositions and methods for their use in the formulation and administration of diagnostic, therapeutic, and prophylactic agents for diagnosing, treating, and/or preventing disease.

2. Description of Related Art

Microbial and viral pathogens are a primary source of infectious disease in animals. Pathogens and their hosts constantly adapt to one another in an endless competition for survival and propagation. Certain pathogens have become enormously successful at infecting mammalian hosts and surviving exposure to the host immune response, even over periods of years or decades. One example of an extremely successful mammalian pathogen is the influenzavirus.

Influenzaviruses are etiologic agents for a contagious respiratory illness (commonly referred to, and referred to herein, as "flu" or "the Flu") that primarily affects humans and other vertebrates. Influenzavirus infection can cause mild to severe illness, and can even lead to death. Every year in the United States, on average, 5% to 20% of the population contract the Flu; more than 200,000 people are hospitalized from complications of the infection; and about 36,000 people die from exposure to the pathogen.

Influenzavirus spreads from host to host through coughing or sneezing, with airborne droplets nuclei as the primary vectors of the disease. In humans, the virus usually spreads directly from person to person, although subjects can sometimes become infected by indirect contact of surfaces harboring the virus, and then touching their mouth or nose. Most healthy adults may be able to infect others beginning as much as a day before primary symptoms of the disease develop, and remain contagious for up to 5 days after becoming infected. Uncomplicated influenza illness is often characterized by an abrupt onset of constitutional and respiratory symptoms, including fever, myalgia, headache, malaise, nonproductive cough, sore throat, rhinitis, or a combination of one or more of these symptoms.

Currently, attempts to control the spread of pathogenic influenzavirus in animal populations are by vaccination and/or treatment with one or more anti-viral compounds. Inactivated influenza vaccines are now in worldwide use, especially in high-risk groups such as infants, the elderly, those without adequate health care and immunocompromised individuals. The vaccine viruses are typically grown in fertile hen's eggs, inactivated by chemical means and purified. The vaccines are usually trivalent, containing representative influenza A viruses (H1N1 and H3N2) and influenza B strains. The vaccine strains need to be regularly updated in order to maintain efficacy; this effort is coordinated by the World Health Organization (WHO). During inter-pandemic periods, it usually takes a minimum of eight months before an updated influenza vaccine is ready for market. Historically, however, viral pandemics are spread to most continents within four to fix months, and future viral pandemics are likely to spread even faster due to increased international travel. It is therefore inevitable that an effective vaccine made by conventional means will be unavailable or in very short supply during the first wave of any future widespread outbreak or pandemic.

Numerous vaccines capable of producing a protective immune response specific for such different and influenza viruses/virus strains have been produced in the last half century. These include whole virus vaccines, split virus vaccines, surface antigen vaccines and live attenuated virus vaccines. However, while appropriate formulations of any of these vaccine types are capable of producing a systemic immune response, live attenuated virus vaccines have the advantage of also being able to stimulate local mucosal immunity in the respiratory tract.

Because of the continual emergence (or re-emergence) of different influenza strains, new influenza vaccines are continually desired. Such vaccines typically are created using antigenic moieties of the newly emergent virus strains, thus, polypeptides and polynucleotides of novel, newly emergent, or newly re-emergent virus strains (especially sequences of antigenic genes) are highly desirable.

Because of the rapid mutation rate among Influenzaviruses, it is commonly believed that pandemic Flu could appear at any time. The severity of the next Influenza pandemic cannot be predicted, but modeling studies suggest that the impact of a pandemic on the United States, and the world as a whole, could be substantial. In the absence of any control measures (vaccination or drugs), it has been estimated that in the United States a "medium-level" pandemic could cause: 89,000 to 207,000 deaths; 314,000 and 734,000 hospitalizations; 18 to 42 million outpatient visits; and another 20 to 47 million people being sick. According to the Centers for Disease Control and Prevention (CDC) (Atlanta, Ga., USA), between 15% and 35% of the U.S. population could be affected by an influenza pandemic, and the economic impact could range between approximately $71 and $167 billion.

The CDC and the leading authorities on disease prevention recommend preventing the Flu through annual Flu vaccination. Conventional vaccines however, typically target the HA and NA antigens, and have been neither universally protective nor 100% effective at preventing the disease.

Without being bound by theory, it is believed that antigenic shift prevents Flu vaccines from being universally protective or from maintaining effectiveness over many years. It is speculated that the ineffectiveness of conventional vaccines may also be due, in part, to antigenic drift and the resulting variation within antigenic portions of the HA and NA proteins most commonly recognized by the immune system (i.e., immunodominant antigens). As a result, many humans may find themselves susceptible to the flu virus without an effective method of treatment available since influenza is constantly improving its resistance to current treatments. This scenario is particularly concerning with respect to the H5N1 virus, which is highly virulent but for which there is currently no widely available commercial vaccine to immunize susceptible human populations.

Currently available flu vaccines generally induce immunity to only a few strains, presumably to those that are currently circulating in humans. In addition, to achieve a protective immune response, some vaccines must be administered with high doses of antigen. This is particularly true for H5N1 vaccines. Furthermore, conventional influenza vaccines typically present epitopes in the same order as is found in nature, generally presenting whole viral proteins; consequently, relatively large amounts of protein are required to make an effective vaccine. As a result, each administration includes an increased cost associated with the dose amount, and there is increased difficulty in manufacturing enough doses to vaccinate the general public. Even further, the use of larger proteins elevates the risk of undesirable immune responses in the recipient host.

Antiviral compounds remain the mainstay for treating inter-pandemic diseases. Currently, they are also the only alternative for controlling pandemics during the initial period when vaccines are not available. Two classes of antiviral compounds are currently on the market: M2 inhibitors, such as amantadine and rimantadine; and the neuraminidase (NA) inhibitors, which include oseltamivir (Tamiflu®, Roche Laboratories, Inc., Nutley, N.J., USA) and zanamivir (Relenza®, GlaxoSmithKline, Inc., Research Triangle Park, N.C., USA). Both classes of molecules have proven efficacy in prevention and treatment of influenza.

Limited effectiveness against emergent strains, numerous side effects, and the risk of generating drug-resistant variants, however, remain among the major concerns for limiting their widespread use as chemoprophylactics. In particular, the H1N1 serotype has begun to show significant resistance to oseltamivir, and a recent study by the WHO showed 237 (14%) of 1703 H1N1 viruses had a mutation conferring resistance to the drug. Resistance rates were the highest in Norway (66% of isolates), France (40%), and Luxembourg (25%), and mutation have already been found in 18 of 37 countries where the viruses have been analyzed. The mutation was observed in 8% of the isolates studied in the United States.

Contemporary influenzavirus vaccines and antiviral therapeutics are limited by significant, fundamental shortcomings, and there remains an unmet need in the art for an immunogenic composition that is not as susceptible to microbial changes, for example, due to antigenic shift or drift, which thereby would remain effective across various strains and subtypes of influenza over time. In particular, new therapeutic and/or prophylactic modalities are needed to address future influenza pandemics, and new vaccines are needed that can complement conventional vaccines to provide more comprehensive protection against viral and microbial pathogens, such as the influenza virus, than is conventionally available.

It would be highly desirable to have target antigens or epitopes that are conserved across types, subtypes, and/or strains of viral and microbial pathogens, particularly influenza virus; are easily manufactured and stored so as to improve production capacity and vaccine availability; remain effective through at least two Flu seasons so as to reduce production requirements; require lower concentrations of protein; reduce undesirable immune responses; enhance protection even when a new human virus emerges or mutations occur in circulating strains; or any combination thereof.

BRIEF SUMMARY OF THE INVENTION

The present invention encompasses new and useful compositions, as well as methods of employing them that may advantageously improve delivery of therapeutic, diagnostic and/or prophylactic agents to an animal in need thereof. The invention provides compositions that preferably achieve synergies in efficacy, preparation, etc., by employing repeating sequences of target antigens to provide enhanced immunogenic response strength, and to increase the likelihood of immunogenic protection in fewer administrations and/or at a lower dosage than is capable with the conventional influenza vaccines.

Because the vaccines disclosed in the present invention are less susceptible to antigenic shift and drift than conventional vaccines, administration of the disclosed immunogenic compositions may also reduce or eliminate the necessity of annual vaccination to maintain protection of patient populations against potential outbreaks of infection from new viral isolates.

Moreover, the immunogenic compositions of the present invention generally and advantageously can provide one or more of the following: increased safety considerations, a relatively long shelf life in part due to minimized need to reformulate due to strain-specific shift and drift, an ability to target immune responses with high specificity for particular microbial epitopes, and the ability to prepare multi-pathogen vaccines.

In an overall and general sense, the present invention encompasses compositions, methods of making such compositions, and methods for their use in the prevention, treatment, and/or management, of microbial or viral pathogenesis and infection. The compositions disclosed herein, as well as methods employing them, find particular use in the treatment or prevention of influenzavirus and/or bacterial pathogenesis and infection using immunogenic compositions and methods superior to conventional treatments available in the art.

The present invention also provides immunogenic compositions, as well as methods of making and using them in a variety of therapeutic and prophylactic regimens, and particularly in the treatment and prevention of viral and bacterial diseases in an animal, preferably in a mammal, such as a human.

In one aspect, the invention provides a method for eliciting an immunological response to an influenzavirus in an animal. This method involves, in an overall and general sense, administering one or more of the disclosed immunogenic compositions in an amount and for a time effective to elicit an immunological response to an influenzavirus in an animal. In one embodiment, the animal is a mammal, and in a preferred embodiment, the animal is a human.

The invention further provides a method of preventing or controlling an outbreak of viral or microbial infection (and influenza and/or bacterial infection in particular) in a selected mammalian population. The method includes at least providing an effective amount of one or more of the disclosed immunogenic or vaccine compositions to a susceptible or an at-risk member of the population, for a time sufficient to prevent the outbreak of such an infection in the general population.

In another aspect, the invention provides a method for stimulating the immune system of an individual to produce a protective immune response against a viral infection, such as an influenza infection. Such a method generally involves at least administering to the individual an immunologically-effective amount of one or more of the disclosed immunogenic compositions in an amount and for a time sufficient to stimulate the immune system of the individual. In the practice of the method, administration of the composition preferably induces a detectable amount of anti-influenza antibodies in the individual, and more preferably still, immunizes the individual against recurrent infection by the virus, or from infection of epitopically-related viruses.

In yet another embodiment, the invention provides a method for producing a protective immune response against influenza virus in a mammal in need thereof. Such a method generally includes providing to a mammal in need thereof an immunologically-effective amount of one or more of the immunogenic compositions disclosed herein under conditions and for a time sufficient to produce such a protective immune response against one or more influenza virus species, strains, or serotypes.

Likewise, the invention also provides a method of providing a therapeutic or diagnostic compound to a first cell in a mammal host. This method involves, in an overall and general sense, providing to such a mammal a therapeutically- or diagnostically-effective amount of one or more of the immunogenic compositions disclosed herein, under conditions and for a time effective to provide the compound to at least a first cell, tissue, organ, or organ system in such a mammal.

Additionally the invention also provides a method for administering a prophylactic antiviral or antimicrobial composition to at least a first cell, tissue, organ, or organ system in a mammal that generally involves providing to such a mammal a prophylactically-effective amount of at least a first immunogenic composition as disclosed herein.

Certain embodiments of the present invention relate to an immunogenic composition including a target antigen having one or more repeated peptide sequences, or fragments, variants, or derivatives of such peptide sequences (hereinafter interchangeably referred to as a "peptide," "sequence," "protein," or "amino acid sequence"), that are conserved across a plurality of proteins in the same, or different, virion(s), viruses, or viral particles. The sequence may be conserved within subtypes of the same virus type or within different virus types at the same time. Preferably, the viruses are Influenzaviruses. In one preferred embodiment wherein the peptide sequence is conserved within different influenzavirus particles, the virus particles may be different influenza subtypes (e.g., influenza viruses with varying HA or NA compositions, such as H1N1, H5N1, H3N2, and H2N2). For example, a selected sequence in the M1 and M2 proteins of the H5N1 influenza virus may correspond to the M1 and M2 proteins found in other H5N1 particles, and may correspond to the same sequence in the M1 and M2 proteins of the H3N2 influenza virus. In addition, while HA and NA proteins may have highly variable regions, conserved sequences from HA and NA are found across more than one influenza strain or more than one subtype (e.g., HA and NA sequences are conserved across H5N1 and H1N1). In a preferred embodiment, the conserved sequence is present among variants, or strains (viral isolates expressing substantially the same HA and NA proteins, but wherein the HA and NA protein amino acid sequences show some minor drift), of a single influenzavirus subtype and more preferably across at least two influenzavirus subtypes, e.g., subtypes of influenza A virus.

In another embodiment, the present invention encompasses an immunogenic peptide or polypeptide that includes at least one epitopic antigen, which comprises one or more repeatedly occurring peptide sequences, each of which is conserved across a plurality of homologous proteins that is conserved in a population of influenzavirus strains or serotypes, and a pharmaceutically acceptable carrier. In exemplary antigenic peptides, at least one epitopic sequence is repeated at least once, preferably at least twice times, more preferably at least three times. In other embodiments, the at least one epitopic sequence is repeated four or more times. Preferably, the peptide sequences are identical with peptide sequences in the homologous protein subunits of at least two circulating viral isolates. In each embodiment of the entire disclosure, the compositions may include a pharmaceutically acceptable carrier.

In certain preferred embodiments, the peptide sequences include peptides sequences derived from genome (i.e., RNA) segment 7 of the influenza virus, while in a more preferred embodiment, the peptide sequences include at least portions of the M1 and M2 proteins. In an exemplary embodiment, the peptide sequence is MSLLTEVETPIRNE (SEQ ID NO:32).

In other preferred embodiments, the peptide sequences include peptide sequences expressed from genome segments encoding the HA or NA proteins. Such sequences are expected to be less affected by subtype drift. Antigenic compositions including NA or HA-specific epitopic sequences include, but are not limited to, those amino acid sequences comprising, consisting essentially of, or alternatively, consisting of, an amino acid sequence selected from GNLIAP (SEQ ID NO:6); GNFIAP (SEQ ID NO:4); GNLFIAP (SEQ ID NO:5), FVIREPFISCSHLEC (SEQ ID NO:3), HYEECSCY (SEQ ID NO:7) and DWSGYSGSFVQHPELTGLD (SEQ ID NO:1), or one or more peptide sequences that are substantially homologous to any one of such sequences, or any combination thereof. Such compositions may also further optionally include one or more additional antigenic compositions as presented above and elsewhere in this application, including, for example, the epitopic sequences identified in the figures and examples, below.

In some embodiments, the target antigen includes one or more T-cell stimulating epitopes, such as diphtheria toxoid, tetanus toxoid, a polysaccharide, a lipoprotein, or a derivative or any combination thereof (including fragments or variants thereof). Typically, the at least one repeated peptide sequence of the target antigen is contained within the same molecule as the T-cell stimulating epitopes. In the case of protein-based T-cell stimulating epitopes, the at least one repeated peptide sequence of the target antigen may be contained within the same polypeptide as the T-cell stimulating epitopes, may be conjugated thereto, or may be associated in other ways. Preferably, at least one repeated peptide sequence is incorporated within or alongside the one or more T-cell stimulating epitopes in a polypeptide.

In some embodiments, the target antigens, with or without associated T-cell stimulating epitopes may include one or more polysaccharides or portions thereof. In some embodiments, at least one peptide sequence of a target antigen is conjugated to one or more polysaccharides. In other embodiments, one or more polysaccharides are conjugated to other portions of the target antigen. Certain embodiments of the present invention are selected from polysaccharide vaccines, protein-polysaccharide conjugate vaccines, or combinations thereof.

In addition, the target antigens can be used with any adjuvant or particle and can be located on the surface of any particle according to the invention. The particle may be a microbe (such as a virus, incomplete virus, or bacterium, e.g., *Bacillus* Calmette-Guérin (BCG) or microbial component, or it may be an inorganic solid (e.g., latex or glass beads, microspheres, nanospheres, microparticles, nanoparticles, ballistic particles, quantum dots, and the like) or an organic system (e.g., liposomes).

Even further, the target antigens may be located on the surface of a host cell. In preferred embodiments, this occurs via introduction of target-antigen-encoding genetic material into the host cell by a vector, such as a microbe or virus (e.g., BCG, adenovirus, adeno-associated virus, baculovirus, vaccinia virus, herpesvirus, influenzavirus, modified Vaccinia Ankara (MVA) virus, and the like) or accelerated particle transfection, with subsequent expression of the target antigen at the cell surface. The target-antigen-encoding genetic material need not be, and preferably is not, incorporated into the host cell genome.

The invention further encompasses methods of artificially synthesizing a target antigen of the present invention by in vitro chemical synthesis, solid-phase protein synthesis, in vitro (cell-free) protein translation, recombinant protein synthesis, or any combination thereof. Target antigen may be expressed in and obtained from various cell types, including bacteria, fungi, insect, mammalian, yeast, and the like, or any combination thereof.

A target antigen includes at least one of the following elements: at least one repeated peptide sequence; at least one T-cell epitope; at least one polysaccharide; at least one polynucleotide; at least one structural component; or a combination thereof. The at least one structural component may include one or more of: at least one linker segment; at least one sugar-binding moiety; at least one nucleotide-binding moiety; at least one protein-binding moiety; at least one enzymatic moiety; or a combination thereof.

Even further, the invention encompasses methods of preparing an immunogenic composition, preferably a pharmaceutical composition, more preferably a vaccine, wherein a target antigen of the present invention is associated with a pharmaceutically acceptable diluent, excipient, or carrier.

The present invention further includes methods for inducing a detectable immune response against a microbe in a subject. One preferred method includes administering to a subject in need thereof an amount of a vaccine sufficient to induce a detectable immune response, which vaccine includes one or more target antigens of the present invention. Preferably, the target antigen comprises one or more repeatedly occurring peptide sequences, each of which is conserved across a plurality of homologous proteins in a plurality of microbial particles, e.g., virus particles having homologous proteins containing antigens. Preferably, the method further includes administering the target antigens in association with a pharmaceutically acceptable carrier and evaluating the subject to detect the immune response.

In some embodiments, the invention encompasses methods of vaccinating a subject against Influenza that includes administering to a patient in need of influenza vaccination a therapeutically or prophylactically effective amount of an influenza vaccine, which influenza vaccine includes a target antigen comprising one or more repeatedly occurring peptide sequences, each of which is conserved across a plurality of homologous proteins in a plurality of influenza virus particles, and a pharmaceutically acceptable carrier, to provide a detectable immune response in the patient against influenza.

The present invention provides methods and immunogenic compositions for prophylaxis, treatment, and management in hosts of microbial disease or infection and the symptoms thereof. In some embodiments, microbial disease or infection includes that of viral origin and, in particular embodiments, that caused by infection by influenza virus. In other embodiments, the microbial disease or infection includes that of bacterial origin and, in particular embodiments, that caused by infection by pneumococcus.

The present invention also provides immune-stimulating target antigens including at least portions of one or more protein or protein subunit polypeptides having amino acid sequences or fragments, or variants or derivatives thereof, which are identical, nearly identical, highly conserved, or conserved in amino acid sequence with at least portions of homologous proteins, or protein subunits, found within a plurality of microbial particles. Preferably, the homologous proteins or protein subunits are found within wild-type microbial particles, or populations of wild-type microbial particles, although in some embodiments the microbial particles may be engineered, cultured, or intentionally mutated, or any combination thereof. The homologous proteins or protein subunits, whether or not wild-type, are collectively referred to as "selected polypeptides." The selected polypeptides are preferably characterized by the invariant, near-invariant, or substantially highly homologous, or conservation of at least portions of their amino acid sequence within homologous protein subunits across a plurality of different microbial particles. The invariant, near-invariant, highly conserved, or conserved portions of the selected polypeptides' amino acid sequences are referred to collectively herein as "peptide sequences."

The immune-stimulating target antigens and antigenic compositions that include them are preferably used in the preparation of a vaccine, preferably as components of a vaccine. The vaccines of the present invention provide immunogenic epitopes that induce immunity through a humoral (B-cell) or a cell-mediated (T-cell) immune response, or both, in the host. It is believed that the inventive immune-stimulating target antigens used in a vaccine will confer enhanced immunogenic response in vivo when compared with corresponding conventional vaccines. Without being bound by theory, it is believed that the immunogenic response to conserved viral (microbial) epitopes raised by the inventive vaccine is enhanced, compared with conventional vaccines, through the efficient presentation of the immunogenic epitopes (peptide sequences, polysaccharides, etc.) to the host immune system. The immunogenic potential of the target antigen can also be enhanced by repeating all or a portion of the conserved immunogenic sequence(s) one or more times in the vaccine. The nature of the repeated sequences of the target antigens of the present invention may result in nucleotide or amino acid sequences that are unique from any naturally-occurring nucleotide or peptide sequence of the source microbe(s).

In accordance with some embodiments of the present invention, a vaccine can be based on one or more conserved antigenic peptide sequences common to at least a plurality of strains, and preferably to a plurality of subtypes of a given type of virus. Preferably, the invention in such embodiments preferably provides a vaccine based on a conserved influenza antigen common to all strains of a given influenza type or subtype, even more preferably all strains of influenza A virus. Such vaccines of the present invention may provide therapeutic and/or prophylactic benefits, including single course of inoculation, cross-protection against new strains in a highly divergent population of viruses, and protection over the course of years (or a period longer in duration than conventional vaccines).

The present invention also provides a composition for use in the prophylaxis of a viral or microbial disease, as well as a composition for use in the therapy or diagnosis of such a disease. The invention also provides for the use of one or more of the disclosed immunogenic compositions in the manufacture of a medicament for prophylaxis or therapy, and particularly for use in the manufacture of a medicament for treating, and/or preventing one or more diseases, or one or more symptoms thereof, in a mammal, and in a human in particular.

The use of one or more of the disclosed immunogenic compositions in the manufacture of a medicament for prophylaxis or therapy of one or more medical conditions, including for example, a viral or a microbial infection in a human is also an important aspect of the invention. Formulation of such compositions for use in administration to an animal host cell, and to a mammalian host cell in particular, is also provided by the invention. In particular embodiments, the invention provides for formulation of such compositions for use in administration to a human, or to one or more selected human host cells, tissues, organs in situ, or to an in vitro or ex situ culture thereof.

The present invention also provides for the use of one or more of the disclosed immunogenic compositions in the manufacture of a medicament or a vaccine for the prophylaxis or prevention of disease, including, in the preparation of one or more vaccines suitable for prophylactic administration to prevent or ameliorate one or more symptoms of a microbial or viral infection, including, for example, influenza and bacterial infections in particular.

The invention also provides methods for providing a therapeutic or prophylactic immunogenic compound to a first cell in a mammal, with the method generally including providing to a mammal in need thereof, an effective amount of an immunogenic composition as disclosed herein that includes at least one therapeutic or prophylactic active ingredient, and for a time effective to provide the desired therapy and/or prophylaxis in the selected mammal.

In certain aspects of the invention, the invention provides immunogenic compositions suitable for administration to one or more host cells. In particular embodiments, the host cell is a mammalian host cell, while in others it is a human cell. In other preferred aspects, the host cell is included within the body of a human, or included within at least a first ex vivo tissue or plurality of cells that are compatible for implantation into the body of such a human as part of a typical ex vivo therapy protocol or such like.

In some embodiments, the present invention provides immunogenic compositions including antigenic peptides and polypeptides, which are composed of epitopes that are conserved across a population of different influenza strains or serotypes. As used herein, the term "conserved across viral (influenza) strains" refers to an identical, similar or homologous chemical compound among some, preferably most, and most preferably substantially all influenza A viral serotypes and/or strains having a common serotype. For example, randomly chosen virus particles from a population of influenza A virus having various serotypes, such as, e.g., influenza A virus, serotype H1N1, and influenza A virus, serotype H3N2, would likely contain at least one protein, or a region thereof, that is conserved across a plurality of unique influenza A viral strains. Influenza strains typically refer to virus isolates that may vary somewhat (e.g., they have drifted) and may express HA and/or NA proteins, but with slightly different HA or NA primary amino acid sequences.

Conserved regions on NA or HA may also confer cross-subtype immunity. As an example, conserved epitopes on NA(N1) may confer enhanced immunity to H5N1 and H1N1. With respect to similar or homologous chemical compounds among influenza A subtypes and/or strains within a subtype, preferably these are at least about 80%, preferably at least about 90%, more preferably at least about 95% identical. In other embodiments, these similar or homologous compounds are at least about 96% identical, at least about 97% identical, at least about 98% identical, at least about 99% identical, and 100% identical (invariant).

The at least one peptide sequence within the target antigen, in its entirety or a portion thereof, is also preferably conserved on homologous proteins (e.g., protein subunits) of at least two viral particles, preferably influenza particles. As used in this context, the term "molecule" encompasses one or more protein or amino acid sequences found in a virus, preferably the influenza virus. As shown in FIG. 1, the proteins include, for example, expressed proteins in the virus structure, such as HA, NA, protein polymerases (PB1, PB2, PA), matrix proteins (M1, M2), and nucleoprotein ("NP"). Preferably, the conserved peptide sequences are conserved on at least two or more of the M1, M2, HA, NA, or one or more polymerase proteins, and preferably a majority or even all of the preceding.

In certain embodiments, peptide sequences are repeated consecutively. In other embodiments, the sequences are repeated although interspersed among subsequences or other peptides (e.g., spacers), whether immunogenic (e.g., T-cell inducing epitope) or non-immunogenic in nature. In yet another embodiment, there may be a conserved peptide sequence from one influenza virus protein interspersed with sequences from other influenzavirus related proteins, including, for example, M2, HA, and NA proteins. Such sequences can then be interspersed with single or repeated conserved epitopes or single or repeated T-cell inducing epitopes.

In yet another embodiment, selected peptides from unrelated microbes may be combined into a single target antigen. For example, influenza sequences (selected peptides) may be interspersed with conserved sequences or epitopes selected from other microbes, such as *S. pneumococcus* or *S. aureus*. Preferred proteins, from which preferred peptides may be selected, include PspA, PspC, HA, NA, M2e, *H. influenza* protein D, coagulase, etc.

As used herein, in some aspects, "homology" of peptide sequences is at least about 80%, preferably at least about 85%, preferably at least about 90%, preferably at least about 93%, preferably at least about 94%, preferably at least about 95%, preferably at least about 96%, preferably at least about 97%, more preferably at least about 98%, even more preferably at least about 99%, and most preferably about 100%, compared to the identified peptide sequence. The term "homology" among proteins is generally concluded based on sequence similarity. In other aspects, protein sequence homology encompasses proteins providing the same function and/or having the same antibody receptor or conjugation functionality as the identified peptide sequence.

In the present invention, any combination or multiples of highly conserved epitopic peptide sequences may be utilized in the formulation of antigenic peptides, polypeptides, and vaccines to provide one or more desired immunogenic characteristics. It is therefore within the scope of this invention to incorporate all sequences of conserved regions of homologous microbial or viral proteins, subunits, homologs, and such like.

For example, viral proteins homologous across subtypes, such as influenza M1 and M2, influenza H1 and H2, influenza N2 and N3, influenza H5 and H1, or the like, are encompassed. Likewise, viral proteins homologous across strains of the same subtype, or isolates of a strain, or any combination of the aforementioned, are also encompassed within the present invention.

The present invention can be adapted to include highly variant aspects of the flu virus, thereby providing a more diverse prophylaxis against the virus. In some embodiments, the immunogenic compositions incorporate immunogenic activities against HA proteins, NA proteins, or preferably both. More specifically, the compositions and methods of administering the compositions include antigens that are typically conserved across influenza subtypes preferably epitopes from M2, HA, or NA influenza A proteins.

In some embodiments, when relevant, as would be understood by one of ordinary skill in the art, the immunogenic compositions and vaccines of the present invention can include administration of a single dose to an animal, or alternatively, can include administration of multiple, and/or successive doses to the animal over time. Alternatively, the immunogenic compositions and vaccines of the present invention may also be co-administered with one or more anti-viral compositions and/or one or more distinct immunogens or vaccine formulations.

The dosage of the vaccine will depend on the age of the person to be vaccinated, as well as the person's weight, sex and medical condition of the subject and the route of administration, the desired effect; and the particular conjugate employed (e.g., the peptide, the peptide loading on the carrier, etc.), and those of ordinary skill in the art will be readily able to adjust the dosage as needed based on these and other conventional dosing factors.

The vaccines and immunogenic compositions of the invention may be administered to a selected animal using any of a number of conventional methodologies, including for example, but not limited to, parenteral, intravenous, intraperitoneal, subcutaneous, transcutaneous, intradermal, subdermal, transdermal, intramuscular, topical, intranasal, or other suitable route, including, but not limited to, administration, by injection, inhalation, insufflation, or ingestion.

Yet another advantage of the present invention may include immunogenic compositions that may supplement the prophylactic or therapeutic effect(s) of conventional vaccines such as the flu vaccine, and therefore the immunogenic compound may be administered in association with one or more conventional vaccines to enhance immunity against the influenzavirus or a pathogenic microbe. More specifically, the immunogenic compositions of the invention may be administered as a booster to, or as a comprehensive regimen with, one or more conventional vaccines including, for example, but not limited to, conventional influenzavirus vaccines.

The immunogenic compositions and vaccines of the present invention may be provided alone, for example, as the primary anti-microbial vaccine. In certain preferred embodiments of the present invention, the immunogenic compositions and vaccines are utilized in prime boost fashion, particularly if the immune response induced by a single dose of an inactivated vaccine is not sufficiently strong or sustained to provide a desired level of protection. The immunogenic compositions and vaccines of the invention therefore are configured and adapted to protect against microbial types, such as influenza strains, that are present in the priming vaccine and preferably also would enhance cross-protection to other microbes, such as other influenza subtypes or types. Without being bound by theory, it is believed that this occurs by driving immune responses to conserved epitopes, thereby providing additional protection against influenza drift and/or shift. Boosting typically involves repeated administration to enhance the immune response to a vaccine antigen. The "prime-boost" approach is the administration of the same antigen in two different vectors, e.g., given successively. In this approach, exposure to the antigen in the first vector "primes" the immune response; re-exposure to the same antigen in the second vector "boosts" the response.). This approach has also been termed "heterologous boosting" to distinguish it from the traditional method of homologous boosting in which two or more doses of the same vaccine are given successively by the same vector.

In preferred boosting administration, the two-stage vaccine-delivery program is used to drive powerful cell-based immune responses (those based on T-cells, as opposed to B-cell-based antibody responses). In certain embodiments, the prime-boost technique includes a DNA vaccine, such as a variant of a flu vaccine, e.g., a conventional influenza vaccine offered annually, for the priming phase and a virus-based approach for the boost. Prime boost strategies are well known and explained, for example, in Schneider et al., 2002; Gonzalo et al., 2002; Tanghe, 2001; and U.S. Pat. No. 6,500,432 (each of which is specifically incorporated herein in its entirety by express reference thereto).

Antigens and vaccines of the invention can also optionally be formulated with one or more other vaccines or antigenic compositions to yield "combination" or "multivalent" compositions and vaccines as is known to those of ordinary skill in the art. One can then inoculate a patient with the combination vaccine either sequentially or concurrently to generate an immune response against the conserved influenza, as well as the other antigens in the combination vaccines.

Another important aspect of the present invention concerns methods for using the disclosed immunogenic compositions to deliver one or more therapeutic agents for treating or ameliorating one or more symptom(s) of an infection or disease in a mammal. Such methods generally involve administration to a mammal, and in particular, to a human, in need thereof, one or more of the disclosed immunogenic compositions, in an amount and for a time sufficient to treat, ameliorate, or lessen the severity, duration, or extent of, such a disease or infection in such a mammal.

The methods and compositions of the invention may also be used in prevention, prophylaxis, and/or vaccination of an animal that has, is suspected of having, is at risk for developing, or has been diagnosed with one or more infections and/or diseases, either before, during, or after diagnosis or the onset of one or more clinical symptoms of the disease, or one or more symptoms thereof.

Immunogenic Compositions

In one embodiment, the invention provides a method of generating an immune or a T-cell response in an animal, and in particular in a mammal, preferably a human. The method concerns in a general sense the administration of at least a first immunogenic composition to the animal that comprises at least a first isolated peptide, or at least a first nucleic acid segment that encodes such a peptide, wherein the peptide comprises a first contiguous amino acid sequence according to any one of SEQ ID NO:1 to SEQ ID NO:52, and more particularly, a contiguous amino acid sequence according to any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, or SEQ ID NO:52 being particularly preferred.

The invention encompasses immunogenic peptides and polypeptides that may be of any intermediate length in the preferred ranges, such as for example, those peptides of about 75, about 70, about 65, about 50, about 55, about 50, about 45, about 40, about 35, about 30, about 25, about 20, or even about 15 amino acids or so in length, as well as those peptides having intermediate lengths including all integers within these ranges (e.g., alternatively, the peptides may be about 79, about 78, about 77, about 76, about 74, about 73, about 72, about 71, etc. amino acids in length). In particular embodiments, when smaller peptides are preferred, the length of the peptide may be 9, or about 10, about 11, about 12, about 13, about 14, about 15, about 16, about 17, about 18, about 19, or even about 20 or so amino acids in length, so long as the peptide comprises at least a first contiguous amino acid sequence according to any one of SEQ ID NO:1 to SEQ ID NO:52.

A single immunogenic peptide or polypeptide may contain only one of the contiguous amino acid sequences disclosed herein, or alternatively, a single peptide may comprise a plurality of contiguous amino acid sequences according to any one of SEQ ID NO:1 to SEQ ID NO:52. In fact, the peptide may comprise a plurality of the same contiguous amino acid sequences, or they may comprise one or more different contiguous amino acid sequences disclosed in SEQ ID NO:1 to SEQ ID NO:52. For example, a single peptide of from 9 to about 50 amino acids in length could comprise a single epitopic peptide disclosed herein, or could comprise 2, 3, 4, or even 5 distinct epitopic sequences as disclosed in any of SEQ ID NO:1 to SEQ ID NO:52. Alternatively, a single peptide of from 9 to about 50 amino acids in length could comprise 2, 3, 4, or even 5 identical epitopic sequences as disclosed in any one of SEQ ID NO:1 to SEQ ID NO:52.

In one exemplary embodiment, the peptide composition comprises at least a first isolated immunogenic peptide of from 9 to about 80 amino acids in length, or at least a first nucleic acid segment that encodes such an immunogenic peptide; wherein the peptide comprises at least two or more contiguous amino acid sequences selected from the group consisting of any one of SEQ ID NO:1 to SEQ ID NO:52.

In addition to antigenic peptides and polypeptides that comprise a single peptide epitope, the invention also concerns polypeptide compositions that comprise 3, 4, 5, 6, or more antigenic peptide epitopes and/or the polynucleotides that encode such multivalent immunogenic peptide compositions. Compositions comprising such pluralities of peptide epitopic species are particularly desirable in the formulation of therapeutic agents that comprise pluralities of antigens having: (a) two or more different contiguous amino acid sequences as disclosed in the amino acid sequences of SEQ ID NO:1 to SEQ ID NO:52 and/or a plurality of polynucleotides that encode such immunogenic peptide compositions; or (b) two or more multiples of at least a first epitopic or antigenic sequence that comprises, consists essentially of, or alternatively, consists of, an amino acid sequences according to any one or more of SEQ ID NO:1 to SEQ ID NO:52 and/or a plurality of polynucleotides that encode such antigenic peptides. Irrespective of the source of the particular antigenic peptide and polynucleotide compounds, the invention particularly contemplates the use of one, two, three or four distinct peptides, polynucleotides or derivatives thereof, up to and including a plurality of such compounds.

The additional peptides in such compositions may all be of approximately the same size and/or approximately the same primary amino acid sequence, or alternatively, the peptides may differ considerably in length and/or primary amino acid sequence. Such compositions may further comprise one or more additional components, such as for example, a pharmaceutically acceptable excipient, buffer, or reagent as described in detail hereinbelow. Such compositions may also optionally further comprise at least a first immunostimulant or at least a first adjuvant as described herein. Such immunostimulants and adjuvants preferentially enhance a T-cell response in a human, and may preferably include montanide, a cytokine, Ribi adjuvant, saponin, a microfluidized adjuvant, an immune stimulating complex, an inactivated toxin, or any combination thereof. As described in more detail hereinbelow, the compositions may be formulated for diagnostic or therapeutic uses, including their incorporation into one or more diagnostic, therapeutic, or prophylactic kits for clinical packaging and/or commercial resale, with those formulations suitable for administration to a mammal, such as a human, through any suitable route of administration but with parenteral, intravenous, intraperitoneal, subcutaneous, intranasal, transdermal, and oral routes being particularly preferred.

The compositions may further optionally comprise one or more detection reagents, one or more additional diagnostic reagents, one or more control reagents, and/or one or more therapeutic reagents. In the case of diagnostic reagents, the compositions may further optionally comprise one or more detectable labels that may be used in both in vitro and/or in vivo diagnostic, therapeutic, and prophylactic methodologies.

As noted above, the peptides of the present invention may comprise one or more variants of the amino acid sequences as disclosed herein. A peptide "variant," as used herein, is a peptide that differs from a particular primary amino acid sequence in one or more substitutions, deletions, additions and/or insertions, such that the immunogenicity of the peptide is substantially retained (i.e., the ability of the variant to react with antigen-specific antisera and/or T-cell lines or clones is not substantially diminished relative to the native peptide). In other words, the ability of a variant to react with antigen-specific antisera and/or T-cell lines or clones may be enhanced or unchanged, relative to the peptide from which the variant was derived.

Preferably, the biological activity of a peptide variant will not be diminished by more than about 1%, and preferably still will not be diminished by more than about 2%, relative to the biological activity of the unmodified peptide. More preferably, the biological activity of a peptide variant will not be diminished by more than about 3%, and more preferably still will not be diminished by more than about any of 4%, 5%, 6%, 7%, 8%, or 9%, relative to the biological activity of the unmodified peptide. More preferably still, the biological activity of a peptide variant will not be diminished by more than 10%, and more preferably still, will not be diminished by more than about any of 11%, 12%, 13%, 14%, 15%, 16%, 17%, 18%, 19%, or 20% relative to the biological activity of the corresponding unmodified peptide.

Based upon % sequence homology, preferred peptide variant of the present invention include those peptides that are from 9 to about 100 amino acids in length, and that comprise at least a first sequence region that is at least 75% identical to at least one of the amino acid sequences disclosed in any one of SEQ ID NO:1 through SEQ ID NO:52, and more preferably those that comprise at least a first sequence region that is at least 80%, more preferably at least 85%, and even more preferably at least 90%, identical to at least one of the amino acid sequences disclosed in any one of SEQ ID NO:1 through SEQ ID NO:52. Particularly preferred peptide variants of the present invention are those peptides that comprise at least a first sequence region that is at least 91%, 92%, 93%, 94%, 95% 96%, 97%, 98%, or 99% identical to at least one of the amino acid sequences disclosed in any one of SEQ ID NO:1 through SEQ ID NO:52.

Such peptide variants may typically be prepared by modifying one of the peptide sequences disclosed herein, and particularly by modifying the primary amino acid sequence of one or more of the peptide epitopes disclosed in any one of SEQ ID NO:1 through SEQ ID NO:52. These biological functional equivalent peptides may encompass primary amino acid sequences that differ from the original peptide sequences disclosed in any one of SEQ ID NO:1 through SEQ ID NO:52 by one or more conservative amino acid substitutions.

It has been found, within the context of the present invention, that a relatively small number of conservative or neutral substitutions (e.g., 1 or 2) may be made within the sequence of the peptide epitopes disclosed herein, without substantially altering the biological activity of the peptide. In some cases, the substitution of one or more amino acids in a particular peptide may enhance or otherwise improve the ability of the peptide to elicit an immune or T-cell response in an animal that has been provided with a composition that comprises the modified peptide, or a polynucleotide that encodes the peptide. Suitable substitutions may generally be identified by using computer programs, as described hereinbelow, and the effect of such substitutions may be confirmed based on the reactivity of the modified peptide with antisera and/or T-cells as described herein. Accordingly, within certain preferred embodiments, a peptide for use in the disclosed diagnostic and therapeutic methods may comprise a primary amino acid sequence in which one or two or more amino acid residues (depending on the length) are either eliminated or substituted by one or two or more replacement amino acids, such that the ability of the modified peptide to react with antigen-specific antisera and/or T-cell lines or clones is not significantly less than that for the unmodified peptide. Exemplary such substitutions may preferably be located within one or more MHC binding sites on the peptide.

As described above, preferred peptide variants are those that contain one or two or more conservative substitutions. A "conservative substitution" is one in which an amino acid is substituted for another amino acid that has similar properties, such that one of ordinary skill in the art of peptide chemistry would expect the secondary structure and hydropathic nature of the peptide to be substantially unchanged based on the guidance provided herein. Amino acid substitutions may generally be made on the basis of similarity in polarity, charge, solubility, hydro-phobicity, hydrophilicity, the amphipathic nature of the residues, or any combination thereof. For example, negatively charged amino acids include without limitation aspartic acid and glutamic acid; positively charged amino acids include without limitation lysine and arginine; and amino acids with uncharged polar head groups having similar hydrophilicity values include without limitation leucine, isoleucine and valine; glycine and alanine; asparagine and glutamine; and serine, threonine, phenylalanine and tyrosine. Examples of amino acid substitutions that represent a conservative change include: (1) replacement of one or more Ala, Pro, Gly, Glu, Asp, Gln, Asn, Ser, or Thr; residues with one or more residues from the same group; (2) replacement of one or more Cys, Ser, Tyr, or Thr residues with one or more residues from the same group; (3) replacement of one or more Val, Ile, Leu, Met, Ala, or Phe residues with one or more residues from the same group; (4) replacement of one or more Lys, Arg, or His residues with one or more residues from the same group; and (5) replacement of one or more Phe, Tyr, Trp, or His residues with one or more residues from the same group.

A variant may also, or alternatively, contain non-conservative changes, for example, by substituting one of the amino acid residues from group (1) with an amino acid residue from group (2), group (3), group (4), or group (5). Variants may also (or alternatively) be modified by, for example, the deletion or addition of amino acids that have minimal influence on the immunogenicity, secondary structure and hydropathic nature of the peptide.

Therapeutic and Prophylactic Kits

Kits including one or more of the disclosed immunogenic compositions or pharmaceutical formulations including such; and instructions for using the kit in a therapeutic, prophylactic, and/or other clinical embodiment(s) also represent preferred aspects of the present disclosure. Such kits may include one or more of the disclosed immunogenic compositions and vaccines, either alone, or in combination with one or more additional therapeutic compounds, pharmaceuticals, and such like. The kits according to the invention may be packaged for commercial distribution, and may further optionally include one or more delivery devices for the composition(s) to an animal (e.g., syringes, injectables, or such like). Such kits may be therapeutic kits for treating, preventing, or ameliorating an infection or disease, or the symptoms thereof, and may include instructions for using the kit in a therapeutic, prophylactic or diagnostic medical regimen or protocol.

The container(s) for such kits may typically include at least one vial, test tube, flask, bottle, syringe or other container, into which the immunogenic peptide or vaccine composition(s) may be placed, and, preferably, suitably aliquotted for administration to an animal. Where a second immunogenic composition or a first antiviral or antimicrobial compound is also desired, the kit may also contain the second immunogenic composition or the first antiviral or antimicrobial compound in a second distinct container, or a single container with a breakable or non-breakable barrier to isolate the two components. Alternatively, a plurality of distinct immunogenic composition(s) and/or distinct antiviral or antimicrobial compound(s) may be prepared in a single formulation, and may be packaged in a single container, vial, flask, syringe, catheter, cannula, bottle, test tube, ampoule, or other suitable container. The kit may also include a larger container, such as a case, that includes the containers noted above, along with other equipment, instructions, and the like.

Compositions for Use in the Preparation of Medicaments

Another important aspect of the present invention concerns methods for using the disclosed immunogenic compositions (as well as formulations including them) in the preparation of medicaments for preventing, treating or ameliorating a disease, or the symptoms thereof, in an animal, such as a vertebrate mammal. Use of the disclosed immunogenic compositions is also contemplated in therapy and/or prophylaxis of one or more diseases of microbial or viral origin.

Such use generally involves administration to an animal in need thereof one or more of the disclosed immunogenic compositions in an amount and for a time sufficient to prevent, treat, or manage one or more diseases or symptoms thereof in the affected animal. Compositions including one or more of the disclosed immunogenic formulations also form part of the present invention, and particularly those compositions that further include at least a first pharmaceutically-acceptable excipient for use in the therapy or prophylaxis of one or more diseases of microbial or viral origin.

The immunogenic compositions of the present invention can be formulated as univalent (i.e., monovalent), or alternatively, as bivalent, trivalent or even multivalent (i.e., polyvalent) immunogens or vaccines. A monovalent immunogen will preferably include a single antigenic peptide or polypeptide of the present invention (or a polynucleotide that encodes and is capable of expressing such an antigenic peptide or polypeptide) that is capable of eliciting an immune response when introduced into the body of a mammal. Alternatively, the monovalent immunogenic composition may include a fragment, variant, or derivative of an antigenic peptide or polypeptide that is capable of eliciting an immune response in a mammal, or a polynucleotide that encodes and is capable of expressing such an antigenic fragment, variant, or derivative, and thereby eliciting such an immune response, in such a mammal.

A bivalent immunogen or vaccine composition will preferably include (either in polypeptide antigen form, or as a polynucleotide encoding, and capable of expressing such an antigenic polypeptide) two different influenzavirus- or microbially-derived antigenic polypeptides, fragments, variants, or derivatives thereof, each being capable of eliciting an immune response in a mammal. A trivalent or further polyvalent immunogenic composition or vaccine will include three or more antigenic peptides, respectively (or peptide epitopes or fragments, variants or derivatives thereof), either in isolated form, or as encoded by one or more polynucleotides of the invention. Such multivalent compositions may include individual epitopic peptides, or alternatively may include a single polypeptide sequence that includes two or more epitopic peptide sequences within the primary amino acid sequence of the polypeptide.

The polynucleotides of the invention may be formulated alone, or may optionally further include a suitable vector for administration to, and preferably, expression in, a mammal host. Such a vector may optionally include one or more suitable promoter(s), enhancer(s), post-transcriptional or post-translational regulatory element(s), and such like (or any desired combination of two or more of such elements), to facilitate expression of the polynucleotide in a mammalian host cell, and translation of the encoded immunogenic peptide or polypeptide sequence in an amount and for a time sufficient to induce an immune response in such a mammal.

BRIEF DESCRIPTION OF THE DRAWINGS

For promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2 shows an overview of certain peptide sequences found within the M2 and M1 proteins of the influenzavirus particle as well as in other influenza viral proteins, in accordance with certain embodiments of the present invention;

FIG. 7 shows a description of exemplary NA epitopes according to the present invention;

FIG. 9 shows a view of the presentation of a preferred HA epitope on the HA polypeptide. Conserved H1, H3, H5 HA epitopes were aligned by primary amino acid sequence using 75 H1 and H3 influenza A virus field strains and several representative H5 strains available in the scientific literature. H3 and H1 vaccine and reference strains, as well as H5 peptides representing clades 1, 1', 2 and 3 were also included. The 3-D/Wisconsin/67/2005H3N2 2007/08 vaccine strain was predicted based on the nearest homolog available in the protein sequencing database using the Swiss PDF Viewer. Conserved residues observed in sequence alignments are depicted in the mature HA protein.

FIG. 10A is the ELISA for H2N2 Plate, at day 0, 28, and 42 for animal groups 1 to 7; while FIG. 10B is the ELISA for the H1N1 Plate at day 0, 28 and 42 for animal groups 1 to 7. The animal groups shown correspond to those given in the Examples and in the legend to FIG. 5;

FIG. 26A, FIG. 26B, and FIG. 26C show multiple amino acid sequence alignments of influenza A subtypes: H1 (FIG. 26A), H3 (FIG. 26B) and H5 (FIG. 26C) virus strains depicting the highly conserved GNL(P)IAP epitopic peptide region of the proteins. Representative reference and vaccine strains across several years are shown for each subtype. Asterisk (*) depicts current and previous influenza vaccine strains.

DESCRIPTION OF ILLUSTRATIVE EMBODIMENTS

Figure 1:
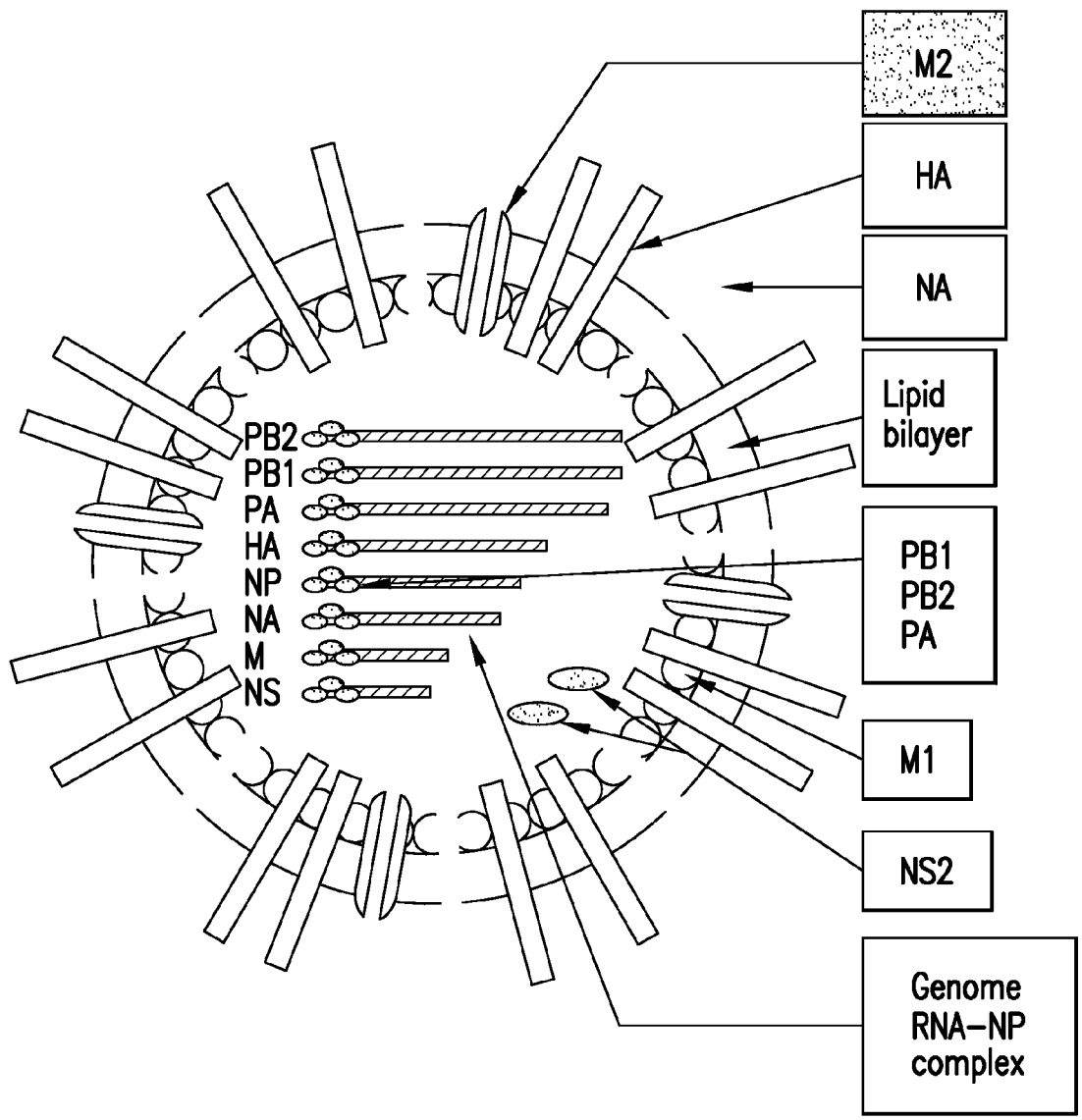
FIG. 1 is a generic depiction of the Influenza viral particle, in which the M2, HA and NA proteins are shown on the surface of the molecule, in accordance with certain embodiments of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

The present invention provides numerous advantages over the prior art. While applicable to all kinds and combinations of microbes, including viruses, the following advantages, techniques, and examples are generally discussed herein with reference to Influenza. Unlike the conventional flu vaccine, which has an effectiveness that is highly strain-specific and therefore limited, the present invention induces immunity across influenza types, subtypes, and strains even as they shift or drift. In contrast to conventional vaccines, which must be produced annually to combat specific flu strains and typically are not used year-to-year, the present invention is generally applicable to provide immunity protection against influenza for longer periods or periodically as a booster. As used herein, it should be understood that providing or inducing immunity also includes increasing pre-existing immunity from conventional vaccines or natural immunity. Because the present inventive vaccine includes epitopic sequences from conserved, highly conserved, near-invariant, or invariant amino acid sequence peptides of the influenza virus, the need for annual strain-specific reformulation is removed. By incorporating conserved epitopes from different microbial proteins (e.g., in the case of influenza, epitopes from M2, HA, and NA, etc.), the immune response may be broadened across multiple distinct antigenic loci of a microbe, thus decreasing the likelihood that the microbe will successfully mutate to avoid the immune response raised by the administered vaccine.

Studies in mice have shown that monoclonal antibodies to naturally-occurring polypeptide sequences native to the matrix protein 2 ectodomain ("M2e") confer immunity to multiple subtypes of Influenza A (Gemini Science, Inc., private communication). Further, peptide sequences derived from selected polypeptides of *Plasmodium falciparum* and *Plasmodium berghei* (two causative agents of human and murine malaria) synthesized collinearly by solid-phase protein synthesis (SPPS) with two universal human tetanus toxin T-cell epitopes, epitopes 830-843 and 947-967 (P2 and P30) have been found to be capable of stimulating human PBL and tetanus toxoid-specific T-cell clones (Valmori et al., 1992).

Conventional microbial vaccines usually target epitopes or antigens that are highly strain or type specific. Accordingly, conventional vaccine manufacturers must know the specific currently circulating strains or microbial types (subtypes) that must be covered in order to prepare a vaccine that will provide effective immunity against circulating microbes in a population. Studies using lipoteichoic acid (LTA) determined that antibodies to an antigen conserved across many bacteria induced generic and protective immunity against a variety of bacteria.

Because there are many strains and subtypes of influenza virus, and the vaccines currently licensed for human use focus on whole virus or viral subunits that induce immunity to some, but not all, influenza strains or subtypes, it was desirable to develop new multivalent influenza vaccines.

By identifying and selecting conserved epitopes or regions from influenza proteins within different influenza viral subtypes, selected amino acid sequences could be produced (either alone, or in combination with other influenza, or even other microbial antigens) to form multi-subtype influenza (or polymicrobial) vaccines or vaccine compositions useful in preventing infection from a number of different species with a single vaccine.

Target antigens were assembled using influenza proteins, including proteins M1, M2, PB1, PB2, PA, HA and NA. Conserved regions from the ectodomain of M2, M2e, and both HA and NA were identified.

Influenzavirus

Influenza is typically caused by infection of two genera of influenza viruses: Influenzavirus A and Influenzavirus B. The third genus of influenza viruses, Influenzavirus C, exists as a single species, influenza C virus, which causes only minor common cold-like symptoms in susceptible mammals.

Infections by influenza A virus and influenza B virus are typically initiated at the mucosal surface of the upper respiratory tract of susceptible mammals. Viral replication is primarily limited to the upper respiratory tract but can extend to the lower respiratory tract and cause bronchopneumonia, which can be fatal.

Influenza A virus, in particular, has many different serotypes. Presently, there are 16 known variations of HA and 9 known variations of NA within influenza A viruses, thus yielding 144 possible "HN" serotypes of influenza A virus based on variations within these two proteins alone. Only a small number of these combinations are believed to be circulating within susceptible populations at any given time. Once a new influenza strain or serotype emerges and spreads, the historical pattern is that it becomes established within the susceptible population and then moves around or "circulates" for many years, causing seasonal epidemics of the Flu.

Three genera of influenzaviruses currently comprise the Orthomyxoviridae Family: Influenzavirus A, Influenzavirus B, and Influenzavirus C. Each of these genera contains a single species of influenzavirus: The genus Influenzavirus A consists of a single species, influenza A virus, which includes all of the influenzavirus strains currently circulating among humans, including, for example, but not limited to, H1N1, H1N2, H2N2, H3N1, H3N2, H3N8, H5N1, H5N2, H5N3, H5N8, H5N9, H7N1, H7N2, H7N3, H7N4, H7N7, H9N2, and H10N7 serotypes.

The genus Influenzavirus B consists of a single species, influenza B virus, of which there is currently only one known serotype. Influenza B virus is almost exclusively a human pathogen, but is significantly less common and less genetically diverse than influenza A strains. Because of this limited genetic diversity, most humans acquire a certain degree of immunity to influenza B virus at an early age; however, the mutation frequency of the virus is sufficiently high enough to prevent lasting immunity by most humans, but not high enough to permit pandemic infection by influenza B virus across human populations.

The genus Influenzavirus C also consists of a single species, denoted influenza C virus, of which there is also currently only one known serotype. This serotype is known to infect both primates and porcines, and while infections of influenza C virus are rare, the resulting illness can be severe. Epidemics of influenza C virus are not uncommon in exposed populations, however, due to its rapid transmissibility in humans having close contact.

"Human influenza virus" usually refers to those influenzavirus serotypes that are transmissible among humans. There are only three known influenza A virus HN serotypes that have circulated widely among humans in recent times: H1N1, H2N2, and H3N2. Many humans have acquired at least some level of immunity to these subtypes. All Influenzaviruses, however, are known to mutate and change frequently. Influenzaviruses are known to infect waterfowl and swine and to circulate among those hosts forming a breeding ground for new subtypes and strains separate from human populations. Because many serotypes (and particularly newly-arising subtypes) have a zero or low prevalence in human populations, there is little or no natural immunity against them in human populations. Such a population is referred to as being "naïve" to such serotypes. Accordingly, Influenzaviruses are expected to adapt over time to generate one or more highly virulent strains that will infect and spread catastrophically among naïve humans, as has been widely reported in the mainstream press.

The highly-virulent influenza H5N1 subtype (publicly referred to as the "bird flu" virus), for example, has been reported as having mutated sufficiently to become transmissible from avian hosts to humans. As this subtype has been limited to infecting avian populations in the past, there is little or no legacy of infection to have generated immunity within the human population. Thus, the human population is expected to be highly susceptible to other Influenzavirus strains, e.g., H5N1.

To date, the H5N1 serotype does not appear to have mutated sufficiently to become efficiently transmitted from human to human. Nonetheless, because influenzaviruses are constantly adapting, there is concern that H5N1 virus or another virulent influenza strain or serotype will arise that will be able to infect humans and spread easily from one person to another. It has been commonly suggested that if H5N1 virus were to gain the capacity to spread easily from person to person, a worldwide outbreak of disease (i.e., pandemic) would likely begin, resulting in millions of deaths.

Annual influenza outbreaks occur as a result of "antigenic drift." Antigenic drift is caused by mutations within antigenic (i.e., immunity stimulating) portions of viral proteins within viral subtypes circulating in host populations that alter the host's ability to recognize and defend effectively against the infecting virus, even when the virus has been circulating in the community for several years. The antigenic drift that diminishes existing immunity in a host population generally occurs within so-called "immunodominant" antigens or regions. Immunodominant antigens are those antigens belonging to a pathogen that are the most-easily and most-quickly recognized by the host immune system and, consequently, account for the vast majority of immune response to the invading pathogen. Typically, immunodominant antigens exist within regions of the pathogen that are most exposed to the environment, i.e., are on the external surfaces or on protruding elements of the pathogen, and so are most readily accessible to the host immune system.

In the case of influenza, the immunodominant HA and NA proteins protrude from the central capsid of the viral particle, and so they tend to interact most strongly with the host's internal environment and dominate the host immune response. Mutations occurring in the microbial genome that protect the microbe from the host immune system, these mutations are most readily found to affect the immunodominant antigens.

Conversely, non-immunodominant antigens are those that are capable of raising a host immune response but account for only a small amount of the total immune response. This is thought to happen because the non-immunodominant antigens are at least partially shielded from the host immune system, as in the case of an antigen that is located in a cleft or fold of the microbial surface or is surrounded by protruding elements of the microbe. In the case of influenza, non-immunodominant antigens occurring near the capsid surface are shielded from the host immune system by the immunodominant HA and NA spikes protruding from the surface. Non-immunodominant antigens tend to show less mutation in response to host immune pressure than do immunodominant antigens.

Antigenic shift occurs when there is an abrupt or sudden, major change in a virus. Antigenic shift in Influenzavirus is typically caused by the occurrence of new combinations of the HA and/or NA proteins on the surface of the virus, i.e., the creation of a new Influenza subtype. The appearance of a new influenza A virus subtype, to which most of the world's population is naïve, is the first step toward a pandemic. If the new Influenza subtype also has the capacity to spread easily from person to person, then a full-blown pandemic may be expected, resulting in a global influenza outbreak infecting millions of humans.

Influenza a Viral Strains

Exemplary influenza A viral strains for which the antigenic compositions and vaccines of the present invention find particular utility may include, but are not limited to, A/Aichi/2/68, A/Alaska/6/77, A/Alice, A/Ann Arbor/6/60, A/Bayern/7/95, A/Beijing/352/89, A/Beijing/353/89, A/Bethesda/1/85, A/California/10/78, A/Chick/Germany/N/49, A/Chile/1/83, A/Denver/1/57, A/Dunedin/6/83, A/Equine/Miami/1/63, A/FM/1/47, A/Great Lakes/0389/65, A/Guizhou/54/89, A/Hong Kong/77, A/Hong Kong/8/68, A/Hong Kong/483/97, A/Johannesburg/33/94, A/Kawasaki/9/86, A/Kiev/59/79, A/Korea/1/82, A/Korea/426/68, A/Leningrad/13/57, A/Los Angeles/2/87, A/Mai/302/54, A/Memphis/8/88, A/Nanchang/933/95, A/New Jersey/8/76, A/NT/60/68, A/NWS/33, A/Peking/2/79, A/Port Chalmers/1/73, A/PR/8/34, A/Shanghai/11/87, A/Shanghai/16/89, A/Shanghai/31/80, A/Singapore/1/57, A/Singapore/6/86, A/South Carolina/1/181918, A/Swine/1976/31, A/Swine/Iowa/15/30, A/Swine/New Jersey/8/76, A/Sydney/5/97, A/Taiwan/1/86, A/Taiwan/1/86A1, A/Texas/35/91, A/Texas/36/91, A/USSR/90/77, A/Victoria/3/75, A/Vietnam/1203/04, A/Washington D.C./897/80, A/Weiss/43, A/WS/33, A/WSN/33, A/Wuhan/359/95, A/Wyoming/1/87, and A/Yamagata/32/89, as well as derivatives, variants, or homologs thereof.

Exemplary influenza B viral serotypes include, but are not limited to, B/Allen/45, B/Ann Arbor/1/86, B/Bangkok/163/90, B/Beijing/184/93, B/Brigit, B/GL/1739/54, B/Hong Kong/330/2001, B/Hong Kong/5/72, B/Lee/40, B/Maryland/1/59, B/Mass/3/66, B/Oman/16296/2001, B/Panama/45/90, B/R22 Barbara, B/R5, B/R75, B/Russia/69, B/Shandong/7/97, B/Sichuan/379/99, B/Taiwan/2/62, B/Tecumseh/63/80, B/Texas/1/84, B/Victoria/2/87, and B/Yamagata/16/88, as well as derivatives, variants, or homologs thereof.

Polynucleotide and polypeptide sequences from these strains are contained within the publicly-available databases of the National Center for Biotechnology Information (National Library of Medicine, National Institutes of Health, Bethesda, Md., USA), and viral stocks may be obtained from the American Type Culture Collection (Manassas, Va., USA), or are otherwise publicly available.

Antigenic Polypeptides

In preferred embodiments, without being bound by theory, the vaccine of the present invention targets conserved protein targets, or epitopes, of the influenza viral particle that are exposed to and are capable of interacting with the host immune system, such as the matrix protein 2 ectodomain (M2e), or various other components of the M2 and/or M1 proteins, HA and NA proteins. These epitopes generally incorporate highly conserved peptide sequences, thereby substantially excluding some, or preferably many of the non-highly-conserved HA and NA protein peptide sequence targets, or epitopes, which are subject to antigenic variation. The HA and NA proteins induce strong humoral immune responses using conventional vaccines and that are distinct from the primary epitopes of conserved segments, thus allowing influenza A virus shift or drift to avoid or minimize conventional vaccine immunity. These vaccine constructs embodying one aspect of the present invention drive immunity to the conserved epitopes.

In some embodiments, the conserved amino acid peptide sequences of the present invention are present in more than one protein subunit of a virus. For example, in certain influenza viruses, certain amino acid sequences from the M2 protein are identical to amino acid sequences in the M1 protein, such as the region of influenza generally referred to as RNA segment 7. RNA segment 7 includes the open reading frames, as would be understood to one of ordinary skill in the art, of the two matrix genes, M1 and M2, which are highly conserved among influenza virus strains. The M1 mRNA is collinear with viral RNA of the influenza virus, while the M2 mRNA is encoded by a spliced transcript. Amino acid residues 1-9 of M2e and M1 are encoded by the same nucleotides in the same reading frame and amino acid 10-23 of M2e and 239-252 of M1 in a different reading frame. The proteins encoded by these mRNAs share their initial 9 amino acids and also have a stretch of 14 amino acids in overlapping reading frames. In some embodiments, the vaccine is therefore a DNA vaccine that includes cDNA formed from RNA of the target antigen.

Figure 2:
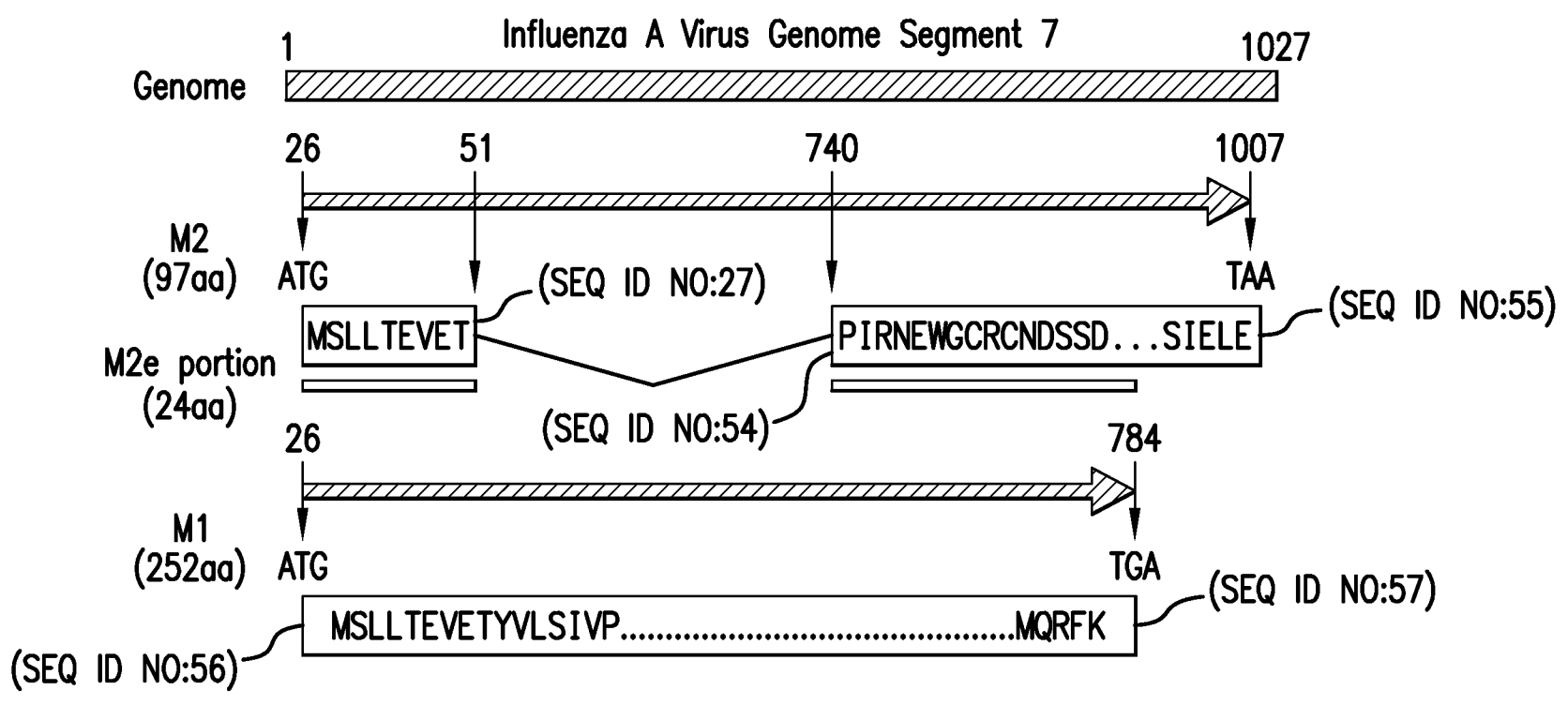

Additionally, the M1 protein is a highly conserved 252-amino-acid protein. It is the most abundant protein in the viral particle, lining the inner layer of the viral membrane and contacting the viral ribonucleoprotein (RNP) core. M1 has been shown to have several functions, including regulation of nuclear export of vRNPs, both permitting the transport of vRNP particles into the nucleus upon infection and preventing newly exported vRNP particles from reentering the nucleus. The peptide sequence SLLTEVET (SEQ ID NO:37) is conserved on the M1 protein, as shown in FIG. 2.

The 97-aa M2 protein is a homotetrameric integral membrane protein that exhibits ion-channel activity. The ion-channel activity of M2 is important both during virion uncoating and during viral budding. While the M2 protein is believed to be a relatively minor component of the influenza virion, it is abundantly expressed in infected cells during virus infection. As shown in FIG. 2, the 24 amino acid ectodomain of M2e, which is the exposed region on the surface of the influenza molecule, has the following primary amino acid sequence:

MSLLTEVETPIRNEWGCRCNDSSD.   (SEQ ID NO: 36)

The invention pertains in part to polypeptide and epitopic peptide sequences that are at least about 80% or more, at least about 85% or more, at least about 90% or more, at least about 95% or more, 97% or more, 98% or more, or 99% or more identical to one or more of the immunogenic peptide sequences disclosed herein.

The invention also concerns polynucleotide sequences that encode one or more of such peptide sequences. In such cases, it is preferable that the polynucleotide sequences are at least about 80% or more, at least about 85% or more, at least about 90% or more, at least about 95% or more, 97% or more, 98% or more, or 99% or more homologous to a polynucleotide that encodes one or more of the immunogenic peptide sequences specifically set forth herein.

In the present invention, antigenic epitopes preferably contain a sequence of at least 6 to 15, or any integer therebetween, or at least 20, or at least 25 or more contiguous amino acids of one or more of the peptide sequences disclosed herein, and particularly those as set forth in any one of SEQ ID NO:1 through SEQ ID NO:52.

Preferably, the length of the isolated amino acid sequences that comprise, consist essentially of, or alternatively, consist of, one or more epitopic sequences as disclosed herein, will be from about 8 to about 150 amino acids in length, alternatively, from about 10 to about 120 amino acids in length, from about 12 to about 100 amino acids in length, from about 14 to about 90 amino acids in length, from about 16 to about 80 amino acids in length, from about 18 to about 70 amino acids in length, from about 20 to about 60 amino acids in length, from about 22 to about 50 amino acids in length, or alternatively, from about 24 to about 40 amino acids in length.

The immunogenic peptides and polypeptides of the invention in various embodiments can be at least about any of 10, 15, 20, 25, 30, 35, 40, 45, 50, 55, 60, 65, 70, 75, 80, 85, 90, 95 amino acid residues in length; or longer, including, for example, those polypeptides of at least about 100, about 120, about 140, about 160, about 180, or about 200 amino acid residues in length.

The antigenic epitope amino acid sequences, as well as the immunogenic peptides and polypeptides comprising them may be encoded by a polynucleotide sequence that preferably is at least about 18 nucleotides in length; at least about 30 nucleotides in length; at least about 45 nucleotides in length; at least about 60 nucleotides in length; at least about 75 nucleotides in length; at least about 90 nucleotides in length; at least about 105 nucleotides in length; at least about 120 nucleotides in length; at least about 135 nucleotides in length; at least about 160 nucleotides in length; at least about 175 nucleotides in length; or longer, including, for example, those polynucleotides of at least about 200, about 300, about 400, about 500, about 600 or about 700 or more nucleotides in length.

Antigenic epitopes, as well as the immunogenic peptides and polypeptides comprising them, may be linear, i.e., be comprised of contiguous amino acids in a polypeptide, or may result from the three-dimensional folding of the primary amino acid sequence into a tertiary conformation, i.e., where an epitope is comprised of non-contiguous amino acids which become spatially proximate to each other as a result of the secondary and/or tertiary structure of the polypeptide that comprises the epitopic sequence.

Preferably, the repeated antigenic epitopes according to the present invention (either alone, or in combination with one or more heterologous T-cell stimulating epitopes), can be collinearly expressed, multimeric, and/or crosslinked through a chemical bond (i.e., conjugated) to form an immunogenic composition. Such immunogenic compositions may include one or more peptide antigens, and in certain embodiments, will include preferably two, or even 3 or more antigenic sequences that can be the same repeated antigen in multiple copies, or alternatively, two or more distinct antigens, which may be obtained from different strains, species, or organisms. In some embodiments, the immunogenic compositions of the invention will include a first antigen, and a second distinct antigen that is present in the immunogenic composition in two or more multiples. Alternatively, in other embodiments, the immunogenic composition will include three multiples of a single antigen, four multiples of a single antigen, or even five or more multiples of a single antigen. In some cases, each multiple may be an identical copy of the antigen repeated a number of times. In other case, the multiples may be substantially homologous to each other (but not necessarily identical copies of the same primary amino acid sequence). In fact, in some cases, it may be desirable to formulate an immunogen that contains three repeated antigenic motifs that are at least about 95% or more identical to each other in primary amino acid sequence. Schematically illustrative combinations of the individual epitopes that may be used to prepare an immunogenic polypeptide or vaccine may be shown as follows:

| | |
|---|---|
| A + A | two identical copies of a single antigen. |
| A + B | two distinct antigens. |
| A + B + B | two distinct antigens + a second identical copy of one of the antigens. |
| A + A + B + B | two identical copies each of two distinct antigens. |
| A + A' | two non-identical (but substantially homologous) multiples of a single antigen. |
| A + A' + B + B' | two non-identical (but substantially homologous) multiples each of two distinct antigens. |
| A + A' + A" + A'" | four non-identical (but substantially homologous) multiples of a single antigen. |

In the case of multiple antigens, it is important to note that they may be arranged in any order relative to one another in the overall immunogenic peptide or polypeptide sequence. Thus, a polypeptide immunogen that comprises two non-identical (but substantially homologous) multiples each of two distinct antigens may include a primary amino acid sequence in which the individual epitopes may be arranged in any combination. Using the schematic convention adopted above, such a composition could include the epitopes arranged linearly in the immunogenic polypeptide in any of the possible patterns:

- - - A-B—B'-A' - - -
- - - A-B-A'-B' - - -
- - - A-B'—B-A' - - -
- - - A-B'-A'-B - - -
- - - A-A'-B—B' - - -
- - - A-A'-B'—B - - -
- - - A'-A-B'—B - - -
- - - A'-A-B—B' - - -
- - - A'-B—B'-A - - -
- - - A'-B-A'-B' - - -
- - - A'-B'-A'-B - - -
- - - A'-B'—B-A' - - -
- - - B—B'-A'-A - - -
- - - B—B'-A-A' - - -
- - - B-A'-A-B - - -
- - - B-A'-B-A - - -
- - - B-A-B'-A' - - -
- - - B-A'-B'-A - - -
- - - B'-A-B'—B - - -
- - - B'-A-B—B' - - -
- - - B'—B—B'-A - - -
- - - B'—B-A-B' - - -
- - - B'-A'-A-B - - -
- - - B'-A'-B-A - - -

Note that the number of amino acid residues preceding, interrupting, or following each of the antigenic peptide sequences in the overall primary sequence of the immunogenic composition may vary from composition to composition, and from antigen combination to antigen combination. The number of "spacer" amino acids between two or more of the epitopic sequences can be of any practical range, including, for example, from 1 or 2 amino acids to 3, 4, 5, 6, 7, 8, 9, or even 10 or more amino acids between adjacent epitopes.

Schematically, an immunogenic composition including a consensus motif having two non-identical (but substantially homologous) multiples each of two distinct antigens could be written as follows:

$(Xaa)_n$-Epitope A-$(Xaa)_n$-Epitope B'-$(Xaa)_n$-Epitope A'-$(Xaa)_n$-Epitope B-$(Xaa)_n$ Likewise, a schematic representation of an immunogenic composition including a consensus motif having two identical, and three non-identical (but substantially homologous) multiples of a single antigen could be written as follows:

(Xaa)$_n$-Epitope A-(Xaa)$_n$-Epitope A'-(Xaa)$_n$-Epitope A-(Xaa)$_n$-Epitope A'''-(Xaa)$_n$-Epitope A''-(Xaa)$_n$ Similarly, a schematic representation of an immunogenic composition including a consensus motif having a first antigen, a second antigen, and four non-identical (but substantially homologous) multiples of a third antigen could be written as follows:

(Xaa)$_n$-Epitope A-(Xaa)$_n$-Epitope B-(Xaa)$_n$-Epitope C-(Xaa)$_n$-Epitope C''-(Xaa)$_n$-Epitope C'-(Xaa)$_n$-C'''-(Xaa)$_n$.

Where Xaa is any amino acid, and n is the number of amino acids in the spacer/linker coupling the various epitopes together into a single primary peptide/polypeptide sequence.

In other embodiments, immunogens of the present invention can also be presented on a polysaccharide or other suitable carrier or scaffold. This structure of such a vaccine, without being bound by theory, is believed to induce greater immunogenicity and immune memory in the host, thereby facilitating an increase in immunogenic response due to the increased local concentration of antigen as encountered by immune system cells. Immunogens arrayed in such a manner can be used in the conjugate vaccines of this invention.

Another alternative presentation of immunogens includes dimeric molecules, or dimeric portions thereof. In this format, a linking bond, preferably covalent, can be used to cross-link two or more peptides to form a dimer, trimer, tetramer, etc. Conjugate vaccines in which the peptides are arrayed in this manner can be more antigenic than vaccines made with the corresponding monomeric peptide conjugates. While numerous immunogens according to the invention may be envisioned and prepared by those of ordinary skill in the art based on the guidance provided herein, a few examples include the following (where A, B, and C signify different peptide sequences): M2$_A$/M2$_{B/M}$2$_A$/T-cell/M2$_B$/M2$_A$; NA$_A$/M2$_A$/T-cell/M2$_A$/NA$_A$/PB1$_A$/PB2$_B$; NA$_A$/M2$_A$/HA$_A$; HA$_A$/NA$_A$/T-cell/HA$_A$/NA$_A$; NA$_A$/NA$_B$/M2$_A$/M2$_B$/T-cell; NA$_A$/NA$_B$/ NA$_A$/NA$_B$/NA$_A$/NA$_B$; NA$_A$/NA$_B$/NA$_C$/NA$_A$/NA$_B$/NA$_C$; HA$_A$/M2$_A$/T-cell/M2$_B$/NA$_A$; HA$_A$/M2$_B$/PB1$_A$/PB2$_A$/T-cell/ M2$_A$/NA$_A$; or any combination thereof, including cocktails or mixtures thereof. Target antigens and immunogenic compositions prepared according to preferred embodiments of the present invention present epitopes in orders and arrangements not found in nature.

Polynucleotide Compositions

Any polynucleotide that encodes one or more of the immunogenic peptides or polypeptides as described herein, or that is complementary to such a polynucleotide, is also encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

The polynucleotides of the invention may encode epitopic peptides or antigens, or may encode an entire immunogenic peptide or polypeptide that comprises a plurality of individual epitopes and/or smaller peptide antigens, or may encode a variant of one or more such peptides or polypeptides as described herein. Polynucleotide variants may contain one or more substitutions, additions, deletions and/or insertions such that the immunogenicity of the encoded peptide is not diminished, relative to the native immunogenic protein. The effect on the immunogenicity of the encoded peptide may generally be assessed as described herein. Preferred peptide variants contain amino acid substitutions, deletions, insertions and/or additions at no more than about 20%, more preferably at no more than about 15%, and more preferably still, at no more than about 10% or 5% or less of the amino acid positions relative to the corresponding native unmodified amino acid sequence.

Likewise, polynucleotides encoding such peptide variants should preferably contain nucleotide substitutions, deletions, insertions and/or additions at no more than about 20%, more preferably at no more than about 15%, and more preferably still, at no more than about 10% or 5% or less of the nucleotide positions relative to the corresponding polynucleotide sequence that encodes the native unmodified amino acid sequence. Certain polynucleotide variants, of course, may be substantially homologous to, or substantially identical to the corresponding region of the nucleotide sequence encoding an unmodified peptide. Such polynucleotide variants are capable of hybridizing to a naturally occurring DNA sequence encoding one or more antigenic peptides as disclosed herein (or a complementary sequence) under moderately stringent, to highly stringent, to very highly stringent conditions.

Suitable moderately stringent conditions include, e.g., prewashing in a solution containing about 5×SSC, 0.5% SDS, 1.0 mM EDTA (pH 8.0); hybridizing at a temperature of from about 50° C. to about 60° C. in 5×SSC overnight; followed by washing twice at about 60 to 65° C. for 20 min. with each of 2×, 0.5× and 0.2×SSC containing 0.1% SDS). Suitable highly stringent conditions include, e.g., pre-washing in a solution containing about 5×SSC, 0.5% SDS, 1.0 mM EDTA (pH 8.0); hybridizing at a temperature of from about 60° C. to about 70° C. in 5×SSC overnight; followed by washing twice at about 65 to 70° C. for 20 min. with each of 2×, 0.5× and 0.2×SSC containing 0.1% SDS). Representative examples of very highly stringent hybridization conditions may include, for example, pre-washing in a solution containing about 5×SSC, 0.5% SDS, 1.0 mM EDTA (pH 8.0); hybridizing at a temperature of from about 70° C. to about 75° C. in 5×SSC overnight; followed by washing twice at about 70° C. to about 75° C. for 20 min. with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a given primary amino acid sequence. Some of these polynucleotides bear minimal homology to the nucleotide sequence of any native gene. Nonetheless, polynucleotides that vary due to differences in codon usage are specifically contemplated by the present invention.

Immunogenic peptide-encoding polynucleotides may be synthesized by any method known in the art, including chemical synthesis (e.g., solid phase phosphoramidite chemical synthesis). Modifications in a polynucleotide sequence may also be introduced using standard mutagenesis techniques, such as oligonucleotide-directed site-specific mutagenesis. Alternatively, RNA molecules may be generated by in vitro or in vivo transcription of DNA sequences encoding an immunogenic composition as disclosed herein, provided that the DNA is incorporated into a vector with a suitable RNA polymerase promoter (such as T7 or SP6). Certain portions may be used to prepare an encoded peptide, as described herein. In addition, or alternatively, a portion may be administered to a patient such that the encoded peptide is generated in vivo (e.g., by transfecting antigen-presenting cells such as dendritic cells with a cDNA construct encoding one or more immunogenic peptides, and administering the transfected cells to the patient).

Polynucleotides that encode an immunogenic peptide may generally be used for production of the peptide, in vitro or in vivo. Any polynucleotide may be further modified to increase stability in vivo. Possible modifications include, but are not limited to, the addition of flanking sequences at the 5'-end, 3'-end, or both; the use of phosphorothioate or 2'-o-methyl rather than phosphodiesterase linkages in the backbone; and/ or the inclusion of nontraditional bases such as inosine, queosine and wybutosine, as well as acetyl-methyl-, thio- and other modified forms of adenine, cytidine, guanine, thymine and uridine, or any combination thereof.

Nucleotide sequences as described herein may be joined to a variety of other nucleotide sequences using established recombinant DNA techniques. For example, a polynucleotide may be cloned into any of a variety of cloning vectors, including one or more of plasmids, phagemids, lambda phage derivatives and cosmids. Vectors of particular interest include expression vectors, replication vectors, probe generation vectors, and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for prophylactic and therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, influenzavirus adenovirus, baculovirus, parvovirus, herpes virus, adeno-associated virus, retrovirus, flavivirus, vaccinia or poxvirus (e.g., avian poxvirus). Techniques for incorporating DNA into such vectors are well known to those of ordinary skill in the art. A viral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

In some cases the immunogenic peptides of the invention, or polynucleotides encoding them, may be formulated in an inactivated, killed, attenuated, reassortant, or recombinant viral vector, or in one or more virions, or viral particles comprising such, particularly when contemplated for suitable formulation as a vaccine component or such like.

Pharmaceutical Formulations

In certain embodiments, the present invention concerns formulation of one or more therapeutic or prophylactic agents in a pharmaceutically acceptable composition for administration to a cell or an animal, either alone, or in combination with one or more other modalities of prophylaxis and/or therapy. The formulation of pharmaceutically-acceptable excipients and carrier solutions is well known to those of ordinary skill in the art, as is the development of suitable dosing and treatment regimens for using the particular compositions described herein in a variety of treatment regimens.

In certain circumstances it will be desirable to deliver the disclosed immunogenic compositions in suitably-formulated pharmaceutical vehicles by one or more standard delivery routes, including, for example, subcutaneously, intraocularly, intravitreally, parenterally, intravenously, intracerebroventricularly, intramuscularly, intrathecally, orally, intraperitoneally, transdermally, topically, by oral or nasal inhalation, or by direct injection to one or more cells, tissues, or organs. The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase, or pharmacologically acceptable salts, may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations preferably can contain a preservative to prevent the growth of microorganisms.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, a sterile aqueous medium that can be employed will be known to those of ordinary skill in the art in light of the present disclosure. For example, one dosage may be dissolved in 1 mL of isotonic NaCl solution, and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will determine, in any event, the appropriate dose for the individual subject. Moreover, for human administration, preparations should meet sterility, pyrogenicity, and the general safety and purity standards as required by FDA Office of Biologics standards.

Sterile injectable compositions may be prepared by incorporating the disclosed immunogenic compositions in the required amount in the appropriate solvent with several of the other ingredients enumerated above, as required, followed by filtered sterilization. Generally, dispersions can be prepared by incorporating the selected sterilized active ingredient(s) into a sterile vehicle that contains the basic dispersion medium and the required other ingredients from those enumerated above. The compositions disclosed herein may also be formulated in a neutral or salt form. Pharmaceutically-acceptable salts include the acid addition salts (formed with the free amino groups of the protein), and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like.

The amount of immunogenic composition(s) and the time needed for the administration of such immunogenic composition(s) will be within the purview of the ordinary-skilled artisan having benefit of the present teachings. It is likely, however, that the administration of a therapeutically-effective, pharmaceutically-effective, and/or prophylactically-effective amount of the disclosed immunogenic compositions may be achieved by a single administration, such as for example, a single injection of a sufficient quantity of the delivered agent to provide the desired benefit to the patient undergoing such a procedure. Alternatively, in some circumstances, it may be desirable to provide multiple, or successive administrations of the immunogenic compositions, either over a relatively short, or even a relatively prolonged period of time, as may be determined by the medical practitioner overseeing the administration of such compositions to the selected individual.

Typically, formulations of one or more active ingredients in the immunogenic formulations disclosed herein will contain an effective amount for the selected therapy or prophylaxis. Preferably, the formulation may contain at least about 0.0001%, or at least about 0.001%, or at least about 0.01%, or at least about 0.1%, of each active ingredient, although the percentage of the active ingredient(s) may, of course, be varied, and may conveniently be present in amounts from about 0.2 to about 80 weight % or volume %, or from about 0.5 to about 70 weight % or volume %, or more preferably, from about 1 to about 50 weight % or volume %, based upon the total formulation. Naturally, the amount of active compound(s) in each immunogenic composition may be prepared in such a way that a suitable dosage will be obtained in any given unit dose of the compound. Factors such as solubility, bioavailability, biological $t_{1/2}$, route of administration, product shelf life, as well as other pharmacological considerations will be contemplated by one of ordinary skill in the art of preparing such pharmaceutical formulations, and as such, a variety of dosages and treatment regimens may be desirable.

The immunogenic compositions disclosed herein are not in any way limited to use only in humans, or even to primates, or mammals. In preferred embodiments, however, the compositions of the present invention may be formulated for administration to a mammal, including a human, for one or more therapeutic and/or prophylactic regimens. The disclosed compositions may also be formulated for veterinary administration, including, for example, to selected livestock, exotic or domesticated animals, companion animals (including pets and such like), non-human primates, as well as zoological or otherwise captive specimens, and such like.

The immunogenic compositions and vaccines of the present invention are preferably administered in a manner compatible with the dosage formulation, and in an amount to be prophylactically or therapeutically effective and preferably immunogenic. The quantity to be administered depends on various routine factors the subject to be treated, including, e.g., the capacity of the patient's immune system to mount an immune response, and the degree of protection desired. Suitable dosage ranges may be on the order of several hundred micrograms (µg) of active ingredient per dose (e.g., per vaccination) with a preferred range from about 0.1 µg to 2000 µg (even though higher amounts, such as, e.g., in the range of about 1 to about 10 mg are also contemplated), such as in the range from about 0.5 µg to 1000 µg, preferably in the range from about 1 µg to about 500 µg and especially in the range from about 10 µg to about 100 µg. Suitable regimens for initial administration and booster shots are also variable through titering or other dose determination techniques, but are typified by an initial administration followed by optional but preferred subsequent inoculations or other periodic administrations.

In certain embodiments, the dose would consist of the range of about 1 µg to about 1 mg total protein or target antigen. In one exemplary embodiment, the vaccine dosage range is about 0.1 µg to about 10 mg. However, one may prefer to adjust dosage based on the amount of peptide delivered. In either case, these ranges are merely guidelines from which one of ordinary skill in the art may deviate according to conventional dosing techniques. Precise dosages may be determined by assessing the immunogenicity of the conjugate produced in the appropriate host so that an immunologically effective dose is delivered. An immunologically effective dose is one that stimulates the immune system of the patient to establish a detectable immune response to the immunogenic composition or vaccine. Preferably, a level of immunological memory sufficient to provide long-term protection against disease caused by microbial infection is obtained. The immunogenic compositions or vaccines of the invention may be preferably formulated with an adjuvant. By "long-term" it is preferably meant over a period of time of at least about 6 months, over at least about 1 year, preferably over at least about 2 to 5 years, or even at least about 2 to about 10 years or longer.

The timing of dose administration depends upon factors that are known to, or readily determined by, those of ordinary skill in the art, particularly with the guidance provided herein. After an initial administration, one or more booster dose(s) may subsequently be administered to elicit a stronger immune response, to maintain or even increase the titer of antibodies specific for the administered immunogen, or both. An example of a dosing regime would be a dose on day 1, a second dose at 1 or 2 months, a third dose at either 4, 6 or 12 months, and additional booster doses over long-term time frames or as needed. A preferred dosing regime would be to administer a composition of the invention on day 1, while another preferred dosing regime would be to administer a composition of the invention on day 1 coupled with a second administration between 1 month to 14 months later. Furthermore, the present vaccines may be used as boosters for other vaccines previously administered to a patient, such as a conventional Flu vaccine. In such cases, a standard prime-boost time schedule may be followed as is known to those of ordinary skill in the art.

In some embodiments, the subject in need of prevention or treatment is administered an amount of an immunogenic polypeptide composition, or a vaccine comprising it, that is sufficient to induce a detectable response in the animal receiving the administration. The immunogenic compositions and vaccines of the invention preferably include at least a first antigenic epitope including one or more repeatedly occurring peptide sequences, wherein each peptide sequence is conserved across at least a plurality of microbial and/or viral species, strains, and serotypes, together with at least one pharmaceutically-acceptable diluent, vehicle, buffer, excipient, or carrier, or a combination thereof. Subsequent to administering, the subject may be evaluated to determine if a detectable immune response exists.

Methods for Making Antigenic Peptides and Polypeptides of the Invention

The peptides of the present invention can be produced using any techniques available to those of ordinary skill in the art, such as chemical and biochemical synthesis. Examples of techniques for chemical synthesis of peptides are provided in Lee, *Peptide and Protein Drug Delivery*, New York, N.Y., Dekker (1990); in Ausubel, *Current Protocols in Molecular Biology*, John Wiley, 1987-1998, and in Sambrook et al. (1989); each of which is also specifically incorporated herein in its entirety by express reference thereto.

The target antigens of the present invention may be produced synthetically, or naturally, for example as a recombinant protein vaccine, or a combination thereof. A "recombinant protein vaccine" is a vaccine whose active ingredient includes at least one protein antigen that is produced by recombinant expression. The vaccine antigens may be produced in bacteria, mammalian cells, baculovirus cells, and/or plant cells, or hybrids thereof, for example. An exemplary method of producing influenza vaccines involves growth of an isolated strain in embryonated hen's eggs.

The inventive target antigens, or portions thereof, may be produced or manufactured totally synthetically, e.g., cell-free translation systems or by chemical protein synthesis, in cells to include bacteria (e.g., *Escherichia coli, Bacillus* spp.) in mammalian cells or inert cells, fungi, or the like. The target antigens of the present invention may be obtained through any of the routes that are well known or available to those of ordinary skill in the art, including for example, recombinant production in vivo and chemical synthesis, such as SPPS and the like. Recombinant production in vivo refers to the harvesting of protein from eukaryotic or prokaryotic cell cultures wherein the cells contain heterologous nucleotide coding sequences, typically within a plasmid under control of regulatory sequences, that code for one or more of the antigenic peptides or polypeptides of the present invention.

Those of ordinary skill in the art will be capable of preparing such a plasmid using the genetic code to determine the nucleotide sequence necessary to encode the desired polypeptide sequence in combination with well-known regulatory sequences and commercially-available plasmid vectors, particularly coupled with the guidance herein. Such systems are well known in the art, and standard recombinant DNA and molecular cloning techniques usable in connection with the present invention are known in the art and are described more fully, e.g., in Sambrook et al. (1989). SPSS is an established method for producing polypeptides in an automated setting completely free of any living system. For a review of SPPS and the chemistries involved, see John M. Stewart and Janice D. Young, *Solid-Phase Peptide Synthesis*, Second Ed, 1984, (Pierce Chemical Co., Rockford, Ill., USA). Recent patents directed to SPPS instruments and apparatus include U.S. Pat. Nos. 4,746,490; 4,668,476; 4,816,513; and 5,186,898; each of which is specifically incorporated herein in its entirety by express reference thereto.

Preparation of Peptide-Based Vaccines is Generally Well Understood by Those of Ordinary skill in the art, and can be accomplished by a variety of available techniques, including, for example, those described in U.S. Pat. Nos. 4,608,251; 4,601,903; 4,599,231; 4,599,230; and 4,596,792; and generally as provided in *Remington's Pharmaceutical Sciences*, 16th Edition, A. Osol, (ed.), Mack Publishing Co., Easton, Pa. (1980), and *Remington's Pharmaceutical Sciences*, 19th Edition, A. R. Gennaro, (ed.), Mack Publishing Co., Easton, Pa. (1995), each of which is specifically incorporated herein in its entirety by express reference thereto.

The antigens, epitopes, and immunogenic compositions disclosed herein may be prepared by any method available to those of ordinary skill in the art, although in one preferred embodiment the target antigens, or their component repeated conserved peptide sequences, are synthetically prepared by solid phase protein synthesis (SPPS). Optionally, the repeated conserved peptide sequences are further presented with single or repeated occurrences of additional immunogenic components. Such additional components may be joined into the target antigens by way of collinear expression (i.e., fusion protein synthesis) or by chemical conjugation, which are each well known in the art. In some embodiments, target antigens are presented on or in cells, organisms and/or incomplete organisms (e.g., BCG and adeno-like viral particles, including for example, members of the Parvoviridae) to provide enhanced immune response. Even further, the target antigens may be synthesized in vivo as products of genetic manipulation of the host cells, i.e., as contained within a vector (e.g., recombinant viral vector), on a vector (e.g., coating a ballistic particle) or as a naked DNA or RNA vaccine.

Techniques for preparing recombinant vaccines and delivering DNA/RNA vaccines are well known in the art, can be used in association with the present invention, and are discussed, for example, in U.S. Pat. Nos. 7,223,409 and 6,603,998, each of which is specifically incorporated in its entirety by express reference thereto. For general laboratory procedures, reference is given to Sambrook et al. (1989), which is also specifically incorporated herein in its entirety by express reference thereto.

Exemplary epitopic peptides useful in the practice of the invention include, but are not limited to, those peptides of defined length that can be from about 6 to about 100 amino acids in length, alternatively from about 8 to about 90 amino acids in length, alternatively still, from about 10 to about 80 amino acids in length; or from about 12 to about 70 amino acids in length, alternatively still, from about 14 to about 60 amino acids in length; or from about 16 to about 50 amino acids in length, or from about 18 to about 40 amino acids in length, or from about 20 to about 30 amino acids in length, or any defined length within one or more of the recited ranges with an integer as each endpoint. Alternatively, the isolated epitopic sequences useful in the preparation of the immunogenic peptide and polypeptide compositions disclosed herein may preferably each comprise, consist essentially of, or alternatively, consist of, a primary amino acid sequence that is from about 6 to 35 amino acids in length, alternatively about 8 to 30 amino acids in length; or alternatively about 10 to 20 amino acids in length; although longer and shorter peptide epitopes are contemplated to fall within the scope of the present disclosure. In some embodiments, the isolated epitopic sequences will each comprise, consist essentially of, or alternatively, consist of, a sequence that is about 10, about 15, about 20, about 25, about 30, about 35, about 40, about 45, or about 50 or more amino acids in length.

Exemplary immunogenic peptides or polypeptides that comprise one or more of the disclosed epitopic antigenic sequences will preferably be from about 12 to about 400 amino acids in length, alternatively from about 18 to about 350 amino acids in length, alternatively still, from about 24 to about 300 amino acids in length; or from about 30 to about 250 amino acids in length, alternatively still, from about 30 to about 200 amino acids in length; or from about 36 to about 150 amino acids in length, or from about 42 to about 100 amino acids in length, or any defined length within one or more of the recited ranges with an integer as each endpoint.

Likewise, in certain applications, the immunogenic peptides or polypeptides that comprise one or more of the disclosed epitopic antigenic sequences may preferably each comprise, consist essentially of, or alternatively, consist of, an amino acid sequence that is from about 50 to 60 amino acids in length, alternatively about 60 to 70 amino acids in length; alternatively about 70 to 80 amino acids in length, about 80 to 90 amino acids in length; or alternatively, about 90-100 amino acids in length, although longer and shorter peptide epitopes are contemplated to fall within the scope of the present disclosure. In some embodiments, the immunogenic peptides or polypeptides that comprise one or more of the disclosed epitopic antigenic sequences may preferably each comprise, consist essentially of, or alternatively, consist of, an amino acid sequence that is about 30, about 60, about 90, about 120, about 150, about 180, about 210, about 240, or about 270 or so amino acids in length.

Adjuvants

Some of the polypeptides of the present invention are preferably sufficiently immunogenic to provide a prophylactic effect in a vaccine. For others, however, the immune response can be increased if the immunogenic composition further includes an adjuvant. The term "adjuvant" has its usual meaning in the art of vaccine technology, i.e., a substance or a composition of matter that is: 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, and vaccination with the immunogen may or may not give rise to an immune response against the immunogen, but the combined vaccination (or other prophylaxis or therapy) with immunogen and adjuvant induces an immune response against the immunogen that is stronger than that induced by the immunogen alone.

Various methods of achieving adjuvant effect for the vaccine and other compositions are known and can be applied in association with the present invention. General principles and methods suitable for use in accordance with the invention are detailed in "The Theory and Practical Application of Adjuvants." Duncan E. S. Stewart-Tull (Eds.), John Wiley & Sons Ltd, Malden, Mass., USA (1995); and in "Vaccines: New Generation Immunological Adjuvants," Gregoriadis et al., (Eds.), Plenum Press, New York, N.Y., USA (1995), the disclosure of each of which is specifically incorporated herein in its entirety by express reference thereto.

Preferred adjuvants include those that correlate, and preferably cause a "stimulation of the immune system." A stimulation of the immune system means that a substance or composition of matter exhibits a general, non-specific immunostimulatory effect. A number of adjuvants and putative adjuvants (such as certain cytokines) share the ability to stimulate the immune system. The result of using an immunostimulating agent tends to be an increased "alertness" of the immune system, meaning that simultaneous or subsequent immunization with an immunogen can induce a significantly more effective immune response compared to isolated use of the immunogen. Complete Freund's adjuvant ("CFA") is a preferred adjuvant for use in association with vaccines of the present invention. Other preferred adjuvants include those that would drive levels of increased protective immunity through either the cellular or the humoral system.

Non-limiting examples of an adjuvant for use in the present invention includes one or more immune targeting adjuvants; immunomodulating adjuvants such as a toxin, a cytokine, and a mycobacterial derivative; incomplete Freund's adjuvant, aluminum phosphate, aluminum hydroxide, alum, Stimulon® QS-21 (Aquila Biopharmaceuticals, Inc., Framingham, Mass., USA), MPL® (3, 0, deacylated monophosphoryl lipid A; Corixa Corp., Hamilton, Mont., USA), and interleukin-12 (Genetics Institute, Cambridge, Mass., USA), an oil formulation; a polymer; a micelle forming adjuvant; a saponin; an immunostimulating complex matrix (ISCOM matrix); a particle; DDA; DNA adjuvants; an encapsulating adjuvant; or any of the adjuvants as described in U.S. Pat. Nos. 7,357,936; 7,090,853; 6,793,928; 6,780,421; 6,759,241; 6,713,068; 6,572,866; 6,534,065; 6,451,325; 6,440,423; 6,306,404; 6,060,068; 6,033,673; 5,800,810; 5,795,582; 5,785,975; 5,679,356; 5,503,841; and 5,182,109, the entire disclosure of each of which is specifically incorporated herein in its entirety by express reference thereto.

Certain adjuvants are preferably T-cell stimulating in nature. Preferred adjuvants include detoxified heat-labile *E. coli* enterotoxin adjuvant and the like. Aluminum-based adjuvants may also be used, including aluminum hydroxide, and more preferably aluminum phosphate. Adjuvants (i.e., carriers) may also include sterile liquids such as water, saline, petroleum oil, vegetable oil, soybean oil, peanut oil, mineral oil, or any combination thereof.

The adjuvant may also include one or more agents such as aluminum hydroxide or phosphate (alum), commonly used as about 0.05% to 0.1% solution in buffered saline, admixture with synthetic polymers of sugars (e.g., Carbopol® Noveon, Inc. Cleveland, Ohio, USA) used as 0.25% solution, aggregation of the protein in the vaccine by heat treatment with temperatures ranging from about 70° C. to about 101° C. for about 30 sec to about 2 min periods, respectively, and also aggregation by means of cross-linking agents is also possible. Aggregation by reactivation with pepsin-treated antibodies (including, for example, Fab fragments) to albumin, mixture with bacterial cells such as *C. parvum* or endotoxins or lipopolysaccharide components of Gram-negative bacteria, emulsion in physiologically acceptable oil vehicles such as mannide mono-oleate (Aracel-A®, Sigma Chemical Co.) or emulsion such as with 20% solution of a perfluorochemical blood substitute (e.g., Fluosol-DA®), or any combination thereof, may also be employed. Admixture with oils such as squalene and IFA is also preferred.

The antigenic compositions of the invention may be conjugated to or expressed on one or more carriers. U.S. Pat. Appl. Pub. No. 2004/0223976 discusses exemplary methods for conjugation, and is specifically incorporated herein in its entirety by express reference thereto. For conjugation, a carrier may be a fungus, a bacterium, a virus or a virus-like particle or a portion thereof, a protein or protein complex (e.g., complete or incomplete capsid particle), polysaccharide (as noted above) or polysaccharide complex, a polynucleotide or polynucleotide complex (double helix, triple helix, hairpin loop, etc.), an organic or inorganic polymer, a microbead or microsphere, a nanoparticle or nanosphere, a ballistic particle, etc., and any combination thereof. As used herein, a "carrier protein" means an immunogenic or nonimmunogenic protein to which the peptide and one or more polypeptide sequences, polysaccharides, and/or other antigens are conjugated. Various immunogenic carrier proteins are known in the art and may be used in conjugate vaccines. Preferred carrier proteins include, but are not limited to, the outer membrane protein complex (OMPC) of *Neisseria meningitidis*, tetanus toxoid protein, hepatitis B virus proteins (including, for example, the surface antigen protein [HBsAg] and the core antigen protein [HB CoreAg]); keyhole limpet hemocyanin (KLH); rotavirus capsid proteins; and the L1 protein of a bovine papillomavirus VLP or human papillomavirus VLP, for example, VLPs of HPV type 6, 11 or 16, etc, or pharmaceutically acceptable salts thereof, or any combination of the foregoing. In some embodiments, the epitopes can be formed as fusion polypeptides/proteins between influenza and 1) one or more multiple microbial peptides; 2) toll receptor ligands (including, for example, profillin and flagellin); or 3) receptor-reactive molecules, including, for example, CpG.

Inventive target antigens can be expressed on the surface of microbes, e.g., BCG, adenovirus, adeno-like virus, or even incomplete viral particles such as a portion of the foregoing or other virus particles.

Adjuvanted Antigenic Peptide Compositions

Although the antigenic compositions of the invention may be formulated alone (i.e., as peptides and repeated peptides), and in combination with each other, in other embodiments they may be formulated as polysaccharide vaccines, protein-polysaccharide vaccines, conjugated vaccines, or together as fusion proteins (e.g., with HA or NA sequences, or both). Conjugates may take the form of a microbial or viral antigen. A "microbial or viral antigen," as used herein, refers to an antigen or epitopic sequence of a microorganism or a virus, and includes, but is not limited to, infectious or pathogenic virus, bacteria, yeast, fungi, parasites, amoebae, or any combination thereof. Such antigens may include the intact virus or microorganism itself, as well as natural isolates, fragments, capsids, cell fractions, membrane components, lysates, or derivatives thereof, as well as synthetic or recombinant compounds which are identical, or similar (i.e., substantially homologous), to a native (i.e., in vivo or in situ) antigen obtained from such a microorganism or virus. In all such cases, an antigen preferably will illicit an immune response in at least a first animal (and preferably, mammal) when presented to the immune system of the animal host.

In embodiments of the invention involving polyvalent, or polymicrobial immunogens and vaccines, the immunogen will preferably comprise at least two distinct antigens, at least one of which is specific for a particular microbe or virus. In the case of intraspecies polyvalent immunogens, such compositions will preferably comprise at least two different epitopes or antigens that elicit an immune response against two or more species of a given organism. Alternatively, in the case of interspecies polyvalent immunogens, such compositions will preferably comprise at least two different epitopes or antigens that elicit an immune response against at least one species from one organism, and that also elicit an immune response against at least one species from a second different organism.

Exemplary intraspecies polyvalent immunogens include, but are not limited to, compositions that comprise antigens specific for two or more strains of a single species of virus (e.g., two or more influenzavirus strains), or two or more strains of a single species of bacterium (e.g., two or more *Staphylococcus* strains).

Exemplary interspecies polyvalent immunogens include, but are not limited to, compositions that comprise antigens specific for two different species of organism (e.g., one viral species and one bacterial species (e.g., influenzavirus and *Escherichia*); two different viral species (e.g., influenzavirus and Dengue virus), two different bacterial species (e.g., *Streptococcus* and *Clostridium*).

A compound is similar to a natural microorganism antigen if it induces an immune response (humoral and/or cellular) to a natural microorganism antigen. Such antigens are used routinely in the art and are well known to the ordinary-skilled artisan, and may include a fungus, bacterium, a virus, or virus-like particle, or a portion thereof, or a combination thereof. Generally, if vaccination with the conjugate reduces the level of infection or the severity of the resulting disease, then the peptide and conjugate is considered useful in the preparation of the vaccine.

For example, the antigens disclosed herein may be conjugated to polysaccharides, such as PRP, staphylococcal, meningococcal, or pneumococcal polysaccharide, to provide enhanced immunogenic response in populations with less than optimal immunity or where such an approach is otherwise advantageous. Conjugate vaccines, in some embodiments, are characterized by production that involves the conjugation of the polysaccharide antigen with a protein. This conjugation may convert the T-cell-independent carbohydrate antigen into a T-cell-dependent antigen, increasing the immunological response to the polysaccharide. The immunologic response to the polypeptide obtained when providing an array of multiple antigenic targets on the pneumococcal polysaccharide backbone can advantageously provide crosslinking on antigen processing cells of the host immune system. Conjugating the influenza protein to a polysaccharide, such as PRP, may improve universal protection against the bacterium *Haemophilus influenzae*, and thus the vaccine of the present invention may be applicable for use in countries, particularly developing countries, where it is advantageous to obtain widespread protection against *H. influenzae* as well as influenzavirus. Other potential polysaccharide and polysaccharide-derivative sources may include bacterial species such as, but not limited to, *Pneumococcus* spp., *Salmonella* spp., *Shigella* spp. *Vibrio* spp., *Klebsiella* spp., *Neisseria* and other meningococcal spp. *Streptococcus* spp., *Staphylococcus* spp., or any combination thereof. Other polysaccharides, lipopolysaccharides, lipoteichoic acids, lipopeptides, derivatives thereof, or other microbially-related antigenic compounds that may be conjugated to one or more of the immunogenic peptide compositions of the present invention to form a polyvalent, and/or polymicrobial vaccine would be readily understood to one of ordinary skill in the art, particularly in view of the guidance provided herein. Moreover, any method available to those of ordinary skill in the art may be used to conjugate the immunogens and vaccines of the present invention with non-peptide compounds such as polysaccharides, lipids, lipopeptides, and the like, and any combination thereof.

Proteins may contain one or more T-cell epitopes that make them T-cell-dependent antigens capable of eliciting T-cell help when used as a vaccine antigen. Antigenic peptide and immunostimulatory amino acid sequences derived from diphtheria and tetanus toxoids, or any other T-cell epitope from any source, or portions or combinations of any of the foregoing and others, can also be used in the formulation of the immunogens and vaccines according to the invention. For example, the vaccine may include a peptide having at least one, and preferably two or more, M2 sequences or an immunogenic portion thereof, with at least one, and preferably two, T-cell inducing epitopes from the tetanus toxin operably linked to form the immunogen.

It is preferable, in certain embodiments, to formulate M2 peptide-protein conjugates with immunogens from influenza B virus, and/or with immunogens from bacterial species such as *Streptococcus pneumoniae, Staphylococcus aureus* and *H. influenzae*, viral species such as Orthohepadnaviruses (including, e.g., hepatitis A, B, and C virus), human papillomavirus, Flaviviruses (including, e.g., Dengue virus), Lyssaviruses (including, e.g., rabies virus), Morbilliviruses (including, e.g., measles virus), Simplexviruses (including, e.g., herpes simplex virus), Polyomaviruses, Rubulaviruses (including, e.g., mumps virus), Rubiviruses (including, e.g., rubella virus), Varicellovirus (including, e.g., chickenpox virus), Rotavirus, Cytomegalovirus, or any other immunogen or any combination thereof. Additionally, a vaccine of the present invention can be combined with or include other antigenic components of influenza A virus, including, for example, epitopes derived from hemagglutinin and neuraminidase proteins. In this manner, a combination vaccine can be made. Combination vaccines can provide the advantages of increased patient comfort and lower costs of administration due to the need for fewer inoculations.

The antigenic compositions of the present invention can be conjugated to carriers using any conjugation method in the art. For example, the conjugation can be achieved using sulfosuccinimidyl 4-(N-maleimidomethyl)cyclohexane-1-carboxylate (sSMCC), N-[ε-maleimidocaproyloxy]sulfosuccinimide ester (sEMCS), N-maleimidobenzoyl-N-hydroxysuccinimide ester (MBS), glutaraldehyde, 1-ethyl-3-(3-dimethylaminopropyl)carbodiimide (EDCI), Bisdiazobenzidine (BDB), or N-acetyl homocysteine thiolactone (NAHT), or a combination thereof.

In addition, staphylococcal proteins may be used as carrier proteins in the polysaccharide or LTA conjugates of the invention. The staphylococcal proteins described below may be used as carrier proteins; for example, laminin receptor, SitC/MntC/saliva binding protein, EbhA, EbhB, Elastin binding protein (EbpS), EFB (FIB), SBI, ClfA, SdrC, SdrG, SdrH, Lipase GehD, SasA, FnbA, FnbB, Cna, ClfB, FbpA, Npase, IsaA/P isA, SsaA, EPB, SSP-1, SSP-2, HBP, Vitronectin binding protein, fibrinogen binding protein, coagulase, Fig, MAP, Immunodominant ABC transporter, IsdA, IsdB, $Mg^{2+}$ transporter, HarA, SitC, Ni ABC transporter alpha-toxin (HIα), α-toxin H35R mutant, RNA III activating protein (RAP), MRPII and autolysin, or fragments thereof.

A new carrier protein that would be particularly advantageous to use in the context of a staphylococcal vaccine is a staphylococcal α-toxoid. The native form may be conjugated to a polysaccharide, since the process of conjugation tends to reduce toxicity. Preferably, a genetically detoxified α-toxin such as the H35L (histidine to leucine mutation at amino acid position 35) or H35R (histidine to arginine mutation at amino acid position 35) variants can be used as carriers since residual toxicity is lower. Alternatively, the α-toxin is chemically detoxified by treatment with a crosslinking reagent, such as formaldehyde or glutaraldehyde. A genetically-detoxified α-toxin may also be optionally chemically detoxified by treatment with one or more crosslinking agents to reduce or eliminate toxicity.

In some embodiments, the immunogenic composition of the invention comprises microbial polysaccharides. Polysaccharides are of native size or alternatively may be sized, for instance by microfluidization, ultrasonic irradiation or by chemical treatment. The invention also covers oligosaccharides derived from the type 5 and type 8 polysaccharides from S. aureus. In some embodiments, the immunogenic composition of the invention further comprises the polysaccharide PIA (or PNAG). PIA (or PNAG) may be of different sizes varying from over 400 kDa to between 75 and 40 kDa to between 10 and 75 kDa to oligosaccharides composed of up to 30 repeat units of (1→6)-β-D-glucosamine substituted with N-acetyl and O-succinyl constituents). In a further embodiment, the immunogenic composition of the invention comprises the S. aureus 336 antigen; alternatively, the type I, II and III polysaccharides from S. epidermidis may also be included in some embodiments of the invention.

The polypeptides may be linked to the carrier polysaccharides(s) by any known method (for example, by U.S. Pat. Appl. Pub. No. US2005/0169941; U.S. Pat. Nos. 4,372,945, 4,474,757, and 4,356,170, each of which is specifically incorporated herein in its entirety by express reference thereto). CDAP or amino-oxy conjugation chemistry may be carried out according to conventional methods, including for examples, those methods set forth in PCT Int. Pat. Appl. Pub. No. WO95/08348 and U.S. Pat. Appl. Pub. No. US2005/0169941, each of which is specifically incorporated herein in its entirety by express reference thereto.

Briefly, in CDAP, the cyanylating reagent 1-cyano-dimethylaminopyridinium tetrafluoroborate (CDAP) is preferably used for the synthesis of polysaccharide-protein conjugates. The cyanylation reaction can be performed under relatively mild conditions, which avoids hydrolysis of the alkaline sensitive polysaccharides. This synthesis allows direct coupling to a carrier protein. The polysaccharide is solubilized in water or a saline solution. CDAP is dissolved in acetonitrile and added immediately to the polysaccharide solution. The CDAP reacts with the hydroxyl groups of the polysaccharide to form a cyanate ester. After the activation step, the carrier protein is added. Amino groups of lysine react with the activated polysaccharide to form an isourea covalent link. After the coupling reaction, a large excess of glycine is then added to quench residual activated functional groups. The product is then passed through a gel permeation column to remove unreacted carrier protein and residual reagents. In an embodiment, LTA is conjugated using the amino-oxy method described in US Pat. Appl. Publ. No. 2005/0169941, which is specifically incorporated herein in its entirety by express reference thereto.

In the carrier maleimide-activation method, the conjugation is achieved using sulfosuccinimidyl 4-(N-maleimidomethyl)cyclohexane-1-carboxylate (sSMCC), or N-maleimidobenzoyl-N-hydroxysuccinimide ester (MBS). The method using sSMCC is widely used and highly specific (see, e.g., Meyer et al., [2002], the disclosure of which is specifically incorporated herein in its entirety by express reference thereto). sSMCC crosslinks the SH-group of a cysteine residue to the amino group of a lysine residue on the carrier protein.

In a further exemplary conjugation, more specifically in the conjugation reaction using sSMCC, the carrier can first be activated by binding the sSMCC reagent to the amine, e.g., lysine residues, of the carrier. After separation of the activated carrier from the excess reagent and the by-product, the cysteine-containing peptide is added and the link takes place by addition of the SH-group to the maleimide function of the activated carrier. The method using MBS can conjugate the peptide and the carrier through a similar mechanism.

The conjugation using sSMCC can be highly specific for SH-groups. Thus, the presence of at least one cysteine residue in the peptide sequence or polypeptide is generally essential for facile conjugation. If a peptide does not have a cysteine residue, a cysteine residue preferably should be added to the peptide, preferably at the N-terminus or C-terminus. If the desired epitope in the peptide contains a cysteine, the conjugation need not be carried out with a method using a sSMCC activated carrier. If the peptide contains more than one cysteine residue, the peptide need not be conjugated to the carrier using sSMCC, although preferably one is included if the excess cysteine residue can be replaced or modified.

In preferred embodiments, the linkage should not interfere with the desired epitope in the peptide. Any cysteine residues in the peptide are preferably separated from the desired epitope sequence with a distance of at least one amino acid as a spacer, or linker.

Another conjugation according to the methods of the present invention is use of N-acetyl-DL-homocysteine thiolactone (NAHT). For example, thiolactones can be used to introduce a thiol functionality onto OMPC, to allow conjugation with maleimidated or bromoacetylated-peptides (see e.g., Tolman et al. 1993; Conley et al., 1994).

In certain embodiments of the invention, conjugation reactions to couple the peptide to the carrier can involve introducing and/or using intrinsic nucleophilic groups on one reactant and introducing and/or using intrinsic electrophilic groups in the other reactant. For example, a nucleophilic thiol group can be introduced to the carrier protein (preferably OMPC) and then add electrophilic groups (preferably alkyl halides or maleimide) to the peptide. The resulting conjugate has thiol ether bonds linking the peptide and carrier. Direct reaction of the peptide electrophilic group (maleimide or alkyl halide) and intrinsic nucleophilic groups (preferably primary amines or thiols) of the carrier protein can lead to secondary amine linkages or thioether bonds. Alternative schemes involve adding a maleimide group or alkyl halide to the carrier and introducing a terminal cysteine to the peptide and/or using intrinsic peptide thiols again can result in thiol ether linkages when desired.

Antibody Compositions

The antigenic polypeptide compositions of the present invention find particular utility in the production of antibodies specific for the polypeptides given herein and/or polypeptides encoded by the polynucleotides of the invention, including e.g., those described herein, and conservative variants thereof. Antibodies specific for these polypeptides are useful, e.g., in both diagnostic and therapeutic/prophylactic purposes, e.g., related to the activity, distribution, and expression of target polypeptides.

As used herein, an "antibody" refers to a protein comprising one or more polypeptides substantially or partially encoded by immunoglobulin genes or fragments of immunoglobulin genes. The recognized immunoglobulin genes include the κ, λ, α, γ, δ, ε, and μ constant region genes, as well as myriad immunoglobulin variable region genes. Light chains are classified as either κ or λ. Heavy chains are classified as γ, μ, α, δ, or ε, which in turn define the immunoglobulin classes, IgG, IgM, IgA, IgD and IgE, respectively. Antibodies include, e.g., but are not limited to, polyclonal antibodies, monoclonal antibodies, multiple or single chain antibodies, including single chain Fv (sFv or scFv) antibodies in which a variable heavy and a variable light chain are joined together (directly or through a peptide linker) to form a continuous polypeptide, and humanized or chimeric antibodies.

Antibodies specific for the polypeptides of the invention can be generated by methods well known in the art. Such antibodies can include, but are not limited to, polyclonal, monoclonal, chimeric, humanized, single chain, Fab fragments, and fragments produced by an Fab expression library. Numerous methods for producing polyclonal and monoclonal antibodies are known to those of ordinary skill in the art, and can be adapted to produce antibodies specific for the polypeptides of the invention, and/or encoded by the polynucleotide sequences of the invention (see, e.g., Coligan Current Protocols in Immunology Wiley/Greene, N.Y., Paul (ed.) (1991); (1998) Fundamental Immunology Fourth Edition, Lippincott-Raven, Lippincott Williams & Wilkins; Harlow and Lane (1989) Antibodies: A Laboratory Manual, Cold Spring Harbor Press, NY, USA; Stites et al. (Eds.) Basic and Clinical Immunology (4th ed.) Lange Medical Publications, Los Altos, Calif., USA and references cited therein; Goding, *Monoclonal Antibodies: Principles and Practice* (2d ed.) Academic Press, New York, N.Y., USA; 1986; and Kohler and Milstein (1975).

For certain applications, preparation of "humanized" antibodies may be desirable. Methods for the preparation of chimeric (humanized) antibodies are known to those of ordinary skill in the art, and are exemplified e.g., in U.S. Pat. Nos. 4,634,664; 4,634,666; and 5,482,856, each of which is specifically incorporated herein in its entirety by express reference thereto.

In particular embodiments, antibodies, either monoclonal or polyclonal, can specifically bind to at least a first immunogenic peptide or polypeptide as disclosed herein, and particularly those that specifically bind to one or more of the antigenic peptide sequences disclosed in any one of SEQ ID NO:1 through SEQ ID NO:52. Techniques for preparing and characterizing antibodies are well known in the art, particularly with the guidance provided herein. The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Methods for conjugating a polypeptide of the invention to a carrier protein are well known to those of ordinary skill in the art, and include, e.g., glutaraldehyde, m-maleimidobencoyl-N-hydroxysuccinimide ester, carbodiimide and bis-biazotized benzidine, or any combination thereof.

The amount of immunogenic composition used in the production of polyclonal antibodies varies upon the nature of the immunogen as well as the animal used for immunization. Any of the routes disclosed herein can be used to administer the immunogen. The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, specifically incorporated herein in its entirety by express reference thereto. Typically, this technique involves immunizing a suitable animal with a selected immunogen composition, e.g., a purified or partially purified tumor suppressor protein, polypeptide or peptide. The immunizing composition is preferably administered in a manner effective to stimulate antibody-producing cells. Rodents such as mice and rats are preferred animals; however, the use of rabbit, sheep frog cells is also possible. The use of rats may provide certain advantages, but mice are preferred, with the BALB/c mouse being most preferred and most routinely used, as it often gives a higher percentage of stable fusions.

Following immunization, somatic cells with the potential for producing antibodies, specifically B lymphocytes (B cells), are selected for use in the MAb generating protocol. These cells may be obtained from biopsies spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal can then be fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media that support the growth of only the desired fused cells (hybridomas).

Any one of a number of myeloma cells may be used, as are known to those of ordinary skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line, which is widely employed in the art, and known to those of ordinary skill in the antibody field.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described in the art, and those using polyethylene glycol (PEG), such as 37% (vol./vol.) PEG.

Fusion procedures usually produce viable hybrids at low frequencies, about $1\times10^{-6}$ to $1\times10^{-8}$. This does not pose a problem, however, as the viable, fused hybrids are typically differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine, and combinations thereof. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Expression Vectors

The present invention contemplates an expression vector comprising at least one polynucleotide encoding an immunogenic peptide or polypeptide of the present invention. As used herein, the term "operably linked" means that a promoter is connected to a functional nucleic acid sequence in such a way that the transcription of that functional nucleic acid sequence is controlled and regulated by that promoter. Methods for operatively (i.e., operably) linking a promoter to a functional nucleic acid are well known to those of ordinary skill in the molecular biological arts.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Varieties of methods have been developed to operably link nucleic acid segment(s) to a vector via complementary cohesive termini or blunt ends. Such methods are routinely employed in the molecular arts, and are well known to those of ordinary skill in the field. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Liposome-, Nanocapsule-, and Microparticle-Mediated Delivery

In certain embodiments, the inventors contemplate the use of ethosomes, liposomes, lipid complexes, niosomes, phospholipids, nanocapsules, nanospheres, microparticles, microcapsules, microspheres, lipid particles, lipid vesicles, transferosomes, surfactants, and the like, and any combination thereof, for the introduction of the immunogenic compositions of the present invention, or nucleic acids encoding them, into suitable host cells. Preferably, the compositions or acids of the invention are at least substantially, preferably entirely, contained within or bound in association to these dosage forms until delivery to the patient for diagnostic, prophylactic, or therapeutic efficacy Such formulations may also be preferred for introduction of pharmaceutically-acceptable formulations of nucleic acids that encode one or more of the immunogenic peptide compositions disclosed herein. The formation and use of liposomes is generally known to those of ordinary skill in the art, and the use of liposomes, microparticles, nanocapsules and the like have gained widespread use in the targeted delivery of therapeutic compositions to host cells (see, e.g., U.S. Pat. No. 5,741,516, specifically incorporated herein in its entirety by express reference thereto). Further, various methods of liposome and liposome like preparations as potential drug carriers have been reviewed (U.S. Pat. Nos. 5,567,434; 5,552,157; 5,565,213; 5,738,868 and 5,795,587, each of which is specifically incorporated in its entirety by express reference thereto).

Liposomes are formed from phospholipids that are dispersed in an aqueous medium and spontaneously form multilamellar concentric bilayer vesicles (also termed multilamellar vesicles (MLVs). MLVs generally have diameters of from about 25 nm to about 4 µm. Sonication of MLVs results in the formation of small unilamellar vesicles (SUVs) with diameters in the range of about 200 to about 500 Å, containing an aqueous solution in the core. Liposomes bear resemblance to cellular membranes, and are contemplated for use in connection with the present invention as carriers for the immunogenic peptide and polynucleotide compositions described herein. They are widely suitable as both water- and lipid-soluble substances can be entrapped, i.e. in the aqueous spaces and within the bilayer itself, respectively. Liposomes, lipid complexes, and such like may also be employed for site-specific delivery of one or more therapeutic, prophylactic or diagnostic reagents described herein by selectively modifying the liposomal formulation for the particular intended administration.

Phospholipids can form a variety of structures other than liposomes when dispersed in water, depending on the molar ratio of lipid to water. At low ratios, the liposome may be the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

The ability to trap solutes varies between different types of liposomes. For example, MLVs are moderately efficient at trapping solutes, but SUVs tend to be extremely inefficient. SUVs offer the advantage of homogeneity and reproducibility in size distribution, however, and a compromise between size and trapping efficiency is offered by large unilamellar vesicles (LUVs). These are prepared by ether evaporation and can be three to four times more efficient at solute entrapment than MLVs.

Targeting is generally not a limitation in terms of the present invention. Should specific targeting of one or more of the immunogenic compositions be desired; however, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but the other routes of administration described herein may also be used.

Alternatively, the invention provides for pharmaceutically acceptable nanocapsule formulations of the immunogenic compositions of the present invention. Biodegradable polyalkyl-cyanoacrylate nanoparticles that meet these requirements are contemplated for use in the present invention. Such particles may be are easily made, as described (see, e.g., U.S. Pat. No. 5,145,684, specifically incorporated herein in its entirety by express reference thereto).

Additional Modes of Delivery

In addition to the methods of delivery described herein, the following techniques are also contemplated as alternative methods of delivering the disclosed immunogenic compositions, as well as polynucleotides encoding them, to target cells or selected tissues and organs of an animal, and in particular, to cells, organs, or tissues of a vertebrate mammal, and more particularly, to a primate, such as a human being. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), transdermal matrices (U.S. Pat. Nos. 5,770,219 and 5,783,208) and feedback-controlled delivery (U.S. Pat. No. 5,697,899), and each of the patents in this paragraph is specifically incorporated herein in its entirety by express reference thereto.

Biological Functional Equivalents

Modification and changes to the structure of the polynucleotides and polypeptides of the invention may be made to obtain functional variants that possess desirable antigenic characteristics, particularly with respect to improved delivery of therapeutic gene constructs to selected mammalian cell, tissues, and organs for the treatment, prevention, and prophylaxis of various diseases and disorders, as well as methods for the amelioration of symptoms of such diseases. Such modifications may be employed to facilitate the expression of one or more exogenous therapeutic and/or prophylactic polypeptides of interest via methods known to those of ordinary skill in the molecular arts, including, for example, vector-mediated gene therapy. As mentioned above, one of the key aspects of the present invention includes the creation of one or more mutations in specific polynucleotide sequences that encode one or more of the polyvalent immunogenic peptide or polypeptide compositions disclosed herein. In certain circumstances, the resulting peptide or polypeptide sequence is altered by these mutations, or in other cases, the sequence of the peptide or polypeptide is unchanged by one or more mutations in the encoding polynucleotide to produce modified immunogens with improved properties over that afforded by the wild-type sequences.

When it is desirable to alter the amino acid sequence of a polypeptide to create an equivalent, or even an improved, second-generation molecule, the amino acid changes may be achieved by changing one or more of the codons of the encoding DNA sequence, according to Table 3.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with substantially similar or similar or even identical properties. It is thus contemplated that various changes may be made in the polynucleotide sequences disclosed herein, without appreciable loss of biological utility or activity so that a biologically functionally equivalent protein can be obtained.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics, and these indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In making such changes, the substitution of amino acids whose hydropathic indices are within about ±2 is preferred, those that are within about ±1 are particularly preferred, and those within about ±0.5 are more preferred. It is also understood in the art that the substitution of like amino acids can be made effectively on the basis of hydrophilicity. U.S. Pat. No. 4,554,101, specifically incorporated herein in its entirety by express reference thereto, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. As outlined above, amino acid substitutions are generally therefore based on the relative similarity of the amino acid side-chain substituents, for example, their hydrophobicity, hydrophilicity, charge, size, and the like. Exemplary substitutions that take several of the foregoing characteristics into consideration are well known to those of ordinary skill in the art and include arginine and lysine; glutamate and aspartate; serine and threonine; glutamine and asparagine; and valine, leucine and isoleucine.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

The phrase "substantially identical," in the context of two nucleic acids or polypeptides (e.g., antigenic polypeptide sequences, or polynucleotide sequences that encode them) refers to two or more sequences or subsequences that have at least about 90%, preferably 91%, most preferably 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide or amino acid residue identity, when compared and aligned for maximum correspondence, as measured using a sequence comparison algorithm or by visual inspection. Such "substantially identical" sequences are typically considered "homologous," without reference to actual ancestry. With respect to peptides and polypeptides, preferably, "substantial identity" exists over a region of the amino acid sequences that is at least about 10, at least about 20, at least about 30, at least about 40, at least about 50, amino acid residues in length, or more, even up to and including the full length (or nearly the full length) of the two peptide or polypeptide sequences being compared. With respect to polynucleotides encoding such antigenic peptides and polypeptides, preferably, "substantial identity" exists over a region of the nucleic acid sequences that is at least about 30, at least about 60, at least about 90, at least about 120, at least about 150, nucleic acids in length, or more, even up to and including over the full length (or nearly the full length) of the two polynucleotide sequences being compared.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm can then be used to calculate the percent sequence identity for the test sequence(s) relative to the reference sequence, based on the designated program parameters.

Optimal alignment of sequences for comparison can be conducted, e.g., by the local homology algorithm (see e.g., Smith and Waterman, 1981), by the homology alignment algorithm (see e.g., Needleman and Wunsch, 1970), by the search similarity comparison method (see e.g., Pearson and Lipman, 1988), by computerized implementations of algorithms such as GAP, BESTFIT, FASTA, and TFASTA in the Wisconsin Genetics Software Package, Genetics Computer Group, Madison, Wis., USA, or by visual inspection.

One example of an algorithm that is suitable for determining percent sequence identity and sequence similarity is the BLAST algorithm (Altschul et al., 1990) and BLOSUM62 scoring matrix (see, e.g., Henikoff and Henikoff, 1989). Software for performing BLAST analyses is publicly available through the National Center for Biotechnology Information (www.ncbi.nlm.nih.gov/). In addition to calculating percent sequence identity, the BLAST algorithm also performs a statistical analysis of the similarity between two sequences (see, e.g., Karlin and Altschul, 1993). Another example of a useful sequence alignment algorithm is the PILEUP program, which creates a multiple sequence alignment from a group of related sequences using progressive, pairwise alignments. It can also plot a tree showing the clustering relationships used to create the alignment. PILEUP uses a simplification of the progressive alignment comparison method (see e.g., Feng and Doolittle, 1987). The method used is similar to the method described by Higgins and Sharp (1989).

DEFINITIONS

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range. As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin. An antigen generally encompasses any immunogenic substance, i.e., any substance that elicits an immune response (e.g., the production of specific antibody molecules) when introduced into the tissues of a susceptible animal, and that is capable of specifically binding to an antibody that is produced in response to the introduction of the antigen. An antigen is capable of being recognized by the immune system, inducing a humoral immune response, and/or inducing a cellular immune response leading to the activation of B- and/or T-lymphocytes. An antigen may include a single epitope, or two or more epitopes. An antigen may include one or more native or synthetic immunogenic components, and may optionally be administered in, or with, one or more adjuvants or any other embodiment disclosed herein.

As used herein, the term "antibody" refers to a protein that binds to other molecules (antigens) via heavy and light chain variable domains, $V_H$ and $V_L$, respectively. The term "antibody" refers to any immunoglobulin molecule, including, for example, but not limited to, IgM, IgG, IgA, IgE, IgD, and any subclass thereof or combination thereof. The term "antibody" also means a functional fragment of immunoglobulin molecules, including for example, but not limited to, Fab, Fab', $(Fab')_2$, Fv, Fd, scFv and sdFv fragments unless otherwise expressly stated. For example, the term "M2 antibody" or "anti-M2 antibody," as used herein, means an antibody that specifically binds to an M2 protein or a portion (epitope) thereof.

As used herein, an "antigenic polypeptide" or an "immunogenic polypeptide" is a polypeptide which, when introduced into a vertebrate, reacts with the vertebrate's immune system molecules, i.e., is antigenic, and/or induces an immune response in the vertebrate, i.e., is immunogenic. Examples of antigenic and immunogenic polypeptides of the present invention include, but are not limited to, e.g., HA, NP, PB1, PB2, NS1, NS2, M1, NA, PA, M2 including the extracellular fragment of M2 (M2e), or any of the foregoing polypeptides or fragments or variants thereof. Isolated antigenic and immunogenic polypeptides of the present invention in addition to those encoded by polynucleotides of the invention, may be provided as a recombinant protein, a purified subunit, a viral vector expressing the protein, or may be provided in the form of an inactivated influenza virus vaccine, e.g., a live-attenuated virus vaccine, a heat-killed virus vaccine, etc.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal. The use of one or more delivery vehicles for chemical compounds in general, and peptides and epitopes in particular, is well known to those of ordinary skill in the pharmaceutical arts. Except insofar as any conventional media or agent is incompatible with the active ingredient, its use in the diagnostic, prophylactic, and therapeutic compositions is contemplated. One or more supplementary active ingredient(s) may also be incorporated into, or administered in association with, one or more of the disclosed immunogenic compositions.

As used herein, the term "circulating" refers to microbes that exist in the natural, wild, host population for that microbe and may be isolated commonly from present host populations. In some embodiments, circulating may refer to microbes that once existed in wild host populations but that have since become rare or extinct in present host populations. Bird Flu (H5N1), for example, is a microbe presently circulating within avian populations worldwide, but it does not widely circulate amongst humans, whereas the pandemic Spanish Flu virus was a microbe that was circulating in 1918, but is not known to be circulating presently. Circulating viruses, such as the H1N1 and H3N2 viruses presently circulating in human populations, are distinguished from "laboratory viruses," which are defined as having been changed (i.e., genetically engineered or mutated) through human intervention.

As used herein, "conservation" and "conserved" relate to the resistance of sequences, or subsequences within sequences, of nucleotides or preferably polypeptides to antigenic shift and drift over time, e.g., from year to year. In preferred embodiments of the present invention, conservation over time indicates a decreased degree of reassortment and number, or significance, of point mutations and other mutations in selected polypeptides and, preferably, in peptide sequences of the present invention as compared with a mutation rate for remaining portions of polypeptides or proteins from which the selected polypeptides were selected. In some embodiments, it may be considered that vaccines prepared with target antigens having given peptide sequences, wherein those given peptide sequences show a greater conservation of the amino acid sequence of homologous virion subunit components, i.e., antigen epitope structures, across a greater range of virion strains, subtypes, or types, the greater the effect of single-course vaccinations. In general, such a vaccine is expected to be broader in protective range than a conventional vaccine. Due to a general correlation between non-immunodominance and sequence conservation, however, the broadest vaccine may also be expected to be less protective against one or more strains on a "per epitope" basis. Using repeated peptide sequences (i.e., increasing the number of epitopes) effectively compensates for this difference. In certain embodiments, a conserved region generally maintains an invariant peptide or nucleotide sequence over time. Conserved regions may contain conservative mutations that do not affect the functionality of the polypeptide or polynucleotide or, in the case of epitopes, the ability of that epitope to stimulate an immune response in a host. In certain embodiments, a "conservative" amino acid alteration is defined as one that does not produce a significantly adverse effect on the overall physical and/or biological or immunogenic properties of the polypeptide. In some embodiments, conserved regions provide the same or substantially the same, biological functionality over time. Because conserved epitopes are resistant to mutagenic change, the immunogenic nature of the epitope can be maintained.

As used herein, the term "epitope" refers to that portion of a given immunogenic substance that is the target of, i.e., is bound by, an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, for example, Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

As used herein, the term "expression" refers to the biological production of a product encoded by a coding sequence. In most cases, a polynucleotide (i.e., DNA) sequence, including the coding sequence, is transcribed to form a messenger-RNA (mRNA). The messenger-RNA is then translated to form a polypeptide product that has a relevant biological activity. The process of expression may involve further processing steps to the RNA product of transcription, such as splicing to remove introns, and/or post-translational processing of a polypeptide product.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, a "heterologous" is defined in relation to a predetermined referenced gene sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, the term "homology" refers to a degree of complementarity between two polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

As used herein, "homologous" means, when referring to polypeptides or polynucleotides, sequences that have the same essential structure, despite arising from different origins. For example, the M2 protein of Influenzaviruses is highly conserved across Influenza A virus serotypes despite viral shifts and drifts, and so is considered a homologous protein within that group. Further, Influenzavirus proteins M1 and M2 have different functions but have homologous fragments or portions that have the same structure; those portions of M1 and M2 are homologous. Typically, homologous proteins are derived from closely related genetic sequences, or genes. By contrast, an "analogous" polypeptide is one that shares the same function with a polypeptide from a different species or organism, but has a significantly different form to accomplish that function. Analogous proteins typically derive from genes that are not closely related.

The term "host cell" means a cell that contains one or more heterologous polypeptide(s) or and/or polynucleotide(s). Host cells can be prokaryotic cells such as E. coli, or eukaryotic cells such as yeast, insect, amphibian, avian or mammalian cells, including, for example, but not limited to, human cells. Exemplary host cells include, e.g., but are not limited to, African green monkey kidney cells (e.g., Vero cells) baby hamster kidney (BHK) cells, Chinese hamster ovary (CHO) cells, primary chick kidney (PCK) cells, Madin-Darby canine kidney (MDCK) cells, Madin-Darby bovine kidney (MDBK) cells, 293 cells, COS cells, and the like. Culture and propagation of such cells are within the purview of the person of ordinary skill in the art, particularly based on the guidance herein as to the invention.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

As used herein, the terms "immunize" or "immunization" or similar terms refer to conferring the ability to mount a substantial immune response against a target antigen or epitope as it is expressed on a microbe or as the isolated epitope or antigen. These terms do not necessarily require complete immunity, but rather that an immune response be produced that is substantially greater than baseline, e.g., where immunogenic compositions of the invention are not administered or where a conventional (influenza) vaccine is administered. For example, a mammal is considered to be immunized against a target antigen, if the cellular and/or humoral immune response, preferably a substantial response, to the target antigen occurs following the application of compositions of the invention or according to methods of the invention.

As used herein, the term "immunological response" to a composition or vaccine denotes the development of a cellular and/or antibody-mediated immune response in the host animal. Generally, an immunological response includes (but is not restricted to) one or more of the following effects: (a) the production of antibodies; (b) the production of B cells; (c) the production of helper T cells; and/or (d) the production of cytotoxic T cells, that are specifically directed to a given antigen or hapten.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc.

As used herein, the term "immunogenic" as used herein also refers to an amino acid sequence, or a portion of an amino acid sequence within a protein, polypeptide, or peptide that elicits an immunological response in a host animal.

As used herein, the term "immunogenic protein," "immunogenic peptide," or "immunogenic polypeptide" refers to proteins, peptides, and polypeptides that are immunologically active in the sense that once administered to the host, it is able to evoke an immune response of the humoral and/or cellular type directed against the protein. Preferably, the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The phrases "isolated" or "biologically pure" refer to material that is substantially, or essentially, free from components that normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, electrostatic bonding, and such like.

The term "pathogen" is defined herein as any sort of infectious agent, including e.g., viruses, prions, protozoans, parasites, as well as microbes such as bacteria, yeast, molds, fungi, and the like.

"Different," when referring to microbes or microbial particles, is defined herein to include both different species of microbes as well as different individual examples or instances of the same species. For exemplary purposes, combinations of different viruses will be discussed. Exemplary microbes include viruses such as influenza, other orthomixoviruses, rhinovirus, and chicken pox viruses, for example, or any other infectious virus.

As used herein, the term "monoclonal," when used in reference to an antibody, refers to an antibody that is based upon, obtained from or derived from a single clone, including any eukaryotic, prokaryotic, or phage clone. The term monoclonal antibody is often abbreviated "MAb" in the singular, and "MAbs" in the plural.

As used herein, the terms "M2," "M2 protein," "M2 peptide," "M2 sequence" and "M2 domain" are used interchangeably to refer to all or a portion of an M2 protein sequence (e.g., a subsequence such as the extracellular domain) isolated from, based upon or present in any naturally occurring or artificially produced influenza virus strain or isolate. Thus, the term M2 and the like include naturally occurring M2 sequence variants produced by mutation during the virus life-cycle or produced in response to a selective pressure (e.g., drug therapy, expansion of host cell tropism or infectivity, etc.), as well as recombinantly or synthetically produced M2 sequences. Corresponding definitions apply for the "M1," "M1 protein," "M1 sequence" and "M1 domain." Corresponding definitions also apply for the HA and NA protein subunits.

As used herein, the term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

As used herein, the term "patient" (also interchangeably referred to as "host" or "subject") refers to any host that can receive one or more of the pharmaceutical compositions disclosed herein. Preferably, the subject is a vertebrate animal, which is intended to denote any animal species (and preferably, a mammalian species such as a human being). In certain embodiments, a "patient" refers to any mammalian host, including but not limited to, human and non-human primates, bovines, canines, caprines, cavines, corvines, epines, equines, felines, hircines, lapines, leporines, lupines, murines, ovines, porcines, racines, vulpines, and the like, including livestock, zoological specimens, exotics, as well as companion animals, pets, and any animal under the care of a veterinary practitioner. A patient can be of any age at which the patient is able to respond to inoculation with the present vaccine by generating an immune response. In particular embodiments, the mammalian patient is preferably human.

The phrase "pharmaceutically-acceptable" refers to molecular entities and compositions that do not produce an allergic or similar untoward reaction when administered to a mammal, and in particular, when administered to a human. As used herein, "pharmaceutically acceptable salt" refers to a salt that retains the desired biological activity of the parent compound and does not impart any undesired toxicological effects. Examples of such salts include, but are not limited to, acid addition salts formed with inorganic acids, for example, hydrochloric acid, hydrobromic acid, sulfuric acid, phosphoric acid, nitric acid, and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N'-dibenzylethylenediamine or ethylenediamine; and combinations thereof.

As used herein, the term "plasmid" refers to a construct that is composed of genetic material (i.e., nucleic acids). Typically, a plasmid contains an origin of replication that is functional in bacterial host cells, e.g., *Escherichia coli*, and selectable markers for detecting bacterial host cells comprising the plasmid. Plasmids of the present invention may include genetic elements as described herein arranged such that an inserted coding sequence can be transcribed and translated in eukaryotic cells. In addition, the plasmid may include a sequence from a viral nucleic acid. Such viral sequences, however, are normally not sufficient to direct or allow the incorporation of the plasmid into a viral particle, and the plasmid is therefore a non-viral vector. In certain embodiments described herein, a plasmid is a closed circular DNA molecule.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Throughout the disclosure, common one-letter and three-letter amino acid abbreviations have been employed following the conventional nomenclature in the art: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained. All amino-acid residue sequences represented herein conform to the conventional left-to-right amino-terminus to carboxy-terminus orientation.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. Furthermore, the term is also intended to include enzymes, i.e., functional biomolecules comprising at least one amino acid polymer. Polypeptides and proteins of the present invention also include polypeptides and proteins that are or have been post translationally modified, and include any sugar or other derivative(s) or conjugate(s) added to the backbone amino acid chain.

As used herein, a "protective immune response" or "therapeutic immune response" refers to a CTL and/or an HTL response to an antigen, which in some way prevents or at least partially arrests disease, or the symptoms, side effects or progression thereof. The immune response may also include an antibody response that has been facilitated by the stimulation of helper T cells.

As used herein, the term "repeat" or "repeated" means recited or presented again. In accordance with the present invention, one or more peptide sequences are repeated in the target antigen at least one additional time, i.e., present twice, preferably at least three times, and more preferably at least four times. These are also referred to herein as repeated twice (i.e., present twice), repeated three times (i.e., present three times), etc. In some variations, the number of repeats is limited by the maximum physical size of the target antigen that is beneficial to use in the subject or impedes immune function in the subject. In other words, the maximum number of repeating segments, i.e., the maximum number of repeats of individual peptide sequences or the number of different peptide sequences, or both, is limited to the point at which delivery of the antigen is negatively affected, or the prophylactic and/or therapeutic effect of the antigen is negatively affected.

The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide chains, "sequence" and "subsequence" have similar meanings relating to the 5' to 3' order of nucleotides.

As used herein, the term "substantially homologous" encompasses sequences that are similar to the identified sequences such that antibodies raised against peptides having the identified sequences will react with peptides having the substantially homologous sequences. In some variations, the amount of detectable antibodies induced by the homologous sequence is identical to the amount of detectable antibodies induced by the identified sequence. In other variations, the amounts of detectable antibodies induced are substantially similar, thereby providing immunogenic properties. For example, "substantially homologous" can refer to at least about 75%, preferably at least about 80%, and more preferably at least about 85% or at least about 90% identity, and even more preferably at least about 95%, more preferably at least about 97% identical, more preferably at least about 98% identical, more preferably at least about 99% identical, and even more preferably still, at least substantially or entirely 100% identical (i.e., "invariant").

As used herein, the term "vaccine" refers to a composition or formulation that contains a composition of the present invention and that is in a form that is capable of being administered to any vertebrate, preferably an animal, preferably a mammal, and more preferably a human. Typically, the vaccine includes or is prepared from dry powder in a conventional saline or buffered aqueous solution medium in which the composition of the present invention is suspended or dissolved. In this form, the composition of the present invention can be used conveniently to prevent, manage or otherwise treat a condition or a symptom thereof. Upon introduction into a host, the vaccine is able to provoke an immune response, preferably a detectable immune response, including, but not limited to, the production of antibodies, cytokines and/or the activation of cytotoxic T cells, antigen presenting cells, helper T cells, dendritic cells and/or other cellular responses. The vaccine of the present invention includes influenza peptide sequences, preferably conserved influenza peptide sequences, and more preferably repeated conserved influenza peptide sequences. Vaccines of the present invention may include or be administered in or with an adjuvant or in association with any other carrier noted herein.

The vaccines and immunogenic compositions of the present invention confer an immune response to a patient after immunization. As used herein, the term "immune response" refers to a humoral immune response and/or cellular immune response leading to the activation or proliferation of B- and/or T-lymphocytes. In some instances, however, the immune responses may be of low intensity and become detectable only when using at least one substance in accordance with the invention. The term "adjuvant" refers to an agent used to stimulate the immune system of a living organism, so that one or more functions of the immune system are increased and directed towards the immunogenic agent.

As used herein, the terms "treatment," "treat," "treated," or "treating" refer to therapy or the amelioration of one or more symptoms of a disease, or the reduction in the extent or severity of disease, or a symptom thereof, whether before or after its development afflicts a patient. When used with respect to an infectious disease, for example, the terms refer to a treatment or treatment regimen that decreases the severity of the infection or decreases or lessens or delays one or more symptoms of illness attributable to the infection, as well as increasing the ability of the infected individual to fight the infection, including e.g., the reduction and/or elimination of the infection from the body of the individual, or to lessen or prevent the disease from becoming worse.

As used herein, "mammal" refers to the class of warm-blooded vertebrate animals that have, in the female, milk-secreting organs for feeding the young. Mammals include without limitation humans, apes, many four-legged animals, whales, dolphins, and bats. A human is a preferred mammal for purposes of the invention.

The term "immunogenically-effective amount" has its usual meaning in the art, i.e., an amount of an immunogen that is capable of inducing an immune response that significantly engages pathogenic agents that share immunological features with the immunogen. This term can also encompass either therapeutic or prophylactic effective amounts, or both.

As used herein, the terms "prevention," "vaccination," or "preventing" refer to the prophylaxis or to the partial or complete inhibition of infection, or to the reduction or delay in the onset, of one or more diseases, or one or more symptoms thereof, in a subject that may be predisposed to it, but has not yet been exposed to it or been diagnosed as having it. When used with respect to an infectious disease, for example, the terms refer to a prophylactic administration of one or more of the immunogenic peptides of the invention, which tends to increase the resistance of a subject to infection with a pathogen or, in other words, decreases the likelihood that the subject will become infected with the pathogen or, if infected, will delay symptoms, decrease the severity of the infection, or decrease symptoms of illness attributable to the infection, or any combination thereof.

Each of "preventing" and "treating" include managing a particular infection, disease, condition, or symptom thereof, in a patient, as well as any beneficial modification of candidate status or the course of the disease or condition, or any symptoms thereof. The managing may address some or all of the symptoms thereof with or without actually affecting the underlying infection or any disease or condition resulting therefrom.

The term "recombinant" indicates that the material (e.g., a polynucleotide or a polypeptide) has been artificially or synthetically (non-naturally) altered by human intervention. The alteration can be performed on the material within or removed from, its natural environment or state. Specifically, e.g., an influenza virus is recombinant when it is produced by the expression of a recombinant nucleic acid. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

As used herein, the term "variant," when used in the context of a polynucleotide or polypeptide, refers to a polynucleotide or polypeptide that differs from the wild-type polynucleotide or polypeptide by way of one or more nucleotide or amino acid mutation(s), substitution(s), insertion(s), deletion(s), or any combination thereof. Depending on the context, the term "mutant" is also used to denote a variation from the wild-type polynucleotide or polypeptide sequence. The mutant may arise naturally (i.e., the mutation therein occurring in nature), be random, spontaneous, or specifically engineered by the hand of man in a given polynucleotide or polypeptide sequence. Protein or peptide variants often typically include the exchange of one or more native amino acid(s) for (an) other amino acid(s) at one or more amino acid residues within the protein or peptide.

The term "e.g.," as used herein, is used merely by way of example, without limitation intended, and should not be construed as referring only those items explicitly enumerated in the specification.

In accordance with long standing patent law convention, the words "a" and "an" when used in this application, including the claims, denotes "one or more."

It should also be understood generally that, with respect to any of the components herein, e.g., antigen, peptide, polysaccharide, etc., that these terms include a portion thereof that can be less than or equal to the whole, as well as include combinations of the same or different types.

EXAMPLES

The following examples are included to demonstrate illustrative embodiments of the invention. It should be appreciated by those of ordinary skill in the art that the techniques disclosed in the examples that follow represent techniques discovered to function well in the practice of the invention, and thus can be considered to constitute preferred modes for its practice. However, those of ordinary skill in the art should, in light of the present disclosure, appreciate that many changes can be made in the specific embodiments which are disclosed and still obtain a like or similar result without departing from the spirit and scope of the invention.

Example 1

Priming Study

Figure 3:
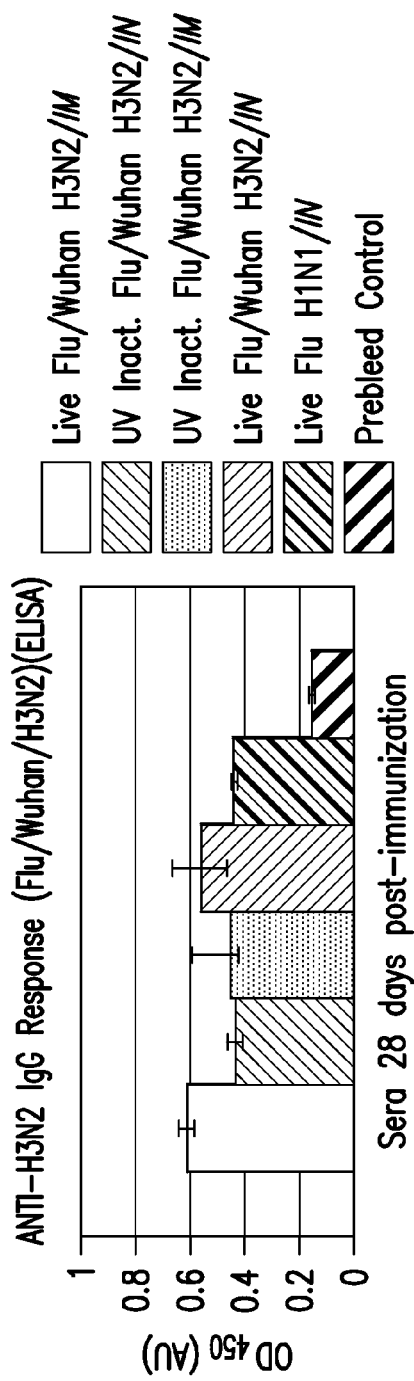
FIG. 3 is a graphic illustration of an anti-H3N2 IgG response in sera 28 days after initial priming (immunization) of test groups with intranasal or intramuscular influenza H3N2 or live intramuscular H1N1.

This vaccine model was intended to identify methods to, and to assess the capacity of different antigens to induce immunity and to prime influenza immunity prior to heterologous or homologous boosting. Cotton rats were administered whole live or inactivated (H3N2 or H1N1) virus intranasally as a respiratory infection. Live H3N2 virus was given intramuscularly (IM), and inactivated H3N2 was administered both IM and intranasally (IN). Live H1N1 virus was administered solely IN to enable a comparison of antibody responses. Complete Freund's adjuvant (CFA) was co-administered in selected cases. The "H3N2 plate" measured enzyme-linked immunosorbent assay (ELISA) for IgG against live H3N2 virus as shown in FIG. 3. The "H1N1 plate" measured ELISA for IgG against live H1N1 virus as shown in FIG. 4.

Intramuscular immunization with live virus may be as good as live intranasal or other novel priming approaches described herein, and may also be useful for immunization as well.

Figure 4:
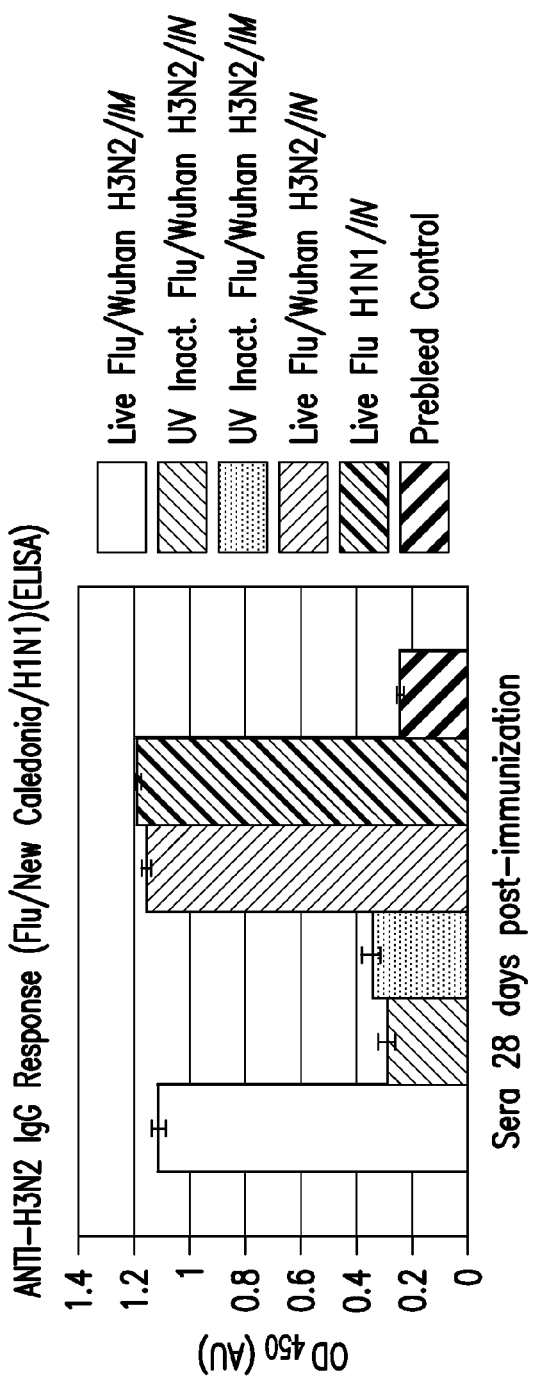
FIG. 4 is a graphic illustration of an anti-H1N1 IgG response in sera 28 days after initial priming (immunization) of test groups with intranasal (IN) or intramuscular (IM) influenza.

As shown in FIG. 3 and FIG. 4, the results indicated that live virus provided a good IgG response at 28 days' post-challenge with both live H3N2 and live H1N1 virus. Live virus vaccine also elicited enhanced cross-reacting antibody (Ab) production. That is, inactivated vaccine induced production of good homologous IgG, but the Ab was less cross-reactive.

Example 2

Vaccination using PF2001 and M2e Peptides Against Influenza H3N2 in Cotton Rats Using Conserved Peptide Immunogens A 39-amino acid (aa) synthetic peptide (designated herein "PF2001", and also referred to alternatively herein as "Peptide 5906" or "SEQ ID NO:44") was produced and administered to test subjects as described. This vaccine was constructed utilizing two overlapping peptide sequences from M2e and T-cell epitope sequence from C. tetani toxin. The final product was a synthetic fusion polypeptide containing two distinct M2 epitopes, i.e., peptide sequences, recognized by IgG MAbs, and one T-cell epitope sequence. PF2001 was synthesized using standard SPPS, which was scalable for increased production capability. The primary amino acid sequence of this immunogenic 39-aa peptide is SLLTEVET-PIRNEWGLLTEVETPIRYIKANSKFIGITE (SEQ ID NO:44). Test compounds for this study also included the complete M2e peptide sequence; both were administered at a target concentration of 0.2 mg/ml.

The general in vivo protocol for analysis of the boosting study for PF2001 is shown below:

| Day | Procedure |
| --- | --- |
| 0 | 1. 28 young adult Hispid cotton rats (*Sigmodon hispidus* 6-8 weeks old) were divided into 7 groups of 4 animals each. All animals were ear tagged and pre-bled. |
| | Animal Groups    Immunize/Boost (admin. Route) |
| | 1      100 µg CFA-Adjuvanted PF2001 (x2 IM) |
| | 2      100 µg PF2001 in PBS (x2 IM) |
| | 3      Live (Wuhan) H3N2 (IN)/100 µg CFA-Adjuvanted PF2001 (IM) |
| | 4      UV-Inactivated H3N2 (IM)/100 µg CFA-Adjuvanted PF2001 (IM) |
| | 5      100 µg CFA-Adjuvanted M2e (x2 IM) |
| | 6      UV-Inactivated H3N2 (x2 IM) |
| | 7      Live (Wuhan) H3N2 (x2 IN) |
| | Immunize all animals all animals with the indicated preparations as above. |
| 14 | 2. All animals were eye bled. |
| 21 | 3. All animals were eye bled. |
| 28 | 4. All animals were boosted with indicated preparations, and eye bled. |
| 35 | 5. All animals were eye bled. |
| 42 | 6. All animals were terminally bled and sacrificed. |

IM = intramuscular administration.
IN = intranasal administration.

Figure 5:
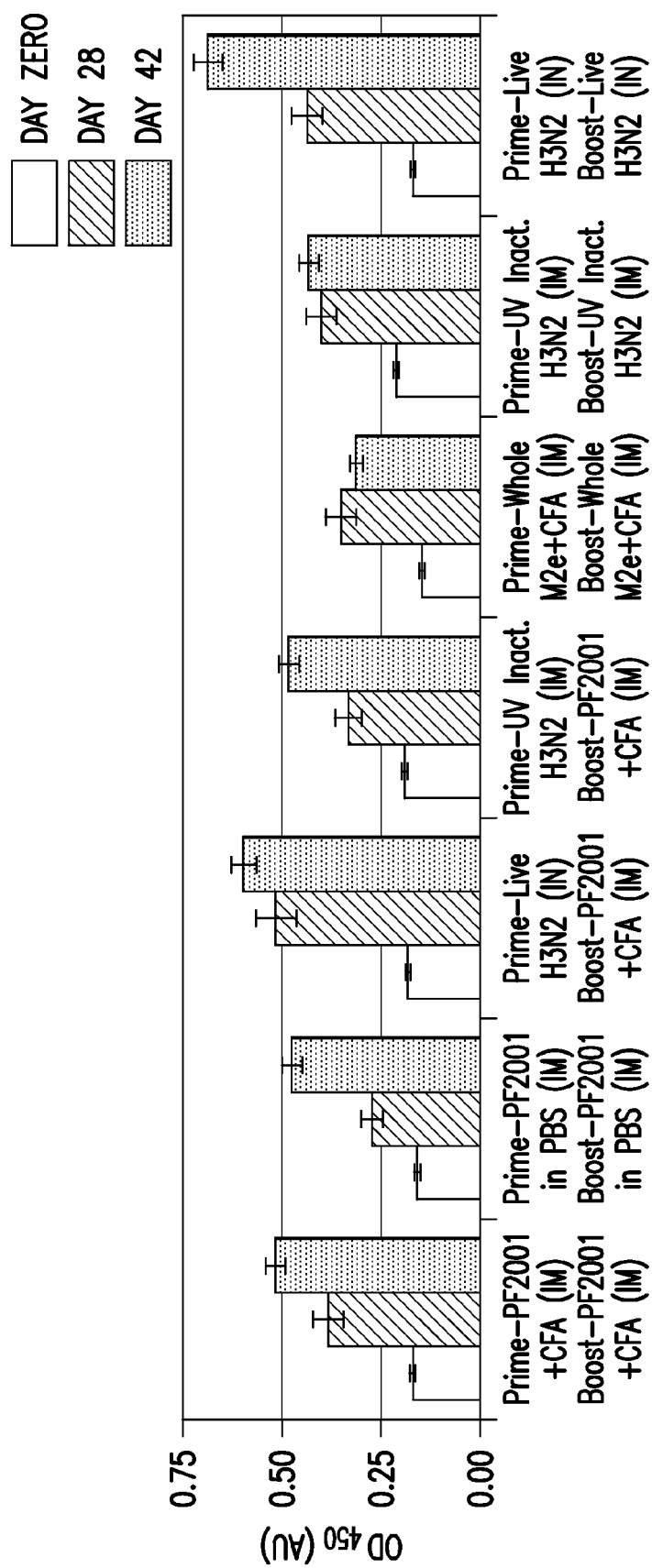
FIG. 5 is a graphic illustration of the IgG response to live H3N2 in experimental groups over time, in accordance with certain embodiments of the present invention, and particularly as described in Example 2.
Figure 6:
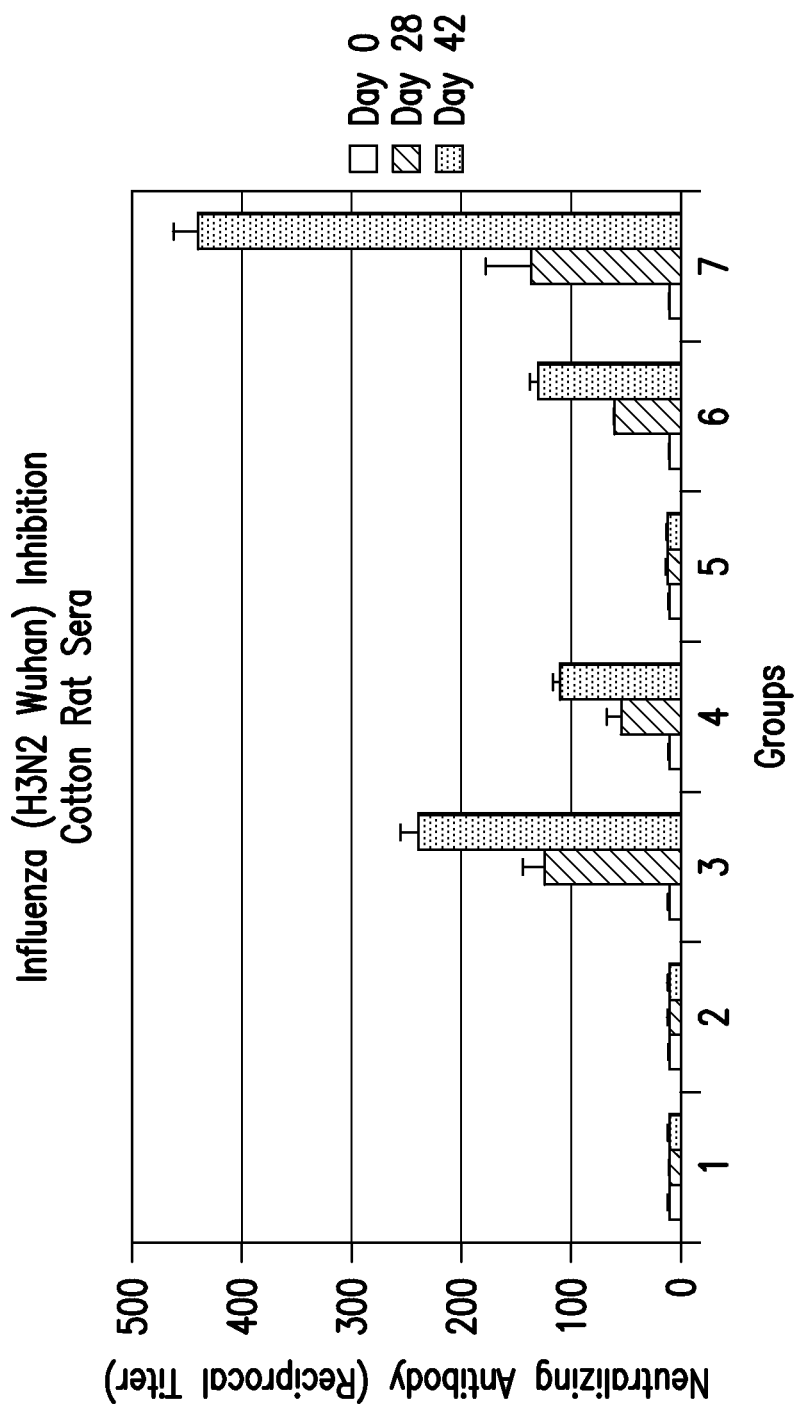
FIG. 6 is a graphic illustration of the amount of neutralizing antibody present in response to Influenza H3N2 (Wuhan) in the experimental groups over time, in accordance with certain embodiments of the present invention, and it shows that the PF2001 antigenic peptide boosts production of virus-inhibiting antibodies.
Figure 10A:
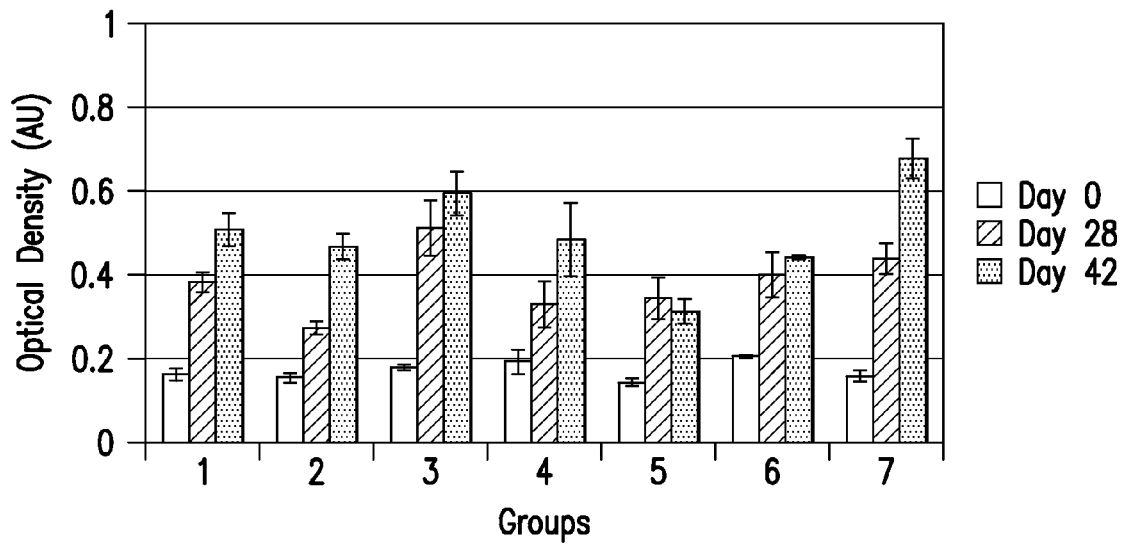
FIG. 10A and FIG. 10B show the vaccination results using PF2001 and M2e peptide against influenza A virus (H3N2) according to the invention.
Figure 10B:
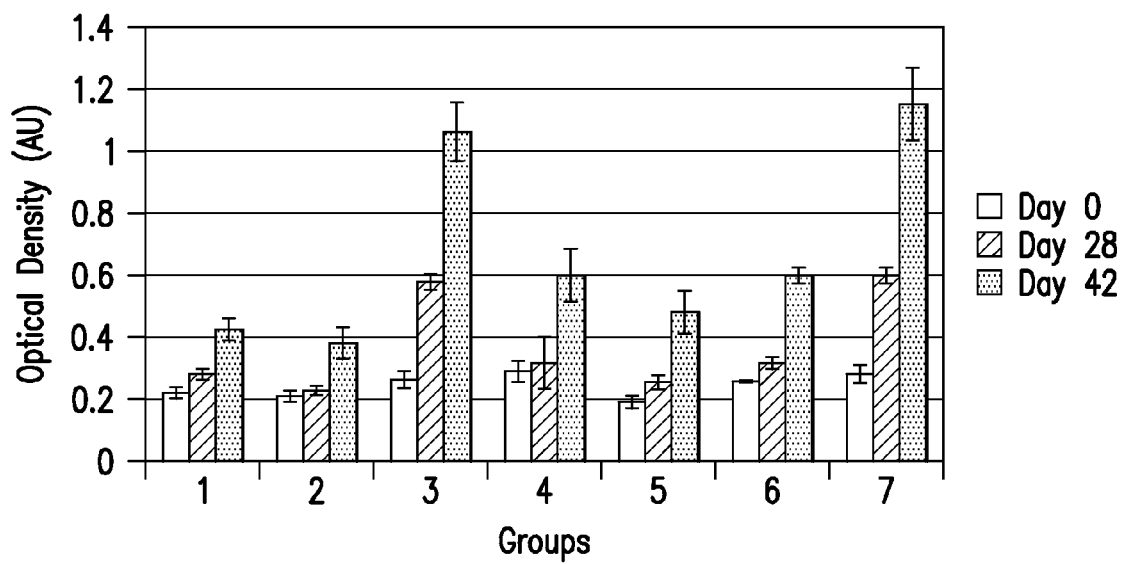

Test subjects, young adult cotton rats, were divided into 7 groups of four subjects for dosing as noted above. Animals were ear-tagged and pre-bled at time intervals as required, such as once per week. All animals were immunized with the test compounds as indicated on day 0 (FIG. 10A and FIG. 10B). A second immunization (or infection challenge) was given 28 days after initial priming as noted (FIG. 5). Group 1 rats were primed with primed with 100 µg CFA-adjuvanted PF2001 (IM) on day 0, and boosted with 100 µg CFA-adjuvanted PF2001 (IM) on day 28. Group 2 rats were primed with primed with 100 µg PF2001 in phosphate-buffered saline (PBS) (IM) on day 0, and boosted with 100 µg PF2001 in PBS (IM) on day 28. Group 3 rats were immunized with live influenza virus H3N2 (Wuhan) (IN) on day 0, and boosted with CFA-adjuvanted PF2001 (IM) on day 28. Group 4 rats were immunized with ultraviolet (UV)-inactivated influenza virus H3N2 (Wuhan) (IM) and boosted with 100 µg CFA-Adjuvanted PF2001 (IM) on day 28. Group 5 rats were primed with 100 µg CFA-Adjuvanted M2e (IM) on day 0, and boosted with 100 µg of CFA-Adjuvanted M2e (IM) on day 28. Group 6 rats were immunized with UV-inactivated influenza virus H3N2 (Wuhan) (IM) on day 0, and challenged with the same virus (IM) on day 28. Group 7 rats were immunized with live influenza virus H3N2 (Wuhan) (IN) on day 0, and challenged with the same virus (IN) on day 28.

Sera from each animal group were obtained to analyze antibody response at days 14, 21, 28, 35, and 42. IgG titers to live H3N2 virus were measured using ELISA, and the results at day 0, day 28 and day 42 are shown in FIG. 5, FIG. 10A, and FIG. 10B: IgG levels were detected in all peptide groups (1 and 2). PF2001 in PBS or conjugated to CFA X2 generated a similar titer to group 6 (inactivated H3N2 given IM). On day 42 cross-reactivity was detected from the peptide groups with group 4 (inactivated H3N2 IM priming, when boosted with 100 µg PF2001 in CFA) having equivalent titer to group 6 by day 42.

Figure 11A:
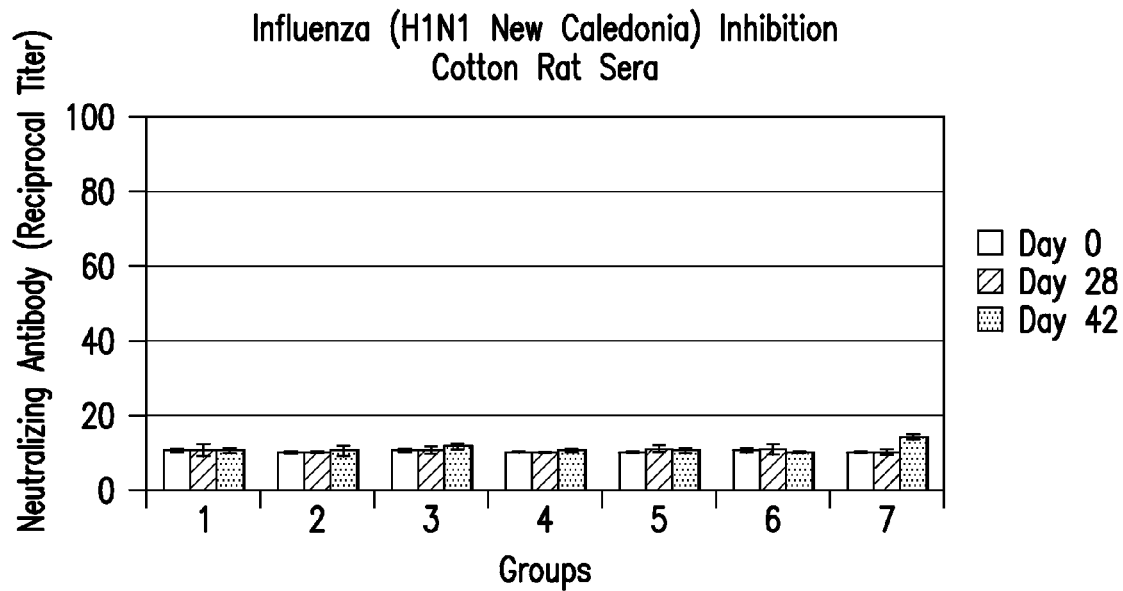
FIG. 11A and FIG. 11B show vaccination results for animal groups 1 to 7 at day 0, 28, and 42 for influenza A virus H1N1 New Calcdonia (FIG. 11A) and H3N2 Wuhan (FIG. 11B) in cotton rat sera according to the invention.
Figure 11B:
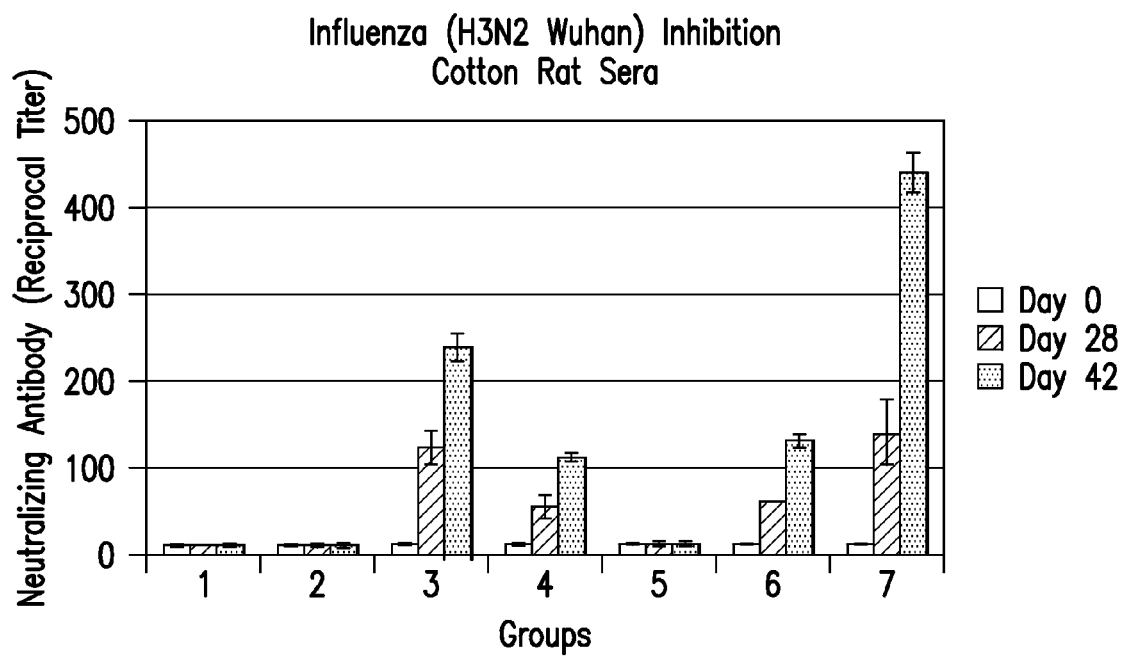
Figure 12:
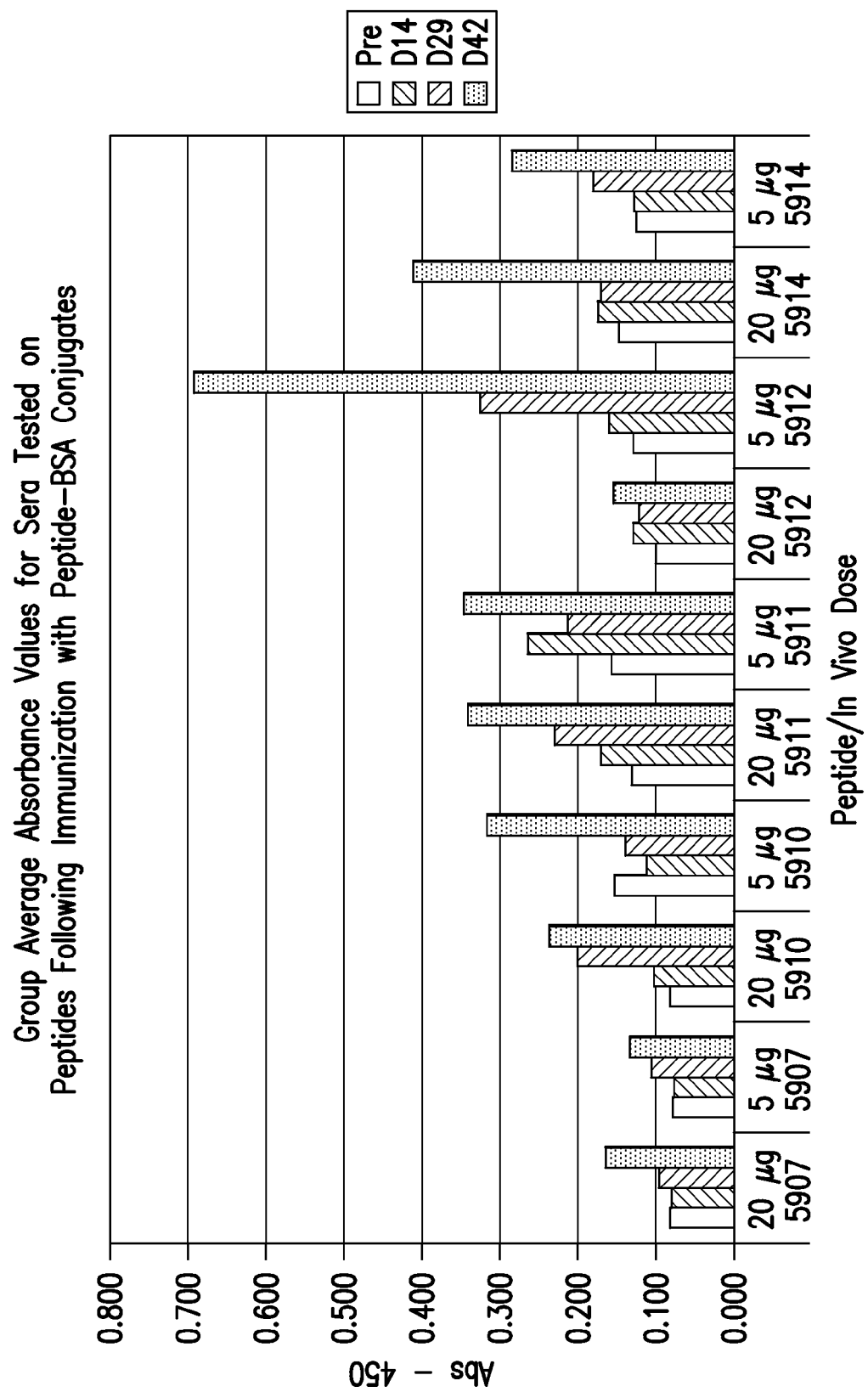
FIG. 12 is a graphic illustration of the effects of antigenic peptide dose on group average absorbance values for sera tested on BSA-conjugated peptide Nos. 5907, 5910, 5911, 5912 and 5914 according to the invention.
Figure 13:
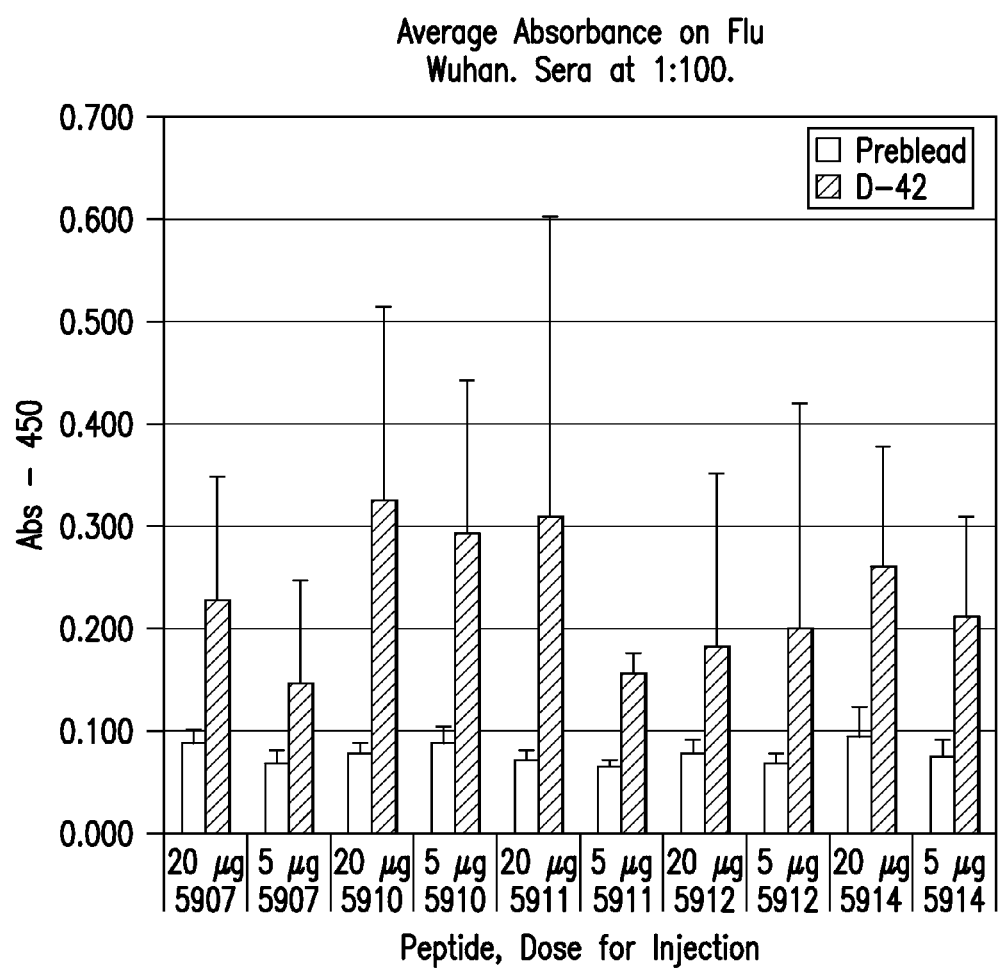
FIG. 13 is a graphic illustration of the effects of antigenic peptide dose on group average absorbance values for flu Wuhan (sera 1:100) comparing pre-bleed vs. day 42 values according to the invention.
Figure 14:
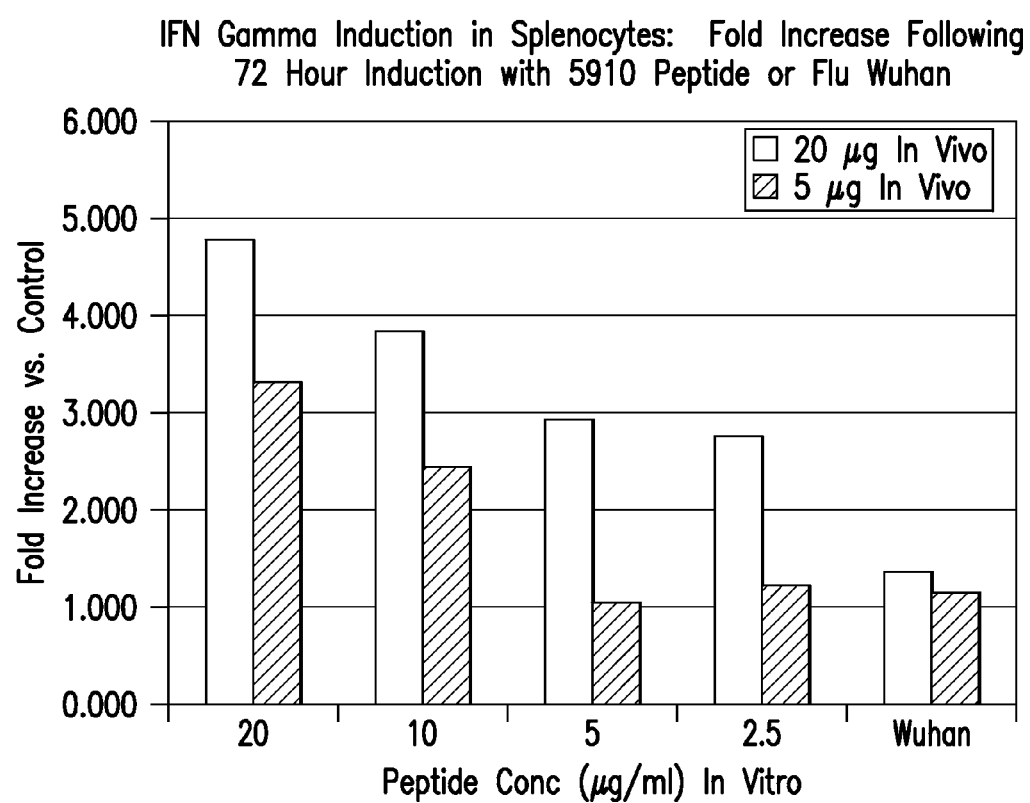
FIG. 14 is a graphic illustration of INF-Gamma induction in splenocytes (expressed as fold increase following 72 hr induction with Peptide 5910 or Flu Wuhan) comparing 5- or 20-µg in vitro administration according to the invention.
Figure 15:
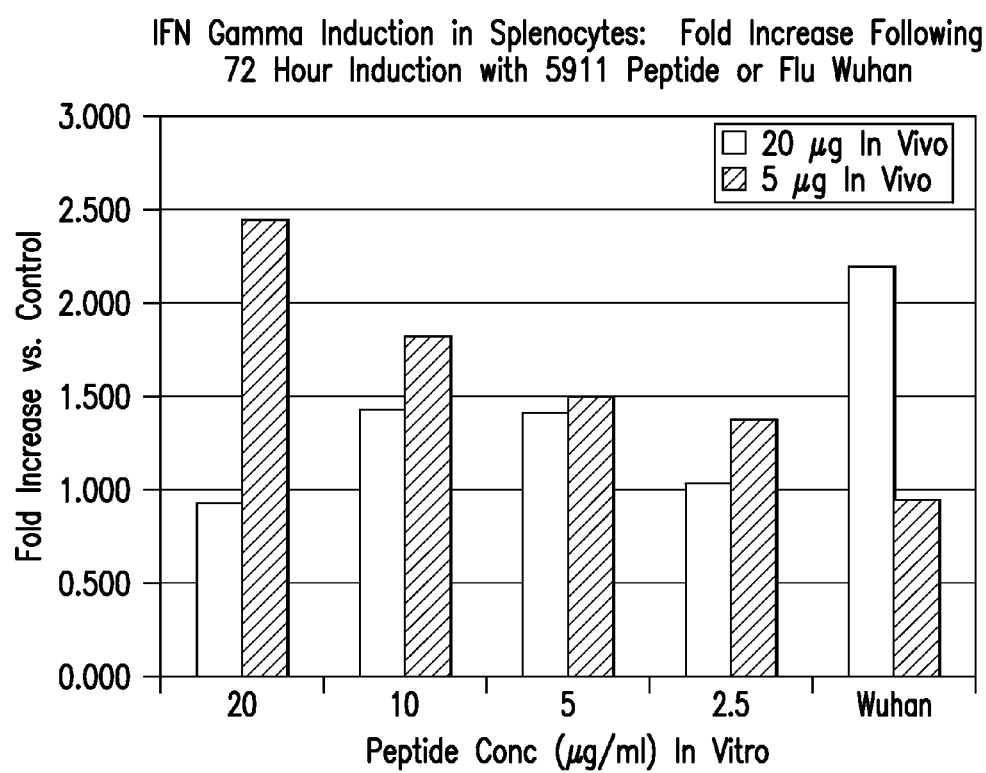
FIG. 15 is a graphic illustration of INF-Gamma induction in splenocytes (expressed as fold increase following 72 hr induction with Peptide 5911 or Flu Wuhan) comparing 5- or 20-µg in vitro administration dose according to the invention.
Figure 16:
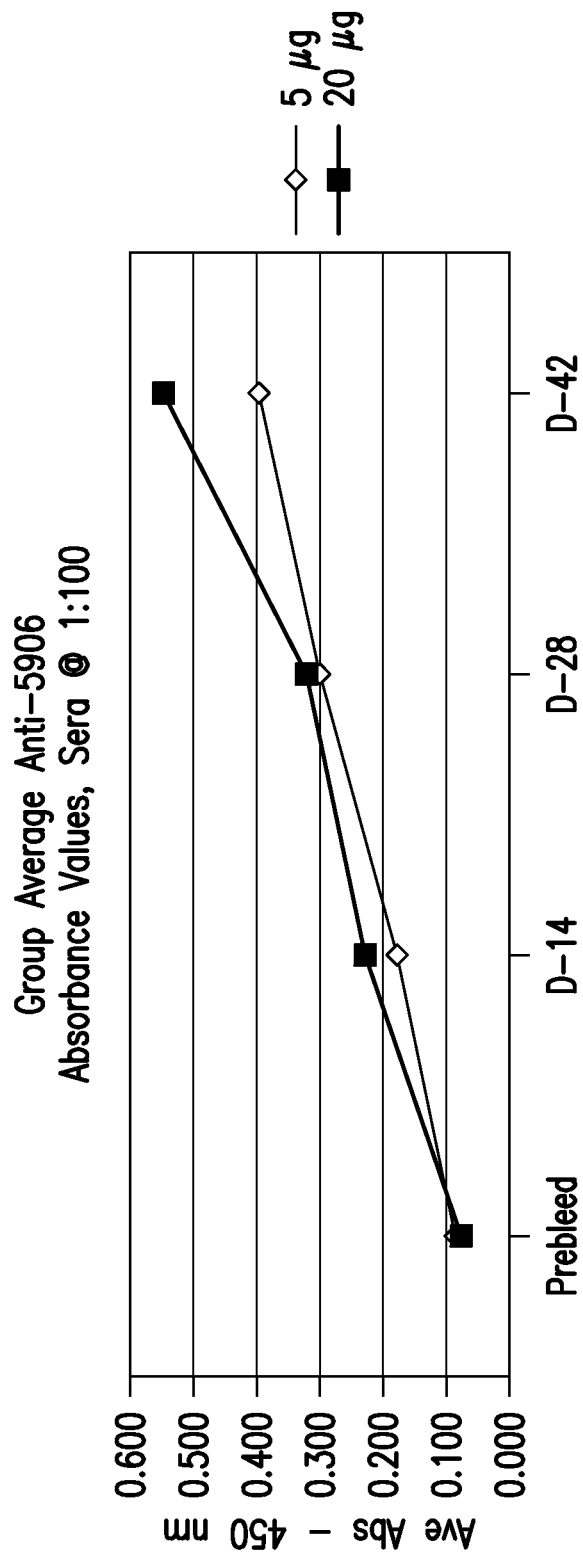
FIG. 16 is a graph of group average anti-PF2001 absorbance values (Sera 1:100) comparing 5- or 20-µg in vitro administration dose at day 0, 14, 28, and 42 according to the invention.

As shown in FIG. 5 and FIG. 11B, two doses of the small synthetic influenza peptide vaccine (PF2001) produced a rise in neutralizing IgG antibody that recognized native M2 epitopes on live H3N2 virus (H3N2 plate) after each immunization. Thus, this small, synthetically-produced peptide vaccine induced antibodies that were able to recognize and bind to native epitopes on the M2 antigen of live influenza viruses. In addition, this small synthetic peptide was immunogenic and raised antibody in primed and unprimed animals even in the absence of an adjuvant. Two doses of PF2001 antigen were superior to two injections of M2e for inducing IgG that could bind to live H3N2 virus. These data suggest that overlapping epitopes create a duplication of certain epitopes and may enhance antibody induction to the epitope repeats. IgG antibody rises were also induced against live H1N1 virus, further demonstrating that the small synthetic M2e vaccine-induced IgG antibodies that bind to M2 epitopes on live influenza virus and cross subtypes with different HA and NA proteins.

Further as shown in FIG. 5, PF2001 was also able to boost immunity in animals that had previous influenza respiratory infection or had a previous inactivated whole virus though intramuscular immunization. While two live H3N2 respiratory infections, i.e., challenges, created the greatest rise in IgG antibodies to influenza, it was surprising that peptide vaccine boosting after influenza viral infection was similar to two live respiratory H3N2 exposures.

The PF2001 peptide vaccine boosted viral inhibitory antibody to H3N2 in animals previously infected with H3N2. In addition, inhibitory antibody titers were also boosted in animals that had been previously immunized with inactivated H3N2 vaccine.

These studies demonstrated that a synthetic peptide vaccine having a unique sequence not found in nature could induce immunity to influenzavirus across strains or serotypes that had non-identical HA and NA primary amino acid sequences. In addition, these induced antibodies inhibited influenzavirus replication in vitro and recognized epitopes on live influenzavirus, which it inactivated. Importantly, in exemplary studies, the peptide vaccine PF2001 was administered effectively, both with and without adjuvant, and was shown to provide enhanced immunity with as few as one or two doses of the peptide vaccine. Furthermore, these studies demonstrated that non-native synthetic peptides could successfully be used as a booster in previously primed individuals, i.e., those who have had an influenzavirus illness or were administered either an inactivated influenza vaccine intramuscularly or live influenza virus/vaccine intranasally, and that the PF2001 immunogenic composition could boost influenzavirus inhibitory titers in vivo.

As shown in FIG. 1B, neutralizing antibodies against Influenza H3N2 (Wuhan) were generated on day 28 and day 42 post-boost. At the titers tested (1:100 dilution), neutralizing antibodies were not detected against H1N1 (data not shown). On day 28, neutralizing antibodies were detected in groups 3, 4, 6, and 7 (FIG. 11B), where intranasal inoculations with live influenza generated the highest titers, as compared to inactivated influenza delivered intramuscularly. For serum samples obtained at day 42, increased levels of neutralizing antibodies were detected in groups 3, 4, 6, and 7 with the greatest response in group 7 (primed on day 0 and boosted on day 28 with live H3N2 virus). Thus, live immunogens may be better for immunization and priming using peptide or other immunogen-based vaccines.

Serum IgG antibodies induced in cotton rats by this conserved peptide bound to native epitopes as expressed on live influenzavirus of two different serotypes. Surprisingly, the small linear fragments that comprise PF2001 also induced strong binding to native influenzavirus peptide epitopes; moreover, both priming and a boosted response were achieved using PF2001 whether the peptide was administered in saline alone, or adjuvanted to CFA. These studies demonstrated that PF2001 was capable of eliciting an immune response in a mammal to both H3N2 and H1N1, either with or without adjuvanting the peptide.

Live H3N2 given by the intranasal route (intranasal immunization or respiratory viral infection, "IN") resulted in higher serum IgG levels at day 28 compared to inactivated whole virus (inactivated influenza vaccine immunization) injected intramuscularly ("IM") as determined by ELISA conducted on days 0, 28, and 42. While both regimens primed for peptide vaccine boost with the conserved peptide vaccine, live IN priming was better than inactivated virus given by IM immunization. These results demonstrated that a synthetic peptide vaccine of the invention can also be used to effectively boost the immune response from a prior conventional vaccine. The immune response seen with PF2001 was similar to that observed using a booster immunization with whole inactivated virus, or a conventional inactivated influenzavirus vaccine.

Cotton rats immunized IM with the whole M2e molecule when adjuvanted with CFA provided no particular advantage over small epitopic peptide fragments in inducing IgG to native proteins of live influenzavirus. It was surprising that a peptide vaccine using small fragments of the whole M2e molecule synthesized in a non-native form, induced IgG antibodies to native epitopes on the live organism, even without adjuvant, and had a better boost effect when compared with the boost provided by the native M2e sequence. These data suggest that conserved epitopes arranged in novel patterns not seen in native microbes can effectively or more effectively generate an immune response in a subject than conventional vaccines using native proteins and sequences, and can be synthesized with another microbial peptide (e.g., the T-cell epitope of tetanus toxoid).

Example 3

Poly HA Epitope Antigen

A polymicrobial target antigen was prepared by SPPS having the following amino acid sequence (hyphens separating selected peptide sequences are inserted for the reader's convenience and do not represent constituents of the peptide): GNLFIAP-GNLFIAP-QYIKANSKFIGITE-GNLFIAP (also referred to herein as "Peptide 5907"; SEQ ID NO:15). This 35-aa target antigen includes a repeated HA modified epitope (GNLFIAP, also referred to herein as "Peptide 5910"; SEQ ID NO:5) combined with a tetanus T-cell stimulating epitope (QYIKANSKFIGITE, SEQ ID NO:53). A vaccine prepared from the synthetic polypeptide raises an immune response against both Influenza H1N1, H3N2, and H5N1 following administration to test subjects as a primary vaccine or as a booster following priming with live virus (infection), whole virus vaccine, or synthetic peptide vaccine.

Example 4

Poly NA Epitope Antigen

A polymicrobial target antigen having the following sequence was prepared by SPPS (hyphens separating selected peptide sequences are inserted for the reader's convenience and do not represent constituents of the peptide): HYEECSCY-DWSGYSGSFVQHPELTGL-HYEECSCY-QYIKANSKFIGITE (also referred to herein as "Peptide 5908"; SEQ ID NO:16). This target antigen includes a first repeated NA-derived epitopic peptide (HYEECSCY, also referred to herein as "Peptide 5911"; SEQ ID NO:7) interspersed with a second NA-derived epitopic peptide (DWSGYSGSFVQHPELTGL, also referred to herein as "Peptide 5912"; SEQ ID NO:11) linked to a tetanus T-cell stimulating epitopic peptide (QYIKANSKFIGITE, SEQ ID NO:53). A vaccine prepared from the synthetic peptide raised an immune response against Influenza H1N1, H3N2, and H5N1 strains following administration to test subjects either as a primary vaccine or as a booster following priming with live virus (infection), whole virus vaccine, or synthetic peptide vaccine.

Example 5

Poly-HA, NA, and M2 Epitope Antigenic Peptides

A polymicrobial target antigen having the following sequence was prepared by SPPS (hyphens separating selected peptide sequences are inserted for the reader's convenience and do not represent constituents of the peptide): GNLFIAP-GNLFIAP-HYEECSCY-HYEECSCY-QYIKANSKFIGITE-HYEECSCY-TPIRNE-TPIRNE (SEQ ID NO:14). This target antigen comprises repeated selected HA-, NA-, and M2-derived peptide sequences combined with a tetanus T-cell stimulating epitope. A vaccine prepared from the synthetic polypeptide raised an immune response against both Influenza H1N1, H3N2, and H5N1 following administration to test subjects as a primary vaccine or as a booster following priming with live virus (infection), whole virus vaccine, or synthetic peptide vaccine.

Example 6

Poly-Epitopic Viral/Bacterial Antigens and Conjugates

In addition to the prevention and treatment of viral and other microbial diseases (and particular influenza) alone, the present invention also encompasses antigenic compositions, vaccines, and compositions comprising them that include two or more epitopic sequences, each of which is from a distinct organism.

Figure 17:
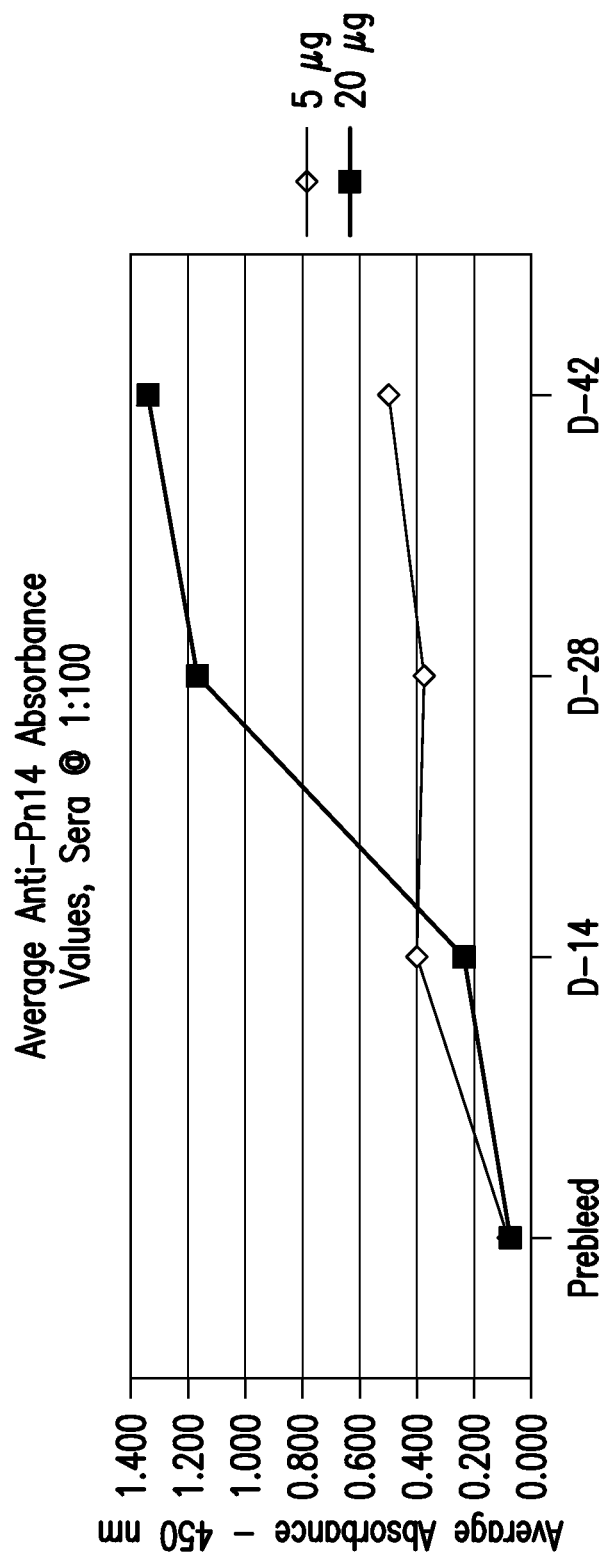
FIG. 17 is a graph of group average anti-Pn14 absorbance values (Sera 1:100) comparing 5- or 20-µg in vitro administration dose at day 0, 14, 28, and 42 according to the invention.
Figure 18:
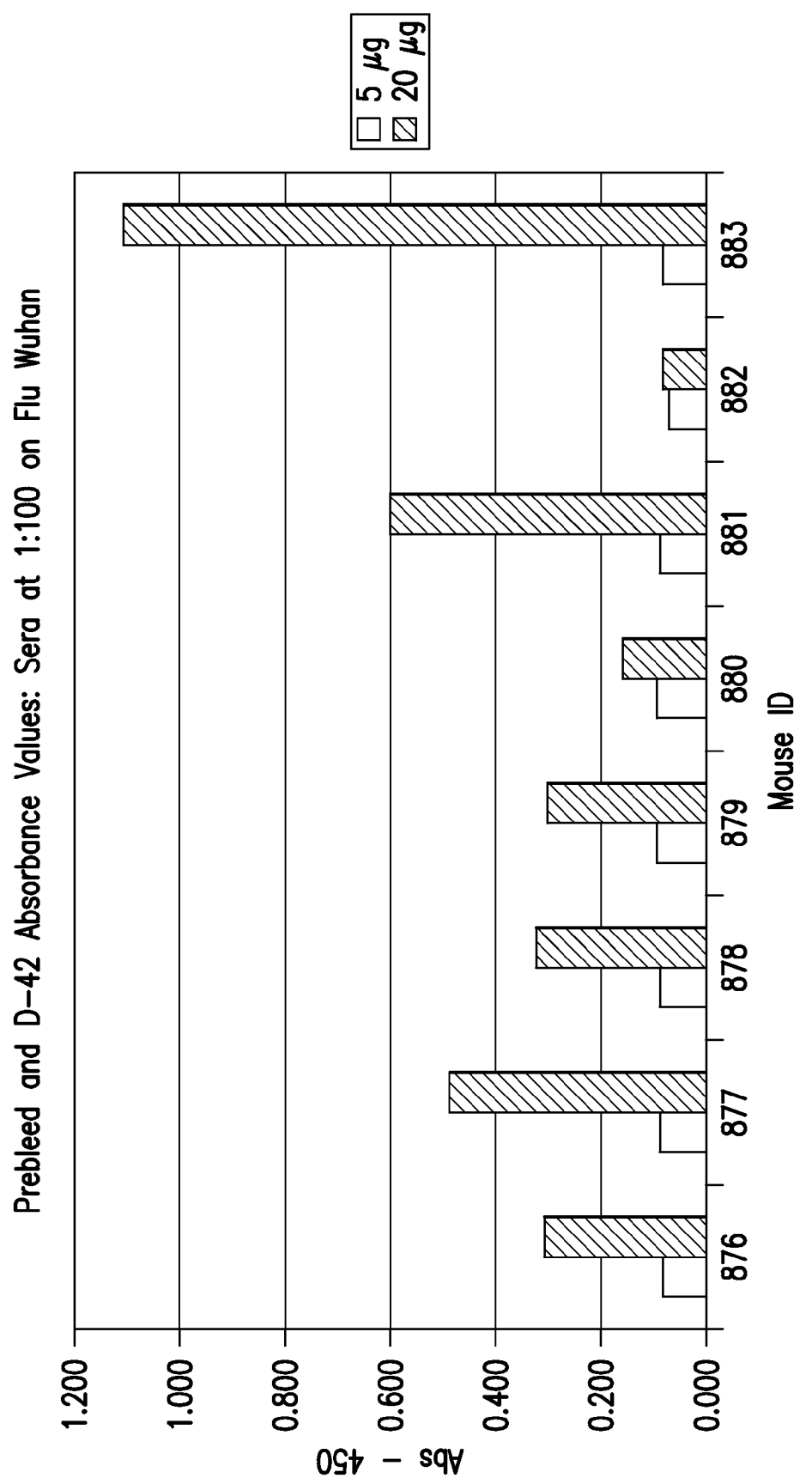
FIG. 18 is a graph of the absorbance values for eight individual mice for anti-Flu Wuhan (Sera 1:100) comparing 5- or 20-µg in vitro administration dose at day 0 and 42 according to the invention.
Figure 19:
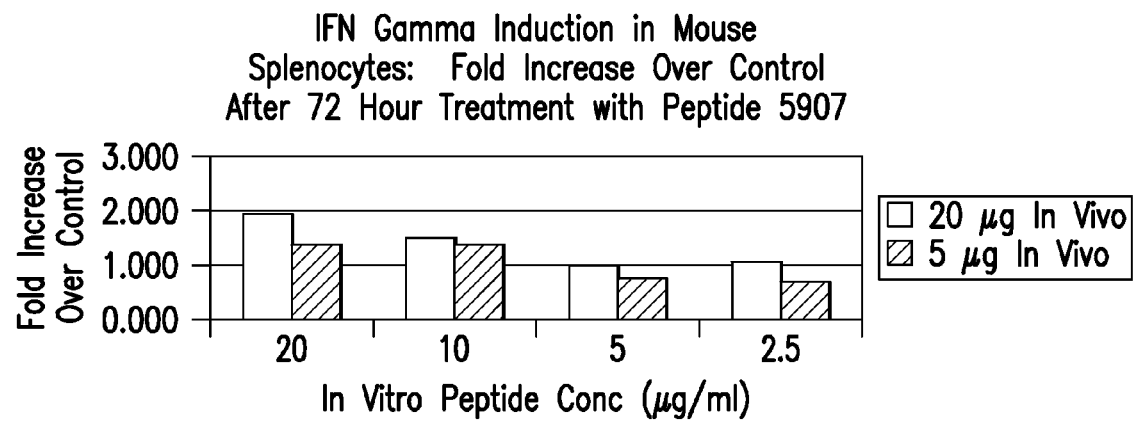
FIG. 19 shows INF-γ induction mouse splenocytes shows as a fold-increase over control after 72 hr treatment with Peptide 5907 vs. in vitro peptide concentration comparing 5- or 20-µg in vivo administration doses according to the invention.
Figure 20:
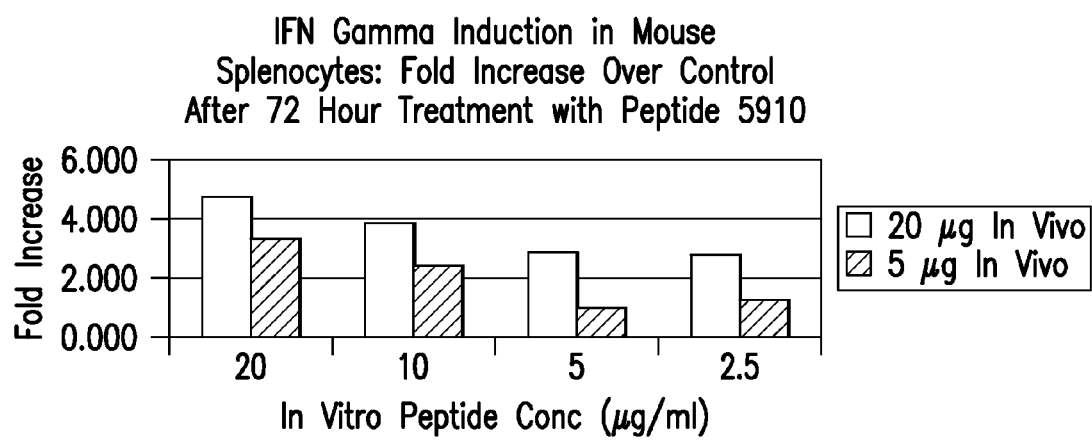
FIG. 20 shows INF-γ induction mouse splenocytes shows as a fold-increase over control after 72 hr treatment with Peptide 5910 vs. in vitro peptide concentration comparing 5- or 20-µg in vivo administration doses according to the invention.
Figure 21:
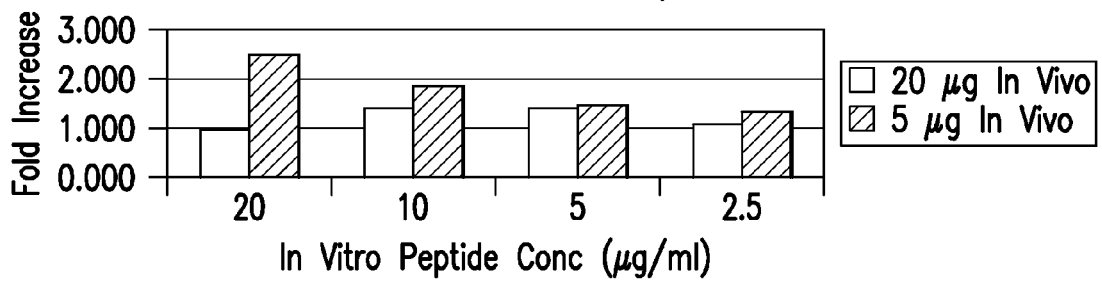
FIG. 21 shows INF-γ induction mouse splenocytes shows as a fold-increase over control after 72 hr treatment with Peptide 5911 vs. in vitro peptide concentration comparing 5- or 20-µg in vivo administration doses according to the invention.
Figure 22:
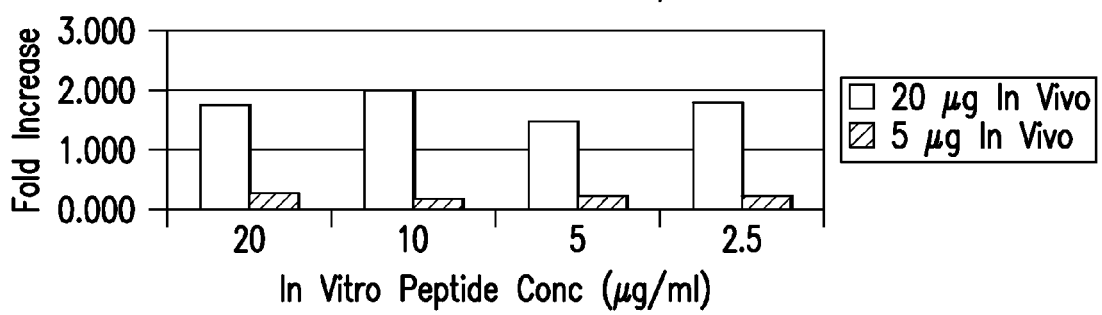
FIG. 22 shows INF-γ induction mouse splenocytes shows as a fold-increase over control after 72 hr treatment with Peptide 5912 vs. in vitro peptide concentration comparing 5- or 20-µg in vivo administration doses according to the invention.
Figure 23:
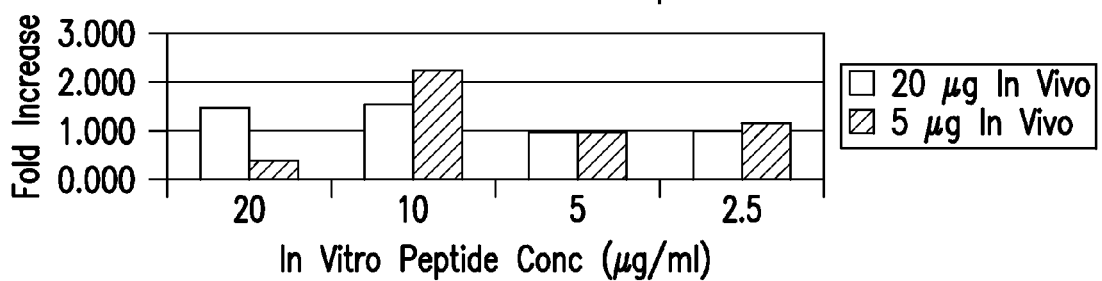
FIG. 23 shows INF-γ induction mouse splenocytes shows as a fold-increase over control after 72 hr treatment with Peptide 5914 vs. in vitro peptide concentration comparing 5- or 20-µg in vivo administration doses according to the invention.
Figure 24:
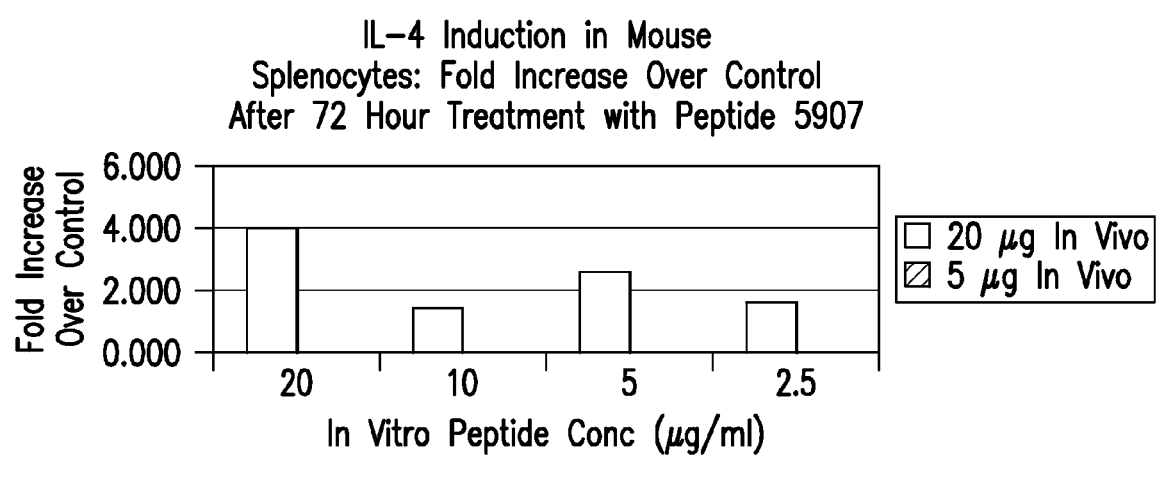
FIG. 24 shows IL-4 induction mouse splenocytes shows as a fold-increase over control after 72 hr treatment with Peptide 5907 vs. in vitro peptide concentration comparing 5- or 20-µg in vivo administration doses according to the invention.
Figure 25:
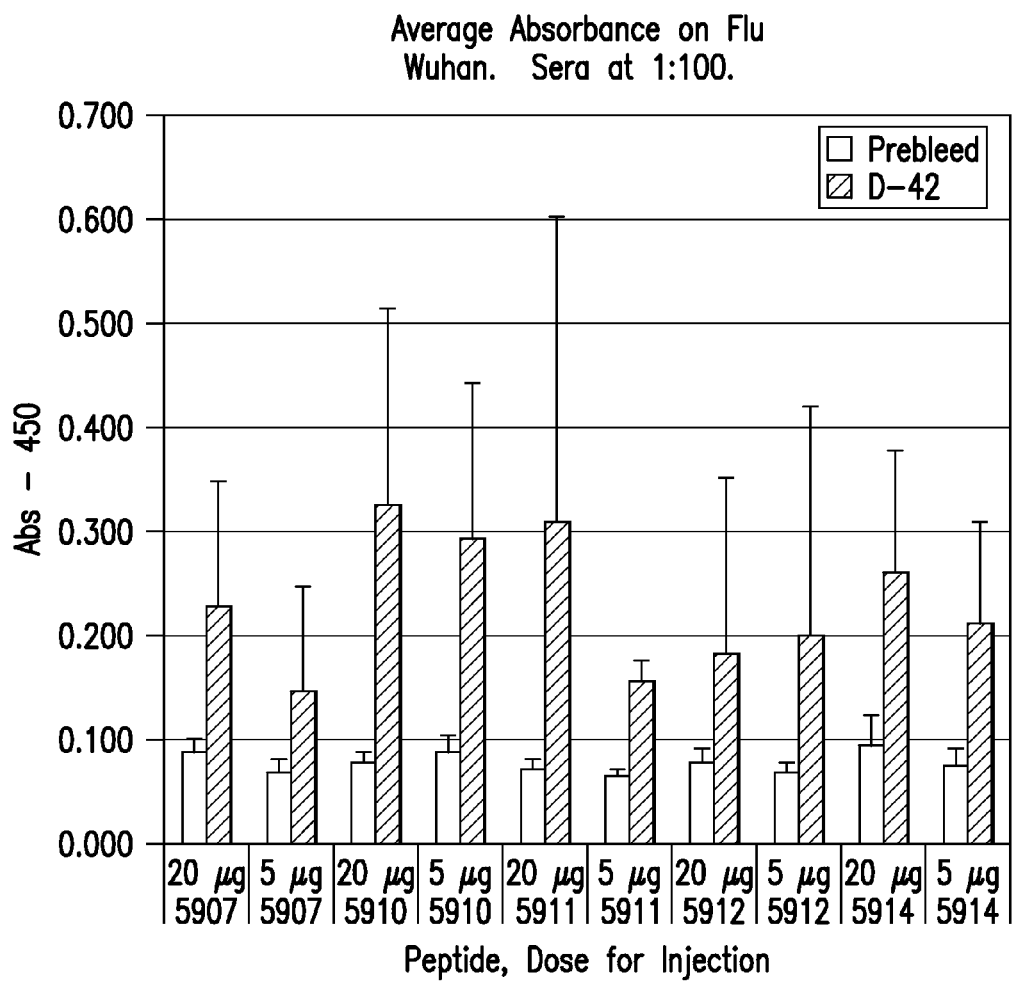
FIG. 25 illustrates the results of average absorbance of pre-bleed and day 42 values obtained for flu Wuhan with sera at 1:100 dilution using five of the antigenic peptide compositions disclosed herein, Peptide 5907, 5910, 5911, 5912 and 5914 according to the invention.

The present example demonstrates that PF2001 peptide could be successfully conjugated to type 14 pneumococcal polysaccharide, and the resulting vaccine induced antibody to both pneumococcus and influenza. A 20-μg dose induced a strong anti-type 14 pneumococcus response at day 28 and day 42 (FIG. 17), and both 5- and 20-μg doses induce anti-influenzavirus antibodies that bind to native antigens on live H3N2 virus (Table 12). Some mice with a 20-μg dose developed very high titers. These data showed that a conserved epitope vaccine that included both bacterial and viral epitopes can be conjugated to produce a multimeric polymicrobial vaccine. Experimental Protocol:

| Day | Procedure |
|---|---|
| 0 | 1. Ear Tag, Pre-bleed and primary immunization Group A, 5 μg/mouse; Group B, 20 μg/mouse. Immunizations were IM in PBS with 60% Titermax Gold ®. |
| 14 | 2. All animals were eye bled. |
| 28 | 3. All animals were boosted with indicated preparations, and eye bled. |
| 42 | 4. All animals were terminally bled and sacrificed. 5. Culture of splenocytes pooled by group. 6. Cultures treated with antigenic peptide. |
| 45 | 7. Harvest supernatants for later evaluation of IFN-γ and IL-4. |

All serum samples were stored at −80° C. All supernatant samples were stored at −20° C. A hybrid antigen can be further prepared as follows: PIA can be isolated from *S. aureus* strain MN8m as described in PCT Publ. No. WO 2004/43407 (specifically incorporated herein in its entirety by express reference thereto) and sized by chemical cleavage to 50 kDa as described in PCT Publ. No. WO 2003/53462 (specifically incorporated herein in its entirety by express reference thereto). The 50-kDa PIA and the CAP antigen are conjugated to type 14 pneumococcal polysaccharide (alternatively, *H. influenzae* type B polyribose phosphate [PRP] may be used) using the amino-oxy method described in U.S. Pat. Appl. Publ. No. 2005/0169941 (specifically incorporated herein in its entirety by express reference thereto). This target antigen includes repeated HA and NA epitopic peptide sequences from influenzavirus linked to a *Staphylococcus aureus* polysaccharide PIA, a pneumococcal (or, alternatively, *Haemophilus influenzae*) polysaccharide, combined with a tetanus T-cell stimulating epitope.

A vaccine prepared from this polyvalent target antigen-conjugate can raise an immune response against three strains of influenza H1N1, H5N1, and H3N2, as well as to the bacterial species, *S. aureus*, *H. influenzae*, and *Pneumococcus* spp. following administration to test subjects as a primary vaccine or as a booster following priming with live virus (infection), whole virus vaccine, or synthetic peptide vaccine.

Example 6.1

Conjugates of BSA Protein and Influenza Peptide

Serum samples from individual mice, tested at a 1:100 dilution, in general showed an increase in absorbance when comparing pre-bleed values to those obtained with day 42 sera (Table 1). However, the increases were generally modest. Seven of the sera had increases of 3-fold or greater and one, mouse 930 (immunized with 5 μg of peptide conjugated to BSA) had an absorbance value of 1.758 on day 42. The group average values are shown in Table 2.

A comparison of responses on Day 42 is presented in Table 3.

As observed with the anti-peptide antibody assay, the absorbance values using live influenza virus generally increased from the pre-bleed to day 42 (Table 3). The absorbance values for fourteen of the mice increased by at least 3-fold, including six of the eight mice immunized with Peptide 5910 (SEQ ID NO:5) conjugated to BSA.

The results of numerous characterization of a number of immunogenic peptides are summarized in the following Tables and the figures appended hereto. As noted for the Wuhan ELISA, the strongest IFN-γ response was observed with supernatants from the Peptide 5910 group (SEQ ID NO:5). Weaker responses were obtained with other peptides, notably Peptide 5911 (SEQ ID NO:7). Except for the cells from the Peptide 5907 (SEQ ID NO:15) group, no detectable IL-4 was found in any supernatants, regardless of the dilution, in vivo treatment or in vitro treatment. The IL-4 response of the 5907 group, while detectable, was below the result of the untreated control.

No detectable IL-4 was found in any supernatants, regardless of the dilution, in vivo treatment or in vitro treatment. IFN-γ was detectable only in Group B1 (20 μg of vaccine in vivo and 20 μg of PF2001 in vitro) at dilutions of 1:2 and 1:5 and Group B2 (20 μg of vaccine in vivo and 10 μg of PF2001 in vitro) at a dilution of 1:2. As observed in the assay for PF2001, there was no response for mouse 8682 on Wuhan. All of the remaining individual sera showed increased absorbance values from day 0 to day 42.

To demonstrate the utility of small conserved influenza regions or epitopes to induce immunity to native antigens on whole influenza virus, several HA and NA conserved regions were conjugated to a protein carrier such as tetanus toxoid or a portion thereof such as described in SEQ ID NO:53 (or alternatively, conjugated to bovine serum albumin [BSA]). One conjugate included the novel synthetic sequence GNLFIAP (SEQ ID NO:5; Peptide 5910). Mice were immunized with the influenza conserved peptide-protein conjugates and antibodies to whole H3 virus were measured before and at 42 days.

In addition, spleen cell IFN-γ was measured as an indicator of induced cell mediated immunity to influenza. Antibody responses to native HA and NA proteins were increased for all conserved epitope constructs at 5 μg and 20 μg. Surprisingly, the synthetic GNLFIAP (SEQ ID NO:5) construct when conjugated to BSA induced good antibody responses that bound to native influenza at both the 5-μg and 20-μg doses. In addition, IFN-γ was induced suggesting that at least some of these conserved regions can induce cell-mediated immunity (CMI) when cells are exposed to native antigens on influenza virus. Again, the unique synthetic peptide GNLFIAP (SEQ ID NO:5) (cf. different in sequence to that of the native influenza epitope) elicited a good IFN-γ response. These data indicated that small conserved epitopes and regions on antigens associated with shift and drift can induce immunity to influenza virus, and may be useful for developing highly cross-reactive vaccines. In addition, these data demonstrated that conjugation of these small conserved peptides to carriers such as proteins provides a method for producing a conserved region vaccine to provide broad microbial immunity.

TABLE 1

INDIVIDUAL ABSORBANCY VALUES OF SERA FOR TESTED PEPTIDES

| Mouse ID | Group | Peptide | Dose per Injection | Pre | Day 14 | Day 29 | Day 42 |
|---|---|---|---|---|---|---|---|
| 900 | 1 | 5907 | 20 μg | 0.077 | 0.072 | 0.080 | 0.161 |
| 901 | 1 | 5907 | 20 μg | 0.082 | 0.088 | 0.141 | 0.230 |
| 902 | 1 | 5907 | 20 μg | 0.108 | 0.090 | 0.093 | 0.156 |
| 903 | 1 | 5907 | 20 μg | 0.065 | 0.069 | 0.073 | 0.114 |
| 904 | 2 | 5907 | 5 μg | 0.080 | 0.096 | 0.160 | 0.165 |
| 905 | 2 | 5907 | 5 μg | 0.073 | 0.061 | 0.098 | 0.099 |
| 906 | 2 | 5907 | 5 μg | 0.084 | 0.079 | 0.099 | 0.139 |
| 907 | 2 | 5907 | 5 μg | 0.075 | 0.073 | 0.071 | No Sample |
| 908 | 3 | 5910 | 20 μg | 0.081 | 0.104 | 0.296 | 0.279 |
| 909 | 3 | 5910 | 20 μg | 0.083 | 0.081 | 0.077 | 0.164 |
| 910 | 3 | 5910 | 20 μg | 0.087 | 0.078 | 0.133 | 0.175 |
| 911 | 3 | 5910 | 20 μg | 0.083 | 0.144 | 0.302 | 0.333 |
| 912 | 4 | 5910 | 5 μg | 0.100 | 0.089 | 0.099 | 0.123 |
| 913 | 4 | 5910 | 5 μg | 0.110 | 0.090 | 0.226 | 0.306 |
| 914 | 4 | 5910 | 5 μg | 0.097 | 0.086 | 0.085 | 0.680 |
| 915 | 4 | 5910 | 5 μg | 0.308 | 0.186 | 0.149 | 0.162 |
| 916 | 5 | 5911 | 20 μg | 0.099 | 0.102 | 0.145 | 0.180 |
| 917 | 5 | 5911 | 20 μg | 0.109 | 0.136 | 0.240 | 0.304 |
| 918 | 5 | 5911 | 20 μg | 0.151 | 0.106 | 0.152 | 0.218 |
| 919 | 5 | 5911 | 20 μg | 0.121 | 0.123 | 0.170 | 0.158 |
| 920 | 6 | 5911 | 5 μg | 0.126 | 0.184 | 0.201 | 0.392 |
| 921 | 6 | 5911 | 5 μg | 0.187 | 0.503 | 0.303 | 0.497 |
| 922 | 6 | 1911 | 5 μg | 0.174 | 0.216 | 0.161 | 0.199 |
| 923 | 6 | 5911 | 5 μg | 0.137 | 0.154 | 0.188 | 0.300 |
| 924 | 7 | 5912 | 20 μg | 0.100 | 0.091 | 0.098 | 0.155 |
| 925 | 7 | 5912 | 20 μg | 0.098 | 0.082 | 0.146 | 0.189 |
| 926 | 7 | 5912 | 20 μg | 0.090 | 0.103 | 0.099 | 0.168 |
| 927 | 7 | 5912 | 20 μg | 0.123 | 0.088 | 0.096 | 0.111 |
| 928 | 8 | 5912 | 5 μg | 0.090 | 0.287 | 0.175 | 0.154 |
| 929 | 8 | 5912 | 5 μg | 0.094 | 0.109 | 0.137 | 0.167 |
| 930 | 8 | 5912 | 5 μg | 0.107 | 0.230 | 0.700 | 1.758 |
| 931 | 8 | 5912 | 5 μg | 0.156 | 0.147 | 0.138 | 0.154 |
| 932 | 9 | 5914 | 20 μg | 0.165 | 0.213 | 0.175 | 0.284 |
| 933 | 9 | 5914 | 20 μg | 0.133 | 0.150 | 0.214 | 0.480 |
| 934 | 9 | 5914 | 20 μg | 0.123 | 0.153 | 0.141 | 0.646 |
| 935 | 9 | 5914 | 20 μg | 0.165 | 0.180 | 0.156 | 0.234 |
| 936 | 10 | 5914 | 5 μg | 0.110 | 0.117 | 0.248 | 0.388 |
| 937 | 10 | 5914 | 5 μg | 0.133 | 0.123 | 0.136 | 0.264 |

TABLE 1-continued

INDIVIDUAL ABSORBANCY VALUES OF SERA FOR TESTED PEPTIDES

| Mouse ID | Group | Peptide | Dose per Injection | Pre | Day 14 | Day 29 | Day 42 |
|---|---|---|---|---|---|---|---|
| 938 | 10 | 5914 | 5 μg | 0.136 | 0.156 | 0.219 | 0.357 |
| 939 | 10 | 5914 | 5 μg | 0.126 | 0.118 | 0.121 | 0.127 |

Bold indicates 3-fold increase over pre-bleed optical density (OD) value.
Peptide sequences:
5907 GNLFIAPGNLFIAPQYLKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 2

SUMMARY OF ABSORBANCE VALUES OF SERA FOR TESTED PEPTIDES

| Group | Peptide # | Dose Per Injection | Pre | Day 14 | Day 29 | Day 42 |
|---|---|---|---|---|---|---|
| 1 | 5907 | 20 μg | 0.083 | 0.080 | 0.097 | 0.165 |
| 2 | 5907 | 5 μg | 0.078 | 0.077 | 0.107 | 0.134 |
| 3 | 5910 | 20 μg | 0.083 | 0.102 | 0.202 | 0.237 |
| 4 | 5910 | 5 μg | 0.154 | 0.113 | 0.140 | 0.318 |
| 5 | 5911 | 20 μg | 0.132 | 0.171 | 0.229 | 0.342 |
| 6 | 5911 | 5 μg | 0.156 | 0.264 | 0.213 | 0.347 |
| 7 | 5912 | 20 μg | 0.100 | 0.130 | 0.123 | 0.155 |
| 8 | 5912 | 5 μg | 0.130 | 0.162 | 0.325 | 0.693 |
| 9 | 5914 | 20 μg | 0.146 | 0.174 | 0.171 | 0.411 |
| 10 | 5914 | 5 μg | 0.126 | 0.128 | 0.181 | 0.284 |

Peptide sequences:
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 3

ABSORBANCE VALUES FOR INDIVIDUAL SERA FOR TESTED ON INFLUENZAVIRUS STRAIN WUHAN

| Grp. # | Peptide No. | Dose Per Injection | Pre | Day 42 | Mouse ID | Grp. # | Peptide | Dose Per Injection | Pre | Day 42 |
|---|---|---|---|---|---|---|---|---|---|---|
| 1 | 5907 | 20 μg | 0.091 | 0.224 | 920 | 6 | 5911 | 5 μg | 0.067 | 0.154 |
| 1 | 5907 | 20 μg | 0.097 | 0.394 | 921 | 6 | 5911 | 5 μg | 0.060 | 0.174 |
| 1 | 5907 | 20 μg | 0.102 | 0.174 | 922 | 6 | 5911 | 5 μg | 0.073 | 0.136 |
| 1 | 5907 | 20 μg | 0.071 | 0.119 | 923 | 6 | 5911 | 5 μg | 0.063 | 0.165 |
| 2 | 5907 | 5 μg | 0.084 | 0.212 | 924 | 7 | 5912 | 20 μg | 0.077 | 0.132 |
| 2 | 5907 | 5 μg | 0.062 | 0.082 | 925 | 7 | 5912 | 20 μg | 0.084 | 0.431 |
| 2 | 5907 | 5 μg | 0.068 | 0.250 | 926 | 7 | 5912 | 20 μg | 0.057 | 0.093 |
| 2 | 5907 | 5 μg | 0.063 | 0.039 | 927 | 7 | 5912 | 20 μg | 0.086 | 0.068 |
| 3 | 5910 | 20 μg | 0.069 | 0.546 | 928 | 8 | 5912 | 5 μg | 0.063 | 0.086 |
| 3 | 5910 | 20 μg | 0.070 | 0.096 | 929 | 8 | 5912 | 5 μg | 0.060 | 0.100 |
| 3 | 5910 | 20 μg | 0.071 | 0.271 | 930 | 8 | 5912 | 5 μg | 0.062 | 0.527 |
| 3 | 5910 | 20 μg | 0.092 | 0.385 | 931 | 8 | 5912 | 5 μg | 0.083 | 0.090 |
| 4 | 5910 | 5 μg | 0.076 | 0.449 | 932 | 9 | 5914 | 20 μg | 0.099 | 0.156 |
| 4 | 5910 | 5 μg | 0.092 | 0.341 | 933 | 9 | 5914 | 20 μg | 0.132 | 0.408 |

TABLE 3-continued

ABSORBANCE VALUES FOR INDIVIDUAL SERA FOR TESTED ON INFLUENZAVIRUS STRAIN WUHAN

| Grp. # | Peptide No. | Dose Per Injection | Pre | Day 42 | Mouse ID | Grp. # | Peptide | Dose Per Injection | Pre | Day 42 |
|---|---|---|---|---|---|---|---|---|---|---|
| 4 | 5910 | 5 µg | 0.068 | 0.288 | 934 | 9 | 5914 | 20 µg | 0.068 | 0.296 |
| 4 | 5910 | 5 µg | 0.109 | 0.088 | 935 | 9 | 5914 | 20 µg | 0.080 | 0.182 |
| 5 | 5911 | 20 µg | 0.065 | 0.747 | 936 | 10 | 5914 | 5 µg | 0.062 | 0.172 |
| 5 | 5911 | 20 µg | 0.069 | 0.194 | 937 | 10 | 5914 | 5 µg | 0.059 | 0.329 |
| 5 | 5911 | 20 µg | 0.084 | 0.154 | 938 | 10 | 5914 | 5 µg | 0.090 | 0.239 |
| 5 | 5911 | 20 µg | 0.070 | 0.134 | 939 | 10 | 5914 | 5 µg | 0.083 | 0.096 |

Bold indicates an increase of 3-fold or more over pre-bleed absorbance value.
Peptide sequences:
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 4

INDUCTION OF IFN-γ AND IL-4 IN SPLENOCYTE CULTURES FOLLOWING 72-HOUR CULTURE WITH SELECT IMMUNOGENIC PEPTIDES

| In Vivo Peptide Immunogen | In Vitro Treatment of Spleen Cells (µg/ml) | IFN-γ Results In Vivo Rx 20 µg | IFN-γ Results In Vivo Rx 5 µg | IL-4 Results In Vivo Rx 20 µg | IL-4 Results In Vivo Rx 5 µg |
|---|---|---|---|---|---|
| 5907 | 20 | 1.908 | 1.354 | 0.393 | BDL |
| 5907 | 10 | 1.516 | 1.349 | 0.139 | BDL |
| 5907 | 5 | 0.995 | 0.734 | 0.257 | BDL |
| 5907 | 2.5 | 1.052 | 0.698 | 0.170 | BDL |
| 5907 | Wuhan | 1.077 | 0.510 | 0.110 | BDL |
| 5910 | 20 | 4.782 | 3.315 | BDL | BDL |
| 5910 | 10 | 3.856 | 2.440 | BDL | BDL |
| 5910 | 5 | 2.935 | 1.018 | BDL | BDL |
| 5910 | 2.5 | 2.771 | 1.218 | BDL | BDL |
| 5910 | Wuhan | 1.347 | 1.133 | BDL | BDL |
| 5911 | 20 | 0.936 | 2.449 | BDL | BDL |
| 5911 | 10 | 1.440 | 1.818 | BDL | BDL |
| 5911 | 5 | 1.428 | 1.494 | BDL | BDL |
| 5911 | 2.5 | 1.043 | 1.380 | BDL | BDL |
| 5911 | Wuhan | 2.208 | 0.959 | BDL | BDL |
| 5912 | 20 | 1.744 | 0.282 | BDL | BDL |
| 5912 | 10 | 1.996 | 0.159 | BDL | BDL |
| 5912 | 5 | 1.495 | 0.235 | BDL | BDL |
| 5912 | 2.5 | 1.779 | 0.237 | BDL | BDL |
| 5912 | Wuhan | 1.067 | 0.126 | BDL | BDL |

TABLE 4-continued

INDUCTION OF IFN-γ AND IL-4 IN SPLENOCYTE CULTURES FOLLOWING 72-HOUR CULTURE WITH SELECT IMMUNOGENIC PEPTIDES

| In Vivo Peptide Immunogen | In Vitro Treatment of Spleen Cells (µg/ml) | Fold Increase Over Control | | | |
|---|---|---|---|---|---|
| | | IFN-γ Results | | IL-4 Results | |
| | | In Vivo Rx 20 µg | In Vivo Rx 5 µg | In Vivo Rx 20 µg | In Vivo Rx 5 µg |
| 5914 | 20 | 1.477 | 0.425 | BDL | BDL |
| 5914 | 10 | 1.524 | 2.252 | BDL | BDL |
| 5914 | 5 | 0.947 | 0.954 | BDL | BDL |
| 5914 | 2.5 | 1.028 | 1.173 | BDL | BDL |
| 5914 | Wuhan | 0.086 | 0.086 | BDL | BDL |

BDL = Below detectable limit.
Peptide sequences (all formulated in BSA):
5907 GNLFIAPGNLFIAPQYIKANSKFIGITEGNLFIAP (SEQ ID NO: 15);
5910 GNLFIAP (SEQ ID NO: 5);
5911 HYEECSCY (SEQ ID NO: 7);
5912 DWSGYSGSFVQHPELTGL (SEQ ID NO: 11);
and 5914 KSCINFCFYVELIRGR (SEQ ID NO: 20).

TABLE 5

INDUCTION OF IFN-γ IN SPLENOCYTES FOLLOWING 72 HOURS OF TREATMENT WITH PEPTIDE

| Group | In Vivo Peptide Immunogen | In Vivo Dose | Peptide Rx of Spleen Cells (µg/ml) | Calculated ng/ml IFN-γ | Fold over Increase Control |
|---|---|---|---|---|---|
| 1 | 5907 | 20 µg | 20 | 2566.60 | 1.91 |
| 1 | 5907 | 20 µg | 10 | 2038.96 | 1.52 |
| 1 | 5907 | 20 µg | 5 | 1338.40 | 1.00 |
| 1 | 5907 | 20 µg | 2.5 | 1415.51 | 1.05 |
| 1 | 5907 | 20 µg | None | 1345.11 | 1.00 |
| 1 | 5907 | 20 µg | Virus | 1448.19 | 1.08 |
| 2 | 5907 | 5 µg | 20 | 528.85 | 1.35 |
| 2 | 5907 | 5 µg | 10 | 526.97 | 1.35 |
| 2 | 5907 | 5 µg | 5 | 286.74 | 0.73 |
| 2 | 5907 | 5 µg | 2.5 | 272.64 | 0.70 |
| 2 | 5907 | 5 µg | None | 390.68 | 1.00 |
| 2 | 5907 | 5 µg | Virus | 199.14 | 0.51 |
| 3 | 5910 | 20 µg | 20 | 1336.30 | 4.78 |
| 3 | 5910 | 20 µg | 10 | 1077.69 | 3.86 |
| 3 | 5910 | 20 µg | 5 | 820.23 | 2.94 |
| 3 | 5910 | 20 µg | 2.5 | 774.23 | 2.77 |
| 3 | 5910 | 20 µg | None | 279.45 | 1.00 |
| 3 | 5910 | 20 µg | Virus | 376.39 | 1.35 |
| 4 | 5910 | 5 µg | 20 | 434.97 | 3.32 |
| 4 | 5910 | 5 µg | 10 | 320.18 | 2.44 |
| 4 | 5910 | 5 µg | 5 | 133.62 | 1.02 |
| 4 | 5910 | 5 µg | 2.5 | 159.78 | 1.22 |
| 4 | 5910 | 5 µg | None | 131.20 | 1.00 |
| 4 | 5910 | 5 µg | Virus | 148.62 | 1.13 |
| 7 | 5912 | 20 µg | 20 | 679.78 | 1.74 |
| 7 | 5912 | 20 µg | 10 | 777.72 | 2.00 |
| 7 | 5912 | 20 µg | 5 | 582.48 | 1.49 |
| 7 | 5912 | 20 µg | 2.5 | 693.25 | 1.78 |
| 7 | 5912 | 20 µg | None | 389.71 | 1.00 |
| 7 | 5912 | 20 µg | Virus | 415.72 | 1.07 |
| 8 | 5912 | 5 µg | 20 | 44.63 | 0.28 |
| 8 | 5912 | 5 µg | 10 | 25.14 | 0.16 |
| 8 | 5912 | 5 µg | 5 | 37.15 | 0.23 |
| 8 | 5912 | 5 µg | 2.5 | 37.46 | 0.24 |
| 8 | 5912 | 5 µg | None | 158.39 | 1.00 |
| 8 | 5912 | 5 µg | Virus | 19.95 | 0.13 |
| 9 | 5914 | 20 µg | 20 | 1038.05 | 1.48 |
| 9 | 5914 | 20 µg | 10 | 1071.16 | 1.52 |
| 9 | 5914 | 20 µg | 5 | 665.78 | 0.95 |
| 9 | 5914 | 20 µg | 2.5 | 722.92 | 1.03 |

TABLE 5-continued

INDUCTION OF IFN-γ IN SPLENOCYTES FOLLOWING 72 HOURS OF TREATMENT WITH PEPTIDE

| Group | In Vivo Peptide Immunogen | In Vivo Dose | Peptide Rx of Spleen Cells (μg/ml) | Calculated ng/ml IFN-γ | Fold over Increase Control |
|---|---|---|---|---|---|
| 9 | 5914 | 20 μg | None | 702.95 | 1.00 |
| 9 | 5914 | 20 μg | Virus | 607.53 | 0.86 |
| 10 | 5914 | 5 μg | 20 | 201.52 | 0.43 |
| 10 | 5914 | 5 μg | 10 | 1067.12 | 2.25 |
| 10 | 5914 | 5 μg | 5 | 452.13 | 0.95 |
| 10 | 5914 | 5 μg | 2.5 | 555.82 | 1.17 |
| 10 | 5914 | 5 μg | None | 473.87 | 1.00 |
| 10 | 5914 | 5 μg | Virus | 409.40 | 0.86 |

Virus = 200 μl of Wuhan 0307 359/95
Spleen cells were incubated with peptide or virus at the indicated concentration for 72 hours.
Spleen cells from mouse 39 were cultured separately. The spleen from this mouse was unusually large.
Peptide sequences (all in BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 6

INDUCTION OF IFN-γ IN SPLENOCYTES FOLLOWING 72 HOURS OF TREATMENT WITH PEPTIDE

| Group | In Vivo Peptide Immunogen | In Vivo Dose | Peptide Rx of Spleen Cells (μg/ml) | Calculated IFN-γ (ng/ml) | Fold over Increase Control |
|---|---|---|---|---|---|
| 5 | 5911 | 20 μg | 20 | 306.375 | 0.94 |
| 5 | 5911 | 20 μg | 10 | 471.373 | 1.44 |
| 5 | 5911 | 20 μg | 5 | 467.554 | 1.43 |
| 5 | 5911 | 20 μg | 2.5 | 341.46 | 1.04 |
| 5 | 5911 | 20 μg | None | ND | |
| 5 | 5911 | 20 μg | Virus | 722.79 | 2.21 |
| 6 | 5911 | 5 μg | 20 | 801.569 | 2.45 |
| 6 | 5911 | 5 μg | 10 | 594.95 | 1.82 |
| 6 | 5911 | 5 μg | 5 | 488.89 | 1.49 |
| 6 | 5911 | 5 μg | 2.5 | 451.753 | 1.38 |
| 6 | 5911 | 5 μg | None | 327.311 | 1.00 |
| 6 | 5911 | 5 μg | Virus | 314.035 | 0.96 |
| 39 | 5914 | 5 μg | 20 | BDL | |
| 39 | 5914 | 5 μg | 10 | BDL | |
| 39 | 5914 | 5 μg | 5 | BDL | |
| 39 | 5914 | 5 μg | 2.5 | BDL | |
| 39 | 5914 | 5 μg | None | BDL | |
| 39 | 5914 | 5 μg | Virus | BDL | |

Virus = 200 μl of Wuhan 0307 359/95
Spleen cells were incubated with peptide or virus at the indicated concentration for 72 hours.
Spleen cells from mouse 39 were cultured separately. The spleen from this mouse was unusually large.
BDL = Below detectable limit.
ND = Not determined.
Peptide sequences (all in BSA):
5911 HYEECSCY (SEQ ID NO: 7)
5914 KSCINFCFYVELIRGR (SEQ ID NO: 20)

TABLE 7

INDUCTION OF IFN-γ IN SPLENOCYTES FOLLOWING 72 HOURS OF TREATMENT WITH PEPTIDE

| In Vivo Peptide Immunogen | Peptide Rx of Spleen Cells (μg/ml) | Fold over Control 20 μg In Vivo | Fold over Control 5 μg In Vivo |
|---|---|---|---|
| 5907 | 20 | 1.908 | 1.354 |
| 5907 | 10 | 1.516 | 1.349 |
| 5907 | 5 | 0.995 | 0.734 |
| 5907 | 2.5 | 1.052 | 0.698 |
| 5910 | 20 | 4.782 | 3.315 |
| 5910 | 10 | 3.856 | 2.440 |
| 5910 | 5 | 2.935 | 1.018 |
| 5910 | 2.5 | 2.771 | 1.218 |
| 5911 | 20 | 0.936 | 2.449 |
| 5911 | 10 | 1.440 | 1.818 |
| 5911 | 5 | 1.428 | 1.494 |
| 5911 | 2.5 | 1.043 | 1.380 |
| 5912 | 20 | 1.744 | 0.282 |
| 5912 | 10 | 1.996 | 0.159 |
| 5912 | 5 | 1.495 | 0.235 |
| 5912 | 2.5 | 1.779 | 0.237 |
| 5914 | 20 | 1.477 | 0.425 |
| 5914 | 10 | 1.524 | 2.252 |

TABLE 7-continued

INDUCTION OF IFN-γ IN SPLENOCYTES
FOLLOWING 72 HOURS OF TREATMENT WITH PEPTIDE

| In Vivo Peptide Immunogen | Peptide Rx of Spleen Cells (μg/ml) | Fold over Control 20 μg In Vivo | 5 μg In Vivo |
|---|---|---|---|
| 5914 | 5 | 0.947 | 0.954 |
| 5914 | 2.5 | 1.028 | 1.173 |

Virus = 200 μl of Wuhan 0307 359/95.
Spleen cells were incubated with peptide or virus at the indicated concentration for 72 hours.
Spleen cells from mouse 39 were cultured separately. The spleen from this mouse was unusually large.
Peptide sequences (all in BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 8

INDUCTION OF IL-4 IN SPLENOCYTES
FOLLOWING 72 HOURS OF TREATMENT WITH PEPTIDE

| Group | In Vivo Peptide Immunogen | In Vivo Dose | Peptide Rx of Spleen Cells (μg/ml) | Calculated ng/ml IL-4 | Fold over Increase Control |
|---|---|---|---|---|---|
| 1 | 5907 | 20 μg | 20 | 53.21 | 0.39 |
| 1 | 5907 | 20 μg | 10 | 18.82 | 0.14 |
| 1 | 5907 | 20 μg | 5 | 34.85 | 0.26 |
| 1 | 5907 | 20 μg | 2.5 | 23.01 | 0.17 |
| 1 | 5907 | 20 μg | None | 135.47 | 1.00 |
| 1 | 5907 | 20 μg | Virus | 14.26 | 0.11 |
| 2 | 5907 | 5 μg | 20 | BDL | NA |
| 2 | 5907 | 5 μg | 10 | 18.99 | NA |
| 2 | 5907 | 5 μg | 5 | BDL | NA |
| 2 | 5907 | 5 μg | 2.5 | BDL | NA |
| 2 | 5907 | 5 μg | None | BDL | NA |
| 2 | 5907 | 5 μg | Virus | BDL | NA |
| 3 | 5910 | 20 μg | 20 | 1.49 | NA |
| 3 | 5910 | 20 μg | 10 | BDL | NA |
| 3 | 5910 | 20 μg | 5 | BDL | NA |
| 3 | 5910 | 20 μg | 2.5 | BDL | NA |
| 3 | 5910 | 20 μg | None | BDL | NA |
| 3 | 5910 | 20 μg | Virus | BDL | NA |
| 4 | 5910 | 5 μg | 20 | BDL | NA |
| 4 | 5910 | 5 μg | 10 | BDL | NA |
| 4 | 5910 | 5 μg | 5 | BDL | NA |
| 4 | 5910 | 5 μg | 2.5 | BDL | NA |
| 4 | 5910 | 5 μg | None | BDL | NA |
| 4 | 5910 | 5 μg | Virus | BDL | NA |
| 7 | 5912 | 20 μg | 20 | BDL | NA |
| 7 | 5912 | 20 μg | 10 | BDL | NA |
| 7 | 5912 | 20 μg | 5 | BDL | NA |
| 7 | 5912 | 20 μg | 2.5 | BDL | NA |
| 7 | 5912 | 20 μg | None | BDL | NA |
| 7 | 5912 | 20 μg | Virus | BDL | NA |
| 8 | 5912 | 5 μg | 20 | BDL | NA |
| 8 | 5912 | 5 μg | 10 | BDL | NA |
| 8 | 5912 | 5 μg | 5 | BDL | NA |
| 8 | 5912 | 5 μg | 2.5 | BDL | NA |
| 8 | 5912 | 5 μg | None | BDL | NA |
| 8 | 5912 | 5 μg | Virus | BDL | NA |
| 9 | 5914 | 20 μg | 20 | BDL | NA |
| 9 | 5914 | 20 μg | 10 | BDL | NA |
| 9 | 5914 | 20 μg | 5 | BDL | NA |
| 9 | 5914 | 20 μg | 2.5 | BDL | NA |
| 9 | 5914 | 20 μg | None | BDL | NA |
| 9 | 5914 | 20 μg | Virus | BDL | NA |
| 10 | 5914 | 5 μg | 20 | BDL | NA |
| 10 | 5914 | 5 μg | 10 | BDL | NA |
| 10 | 5914 | 5 μg | 5 | BDL | NA |
| 10 | 5914 | 5 μg | 2.5 | BDL | NA |
| 10 | 5914 | 5 μg | None | BDL | NA |
| 10 | 5914 | 5 μg | Virus | BDL | NA |

Virus = 200 μl of Wuhan 0307 359/95.
Spleen cells were incubated with peptide or virus at the indicated concentration for 72 hours.
Spleen cells from mouse 39 were cultured separately. The spleen from this mouse was unusually large.
BDL = Below detectable limit.
NA = Not applicable.
Peptide sequences (all conjugated to BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 9

INDUCTION OF IL-4 IN SPLENOCYTES FOLLOWING 72 HOURS OF TREATMENT WITH PEPTIDE

| Group | In Vivo Peptide Immunogen | In Vivo Dose | Peptide Rx of Spleen Cells (µg/ml) | Calculated ng/ml IL-4 | Fold over Increase Control |
|---|---|---|---|---|---|
| 5 | 5911 | 20 µg | 20 | BDL | NA |
| 5 | 5911 | 20 µg | 0 | BDL | NA |
| 5 | 5911 | 20 µg | 5 | BDL | NA |
| 5 | 5911 | 20 µg | 2.5 | BDL | NA |
| 5 | 5911 | 20 µg | None | BDL | NA |
| 5 | 5911 | 20 µg | Virus | 1.49 | NA |
| 6 | 5911 | 5 µg | 20 | BDL | NA |
| 6 | 5911 | 5 µg | 10 | BDL | NA |
| 6 | 5911 | 5 µg | 5 | BDL | NA |
| 6 | 5911 | 5 µg | 2.5 | BDL | NA |
| 6 | 5911 | 5 µg | None | BDL | NA |
| 6 | 5911 | 5 µg | Virus | BDL | NA |
| 39 | 5914 | 5 µg | 20 | BDL | NA |
| 39 | 5914 | 5 µg | 10 | BDL | NA |
| 39 | 5914 | 5 µg | 5 | BDL | NA |
| 39 | 5914 | 5 µg | 2.5 | BDL | NA |
| 39 | 5914 | 5 µg | None | BDL | NA |
| 39 | 5914 | 5 µg | Virus | BDL | NA |

Virus = 200 µl of Wuhan 0307 359/95
Spleen cells were incubated with peptide or virus at the indicated concentration for 72 hours.
Spleen cells from mouse 39 were cultured separately. The spleen from this mouse was unusually large.
Peptide sequences (all in BSA):
5911 HYEECSCY (SEQ ID NO: 7)
5914 KSCINFCFYVELIRGR (SEQ ID NO: 20)

TABLE 10

INDUCTION OF IL-4 IN SPLENOCYTES FOLLOWING 72 HOURS OF TREATMENT WITH PEPTIDE

| In Vivo Peptide Immunogen | Peptide Rx of Spleen Cells (µg/ml) | Fold over Control 20 µg In Vivo | Fold over Control 5 µg In Vivo |
|---|---|---|---|
| 5907 | 20 | 0.393 | NA |
| 5907 | 10 | 0.139 | NA |
| 5907 | 5 | 0.257 | NA |
| 5907 | 2.5 | 0.170 | NA |
| 5910 | 20 | NA | NA |
| 5910 | 10 | NA | NA |
| 5910 | 5 | NA | NA |
| 5910 | 2.5 | NA | NA |
| 5911 | 20 | NA | NA |
| 5911 | 10 | NA | NA |
| 5911 | 5 | NA | NA |
| 5911 | 2.5 | NA | NA |
| 5912 | 20 | NA | NA |
| 5912 | 10 | NA | NA |
| 5912 | 5 | NA | NA |
| 5912 | 2.5 | NA | NA |
| 5914 | 20 | NA | NA |
| 5914 | 10 | NA | NA |
| 5914 | 5 | NA | NA |
| 5914 | 2.5 | NA | NA |

Virus = 200 µl of Wuhan 0307 359/95
Spleen cells were incubated with peptide or virus at the indicated concentration for 72 hours.
Spleen cells from mouse 39 were cultured separately. The spleen from this mouse was unusually large.
Peptide sequences (all in BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 11

COMPARISON OF ELISA ABSORBANCE VALUES FOR INDIVIDUAL SERA AT 1:100 ON PF2001 (PEPTIDE 5906) AND ON PN14 POLYSACCHARIDE

| Mouse ID | Dose | Day 14 5906 | Day 14 Pn14 | Day 28 5906 | Day 28 Pn14 | Day 42 5906 | Day 42 Pn14 |
|---|---|---|---|---|---|---|---|
| 6876 | 5 ug | 0.091 | 0.089 | 0.114 | 0.095 | 0.368 | 0.398 |
| 6877 | 5 ug | 0.214 | 0.226 | 0.597 | 0.448 | 0.546 | 0.523 |
| 6878 | 5 ug | 0.231 | 0.248 | 0.259 | 0.260 | 0.381 | 0.351 |
| 6879 | 5 ug | 0.174 | 1.023 | 0.228 | 0.693 | 0.287 | 0.744 |
| 6880 | 20 ug | 0.140 | 0.116 | 0.197 | 0.252 | 0.192 | 0.375 |

TABLE 11-continued

COMPARISON OF ELISA ABSORBANCE VALUES FOR INDIVIDUAL SERA AT 1:100 ON PF2001 (PEPTIDE 5906) AND ON PN14 POLYSACCHARIDE

| Mouse ID | Dose | Day 14 5906 | Day 14 Pn14 | Day 28 5906 | Day 28 Pn14 | Day 42 5906 | Day 42 Pn14 |
|---|---|---|---|---|---|---|---|
| 6881 | 20 ug | 0.635 | 0.615 | 0.317 | 2.829 | 0.677 | 3.480 |
| 6882 | 20 ug | 0.061 | 0.106 | 0.077 | 0.941 | 0.088 | 0.638 |
| 6883 | 20 ug | 0.088 | 0.111 | 0.684 | 0.646 | 1.229 | 0.840 |

Peptide sequence of PF2001 (Peptide 5906):
SLLTEVETPIRNEWGLLTEVETPIRQYIKANSKFIGITE (SEQ ID NO: 44)

TABLE 12

ABSORBANCE VALUES OF INDIVIDUAL SERA BY ELISA ON FLU WUHAN SERA AT 1:100

| Mouse ID | Vaccine | Dose (ug) | Absorbance Prebleed | Absorbance Prebleed | Average | Absorbance D-42 | Absorbance D-42 | Average |
|---|---|---|---|---|---|---|---|---|
| 876 | 5906-Pn14 | 5 ug | 0.082 | 0.084 | 0.083 | 0.312 | 0.309 | 0.311 |
| 877 | 5906-Pn14 | 5 ug | 0.086 | 0.084 | 0.085 | 0.516 | 0.463 | 0.490 |
| 878 | 5906-Pn14 | 5 ug | 0.088 | 0.087 | 0.088 | 0.341 | 0.312 | 0.327 |
| 879 | 5906-Pn14 | 5 ug | 0.096 | 0.098 | 0.097 | 0.262 | 0.345 | 0.304 |
| 880 | 5906-Pn14 | 20 ug | 0.094 | 0.096 | 0.095 | 0.162 | 0.152 | 0.157 |
| 881 | 5906-Pn14 | 20 ug | 0.082 | 0.089 | 0.086 | 0.629 | 0.569 | 0.599 |
| 882 | 5906-Pn14 | 20 ug | 0.072 | 0.071 | 0.072 | 0.081 | 0.081 | 0.081 |
| 883 | 5906-Pn14 | 20 ug | 0.087 | 0.079 | 0.083 | 1.129 | 1.088 | 1.109 |

Peptide sequence (PF2001 (Peptide 5906) conjugated to Pn14):
SLLTEVETPIRNEWGLLTEVETPIRQYIKANSKFIGITE (SEQ ID NO: 44)

TABLE 13

IFN-γ AND IL-4 LEVELS IN SUPERNATANTS FROM SPLEEN CULTURES

IFN and IL-4 Results Summary

| Sup ID | In Vivo Dosage | In Vitro Inducer | In Vitro Dosage | Dilution for IFN Assay | OD | Calculated IFN-gamma (pg/ml) | Dilution for IL4 Assay | OD | Calculated IL4 (pg/ml) |
|---|---|---|---|---|---|---|---|---|---|
| A1 | 5 ug | 5906 | 20 ug | 2 | 0.049 | BDL | 2 | 0.111 | BDL |
| A1 | 5 ug | 5906 | 20 ug | 5 | 0.044 | BDL | 4 | 0.120 | BDL |
| A2 | 5 ug | 5906 | 10 ug | 2 | 0.046 | BDL | 2 | 0.112 | BDL |
| A2 | 5 ug | 5906 | 10 ug | 5 | 0.045 | BDL | 4 | 0.121 | BDL |
| A3 | 5 ug | 5906 | 5 ug | 2 | 0.046 | BDL | 2 | 0.114 | BDL |
| A3 | 5 ug | 5906 | 5 ug | ND | ND | ND | 4 | 0.126 | BDL |
| A4 | 5 ug | Pn14 | 20 | 2 | 0.043 | BDL | 2 | 0.116 | BDL |
| A4 | 5 ug | Pn14 | 20 | ND | ND | ND | 4 | 0.123 | BDL |
| A5 | 5 ug | Wuhan | 0.1 ml | 2 | 0.044 | BDL | 2 | 0.117 | BDL |
| A5 | 5 ug | Wuhan | 0.1 ml | 5 | 0.046 | BDL | 4 | 0.110 | BDL |
| A6 | 5 ug | None | NA | 2 | 0.056 | BDL | 2 | 0.117 | BDL |
| A6 | 5 ug | None | NA | ND | ND | ND | 4 | 0.113 | BDL |

TABLE 13-continued

IFN-γ AND IL-4 LEVELS IN SUPERNATANTS FROM SPLEEN CULTURES

| | | | | | | | | | |
|---|---|---|---|---|---|---|---|---|---|
| B1 | 20 ug | 5906 | 20 ug | 2 | 0.098 | 98.651 | 2 | 0.128 | BDL |
| B1 | 20 ug | 5906 | 20 ug | 5 | 0.074 | 128.681 | 4 | 0.120 | BDL |
| B2 | 20 ug | 5906 | 10 ug | 2 | 0.081 | 64.887 | 2 | 0.135 | BDL |
| B2 | 20 ug | 5906 | 10 ug | 5 | 0.060 | BDL | 4 | 0.112 | BDL |
| B3 | 20 ug | 5906 | 5 ug | 2 | 0.061 | BDL | 2 | 0.108 | BDL |
| B3 | 20 ug | 5906 | 5 ug | ND | ND | ND | 4 | 0.119 | BDL |
| B4 | 20 ug | Pn14 | 20 | 2 | 0.043 | BDL | 2 | 0.116 | BDL |
| B4 | 20 ug | Pn14 | 20 | ND | ND | ND | 4 | 0.125 | BDL |
| B5 | 20 ug | Wuhan | 0.1 ml | 2 | 0.050 | BDL | 2 | 0.116 | BDL |
| B5 | 20 ug | Wuhan | 0.1 ml | 5 | 0.047 | BDL | 4 | 0.139 | BDL |
| B6 | 20 ug | None | NA | 2 | 0.062 | BDL | 2 | 0.113 | BDL |
| B6 | 20 ug | None | NA | ND | ND | ND | 4 | 0.138 | BDL |

| IFN Stnd | | IL4 Stnd | |
|---|---|---|---|
| Conc | Abs | Conc | Abs |
| 1000 | 0.990 | 1800 | 2.023 |
| 500 | 0.568 | 900 | 1.384 |
| 250 | 0.318 | 450 | 0.822 |
| 125 | 0.176 | 150 | 0.376 |
| 62.5 | 0.110 | 50 | 0.204 |
| 31.25 | 0.079 | 25 | 0.173 |
| 15.625 | 0.067 | 12.5 | 0.160 |
| None | 0.052 | None | 0.143 |

Peptide sequence of PF2001 (Peptide 5906):
SLLTEVETPIRNEWGLLTEVETPIRQYIKANSKFIGITE (SEQ ID NO: 44)

TABLE 14

ANTI-WUHAN INDIVIDUAL RESULTS SUMMARY SERA AT 1:100 DILUTION

| Mouse ID | Group | Peptide | Dose per Inject | Absorbance Pre-Bleed | Absorbance Day 42 |
|---|---|---|---|---|---|
| 900 | 1 | 5907 | 20 µg | 0.091 | 0.224 |
| 901 | 1 | 5907 | 20 µg | 0.087 | 0.394 |
| 902 | 1 | 5907 | 20 µg | 0.102 | 0.174 |
| 903 | 1 | 5907 | 20 µg | 0.071 | 0.119 |
| 904 | 2 | 5907 | 5 µg | 0.084 | 0.212 |
| 905 | 2 | 5907 | 5 µg | 0.062 | 0.082 |
| 906 | 2 | 5907 | 5 µg | 0.068 | 0.250 |
| 907 | 2 | 5907 | 5 µg | 0.063 | 0.039 |
| 908 | 3 | 5910 | 20 µg | 0.069 | 0.546 |
| 909 | 3 | 5910 | 20 µg | 0.070 | 0.096 |
| 910 | 3 | 5910 | 20 µg | 0.071 | 0.271 |
| 911 | 3 | 5910 | 20 µg | 0.092 | 0.385 |
| 912 | 4 | 5910 | 5 µg | 0.076 | 0.449 |
| 913 | 4 | 5910 | 5 µg | 0.092 | 0.341 |
| 914 | 4 | 5910 | 5 µg | 0.068 | 0.288 |
| 915 | 4 | 5910 | 5 µg | 0.109 | 0.088 |
| 916 | 5 | 5911 | 20 µg | 0.065 | 0.747 |
| 917 | 5 | 5911 | 20 µg | 0.069 | 0.194 |
| 918 | 5 | 5911 | 20 µg | 0.084 | 0.154 |

TABLE 14-continued

ANTI-WUHAN INDIVIDUAL RESULTS SUMMARY SERA AT 1:100 DILUTION

| Mouse ID | Group | Peptide | Dose per Inject | Absorbance Pre-Bleed | Absorbance Day 42 |
|---|---|---|---|---|---|
| 919 | 5 | 5911 | 20 µg | 0.070 | 0.134 |
| 920 | 6 | 5911 | 5 µg | 0.067 | 0.154 |
| 921 | 6 | 5911 | 5 µg | 0.060 | 0.174 |
| 922 | 6 | 5911 | 5 µg | 0.073 | 0.136 |
| 923 | 6 | 5911 | 5 µg | 0.063 | 0.165 |
| 924 | 7 | 5912 | 20 µg | 0.077 | 0.132 |
| 925 | 7 | 5912 | 20 µg | 0.084 | 0.431 |
| 926 | 7 | 5912 | 20 µg | 0.057 | 0.093 |
| 927 | 7 | 5912 | 20 µg | 0.086 | 0.068 |
| 928 | 8 | 5912 | 5 µg | 0.063 | 0.086 |
| 929 | 8 | 5912 | 5 µg | 0.060 | 0.100 |
| 930 | 8 | 5912 | 5 µg | 0.062 | 0.527 |
| 931 | 8 | 5912 | 5 µg | 0.083 | 0.090 |
| 932 | 9 | 5914 | 20 µg | 0.099 | 0.156 |
| 933 | 9 | 5914 | 20 µg | 0.132 | 0.408 |
| 934 | 9 | 5914 | 20 µg | 0.068 | 0.296 |
| 935 | 9 | 5914 | 20 µg | 0.080 | 0.182 |
| 936 | 10 | 5914 | 5 µg | 0.062 | 0.176 |
| 937 | 10 | 5914 | 5 µg | 0.059 | 0.329 |
| 938 | 10 | 5914 | 5 µg | 0.090 | 0.239 |
| 939 | 10 | 5914 | 5 µg | 0.083 | 0.096 |

Peptide sequences (all conjugated to BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

TABLE 15

ANTI-WUHAN SUMMARY OF AVERAGED RESULTS SERA AT 1:100 DILUTION

| Group | Peptide | Dose Per Injection | Absorbance Pre-Bleed | Absorbance Day 42 | Std. Dev. Pre-Bleed | Std. Dev. Day 42 |
|---|---|---|---|---|---|---|
| 1 | 5907 | 20 µg | 0.088 | 0.227 | 0.013 | 0.119 |
| 2 | 5907 | 5 µg | 0.069 | 0.146 | 0.010 | 0.101 |
| 3 | 5910 | 20 µg | 0.075 | 0.324 | 0.011 | 0.190 |
| 4 | 5910 | 5 µg | 0.086 | 0.291 | 0.018 | 0.151 |
| 5 | 5911 | 20 µg | 0.072 | 0.307 | 0.008 | 0.294 |
| 6 | 5911 | 5 µg | 0.065 | 0.157 | 0.006 | 0.016 |
| 7 | 5912 | 20 µg | 0.076 | 0.181 | 0.013 | 0.169 |
| 8 | 5912 | 5 µg | 0.067 | 0.201 | 0.011 | 0.217 |
| 9 | 5914 | 20 µg | 0.094 | 0.260 | 0.028 | 0.115 |
| 10 | 5914 | 5 µg | 0.073 | 0.210 | 0.015 | 0.099 |

Peptide sequences (all conjugated to BSA):
5907 GNLFIAPGNLFIAPQYIKANSKFIGITEGNLFIAP (SEQ ID NO: 15)
5910 GNLFIAP (SEQ ID NO: 5)
5911 HYEECSCY (SEQ ID NO: 7)
5912 DWSGYSGSFVQHPELTGL (SEQ ID NO: 11)
5914 KSCINFCFYVELIRGR (SEQ ID NO: 20)

Example 6

HA and N1 Selected Peptide Sequences

There are three homologous regions within H1N1 and H5N1 Neuraminidase (N1) proteins. The N1 sequences were derived from multiple sequence alignments of 83 full-length NA sequences. The represented H1N1 and H5N1 sequences are quite diversified representing human, other mammalian, i.e., feline and avian origin, and include contemporary and vintage strains dating back as far 1983. The avian strains were obtained from a variety of species, i.e., chicken, goose, duck, swan, buzzard, vulture, gull, falcon, crow, crested myna, and cormorant. Also included in the multiple sequence alignment was A/Solomon Islands/3/2006 (H1N1), the recently selected 2007-08 human influenza A virus vaccine component, and A/New Calcdonia/20/99 the current human H1N1 influenza A virus vaccine component.

Multiple sequence alignments and primary protein translations were performed using MegAlign® (v. 5.06, DNAStar, Inc., Madison, Wis., USA). Three-dimensional structures were created using the New Calcdonia/20/1999 NA peptide antigen sequence with Deep viewer/Swiss PDB Viewer V 3.7 and based on the deduced X-ray structure of A/Viet Nam/1203/2004 (H5N1) described by Lou (2006).

Figure 8:
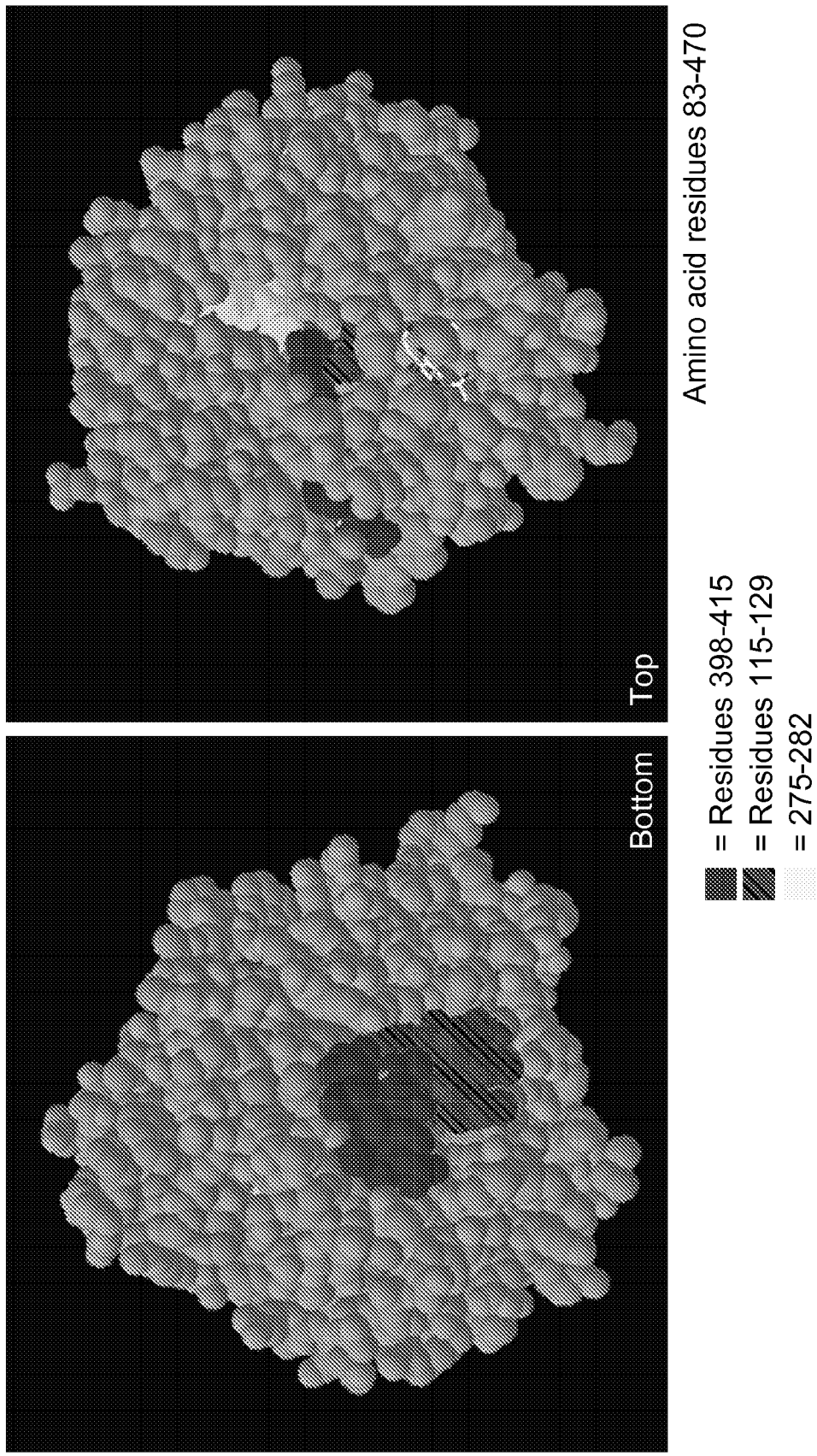
FIG. 8 shows a view of the presentation of a preferred NA epitope on the NA polypeptide.

FIG. 7 depicts three regions within the sequence of the globular head of the NA protein that are conserved across all 83 strains. It is interesting to note that primary amino acid sequence and resultant 3-protein are often two separate entities due to amino acid properties, e.g., net charge, R group, polarity. For example, NA residues at positions 118, 119, 178, 371, 292, 152, 222, 276, 246, and 151 are all scattered throughout the primary NA sequence. However, upon folding in the final conformational 3-D state they are all huddled in somewhat close proximity and function collectively to bind to sialic acid, as shown in FIG. 8.

Individually the selections could be important because they represent conserved epitopes across these extremely diversified strains. What makes them even more exciting as possible immunological hotspots is that while they are separated by distance in their respective primary amino acid sequence, they near each other according to the folded structure.

Likewise, the HA sequences were derived from multiple sequence alignments of 75 full-length H1 and H3 sequences obtained from the Los Alamos Influenza Sequencing Database and the PubMed database (National Center for Biotechnology Information, National Library of Medicine, National Institutes of Health, Bethesda, Md., USA). FIG. 9 shows the position of the selected epitope on the complete HA molecule.

Example 7

Analysis of Peptide Sequences Across Multiple Viral Isolates

A least two highly conserved peptide regions of influenza A virus hemagglutinin (HA) have been identified through multiple sequence alignment of several thousand strains. Sequences were obtained using the Influenza Virus Resource web site and represent strains obtained from human, avian, and/or mammalian sources.

A primary amino acid multiple sequence alignment was performed using >2,000 H1 and H3 influenza A field strains and representative H5 strains available from the academic and medical literature. H3 and H1 vaccine and reference strains and H5 peptides representing clades 1, 1', 2, and 3 were also included. The 3-D folded A/Wisconsin/67/2005H3N2 vaccine strain was constructed based on the nearest homolog available in the Protein Sequencing Database with the Swiss PDF Viewer. Conserved residues observed in sequence alignments were depicted in the mature HA protein.

Multiple sequence alignments and conserved regions were identified using the software package LaserGene® (DNAStar Inc.). The protein epitope GNLIAP (SEQ ID NO:6), corresponding to H3 amino acid positions 249-254, was completely conserved (100%) in H3 and H1 influenza HA (5,000 of 5,000 queries, including human, swine, and avian sources).

The protein epitope GNFIAP (SEQ ID NO:4) is highly conserved in H5. The GNLIAP (SEQ ID NO:6) region is partially exposed on the distal HA1 surface and is not located within previously proposed antigenic/immunodominant sites (A-E). In addition, YIWGVHHP (SEQ ID NO:52), corresponding to H3 amino acid positions 178-185, was highly conserved (93%) in H3 (7,090 of 7,600 queries, including human, swine, and avian source), and within this region WGVHHP (SEQ ID NO:50) was also highly conserved (86%) on H1 influenza (2,336 of 2,710 queries, including human, swine, and avian sources). The core sequence WGIHHP (SEQ ID NO:49) was also highly conserved (83%) in H5 strains (2049 of 2470 queries, including human and avian strains).

Example 8

Examples of Highly-Conserved Epitopic Sequences Across a Variety of Viral Isolates FIG. 26A, FIG. 26B, and FIG. 26C show examples of highly-conserved epitope sequences across a variety of influenza A subtypes including current and prior vaccine strains. Shown are the consensus sequences (SEQ ID NO:58), (SEQ ID NO:69), and (SEQ ID NO:71) for each of H1 (FIG. 26A), H3 (FIG. 26B) and H5 (FIG. 26C) epitopes, respectively.

These data demonstrate the facility of constructing monomeric and polymeric immunogenic compositions that can be active against a variety of divergent microbial and/or viral species through the selection of conserved epitopic targets.

Example 9

Experimental Methods

The following example summarizes many of the experimental methods used in the aforementioned studies.

Synthetic peptide target antigens were synthesized on 9-fluorenylmethyl chloroformate (Fmoc)-Glu(tBu)-Wang resin utilizing the Fmoc/tBu protection scheme on a CEM Liberty microwave peptide synthesizer. Dimethylformamide (DMF) (ThermoFisher Scientific, Pittsburgh, Pa., USA) was the primary solvent used. The protected amino acids were incorporated into the peptide via active ester formation using o-(benzotriazol-1-yl)-N,N,N',N'-tetramethyluronium tetrafluoroborate (TBTU) (GL Biochem, Ltd. GLS, Shanghai, CHINA) and diisopropylethyl amine (DIEA) (Chem-Impex International, Inc., Wood Dale, Ill., USA) in DMF. All Fmoc protected amino acids were supplied by GL Biochem, Ltd. The side-chain protecting groups used were as follows: Asn, Cys, His, and Gln were protected with trityl (trt); Glu and Ser were protected with tert-butyl (tBu); Lys was protected with tert-butyloxycarbonyl (Boc); Arg was protected with 2,2,4,6,7-pentamethyldihydrobenzofuran-5-sulfonyl (Pbf); and Ala, Leu, Phe, Val, and Gly were used without side-chain protection. The N-terminal Fmoc protecting groups were removed with 20% piperidine (American Bioanalytical, Natick, Mass., USA) in DMF. The peptide was cleaved from the solid support and simultaneously side-chain de-protected using 92% trifluoroacetic acid (Halocarbon Products Corp., River Edge, N.J., USA), 2% anisole, 2% dithiothreitol, 2% triisopropylsilane (Sigma-Aldrich Chemical Co., St. Louis, Mo., USA), and 2% water.

The synthetic peptides described herein were purified on a 600c semi-preparative HPLC system (Waters Corporation, Milford, Mass., USA) using a Vydac® 22 mm×250 mm $C_{18}$ 120 Å column (W.R. Grace and Co., Deerfield, Ill., USA) with solvents: 0.1% TFA/water (A) and 0.1% TFA/acetonitrile (ACN) (B). Peptides were purified in a 35%-50% acetonitrile gradient over 60 min. Analytical HPLC analysis of all fractions was performed using an Alliance 2695 HPLC (Waters Corporation) with a 2.1 mm×30 mm SymmetryShield® RP18 3.5 µm column.

Matrix-assisted laser desorption/ionization time-of-flight (MALDI-ToF) mass spectrometry analysis of the crude and purified peptides was performed using and ABI Voyager® DE Pros system (Applied Biosystems, Foster City, Calif., USA). Crude peptide from each synthesis and pure peptide were dissolved in 50% acetonitrile/water and spotted with α-cyano-4-hydroxycinnamic acid matrix (Sigma-Aldrich). Positive ions were detected using the linear detector, which was calibrated with bradykinin and angiotensin standards.

Preparation of Splenocytes for Cytokine Measurement:

1. For each group of mice to be sacrificed, prepare one sterile 50-mL conical tube with 30 mL of DMEM, EMEM or HBSS containing 1× Pen-Strep. Keep the conical tubes on ice.

2. Sacrifice four mice (i.e., one group) by asphyxiation with $CO_2$.

3. For each mouse, soak the skin with 70% EtOH, and pin to mouse to a dissecting board.

4. Bleed each mouse by cardiac puncture to minimize RBCs in final preparation.

5. Dissect and carefully remove the spleen and transfer it to a 50-mL conical tube.

6. Return all conical tubes to ice.

7. Transfer the spleens and medium to a cell sieve in a sterile, 100-mm Petri dish.

8. Using a cell sieve and the plunger from a 5-mL syringe, gently massage the spleens through the cell sieve until only the capsule remains.

9. Transfer the cell suspension to a new 50-mL conical tube through a Falcon cell strainer and pellet the cells by centrifugation at 1000×g for 10 min. at 4° C.

10. Remove the supernatant and lyse the red blood cells by addition of 1 mL of RBC Lysing solution (Sigma Chemical) for 60-75 sec. Gently rotate the tube to expose all of the RBCs to the lysing buffer.

11. Quickly add 40 mL of EMEM or HBSS with 1× Pen-Strep to the tube.

12. Take a sample of cells for counting. Use a dilution of 1:200 for counting.

13. Pellet the cells by centrifugation as above.

14. Count cells during centrifugation.

15. Following centrifugation, discard supernatant and suspend the cells to a concentration of $2\times10^6$ cells/ml in DMEM with 10% FBS and 1× Pen-Strep.

16. Plant 4 mL of cell suspension per well into each well of a 6-well culture dish (=$10\times10^6$ cells per well).

16. Treat the cells by addition of 1 mL of appropriate peptide at 100, 50, 25 µg/ml of peptide into the 4 mL already in the plate, resulting in final concentrations of the peptide of 20, 10 and 5 µg/mL. One well receives 900 µl of serum-free DMEM and 100 µL of Wuhan 359/95 and one well receives 100 µL of 100 µg/mL of Pn14 polysaccharide and one well receives 1 mL of serum-free DMEM alone.

17. Seventy-two hours after treatment, transfer the supernatants from each well to a 15-mL sterile conical tube.

18. Pellet the cells by centrifugation at 1000×g at 4° C.

19. Transfer 400 to 600 µl of supernatant into each of 6 microtubes and store the samples at −20° C. or below.

21. Keep samples frozen until they are evaluated for IL-4 and IFN-γ or other cytokines.

ELISA for Anti-Peptide Antibodies

Individual sera were tested at a final dilution of 1:100 (in PBS-T) on Nunc Maxisorp® plates coated with the peptide corresponding to the peptide-BSA conjugate used for injection, at a concentration of 1 µg/ml in PBS (100 µl/well). One hundred microliters of diluted sera were reacted on the coated plate for 30 to 60 min at room temperature, and unbound material was removed by washing three times with PBS-T. Anti-peptide antibodies were detected with peroxidase-labeled goat anti-mouse IgG (γ-specific), diluted 1:10000 in PBS-T (100 µl/well; Jackson ImmunoResearch Laboratories, Inc., West Grove, Pa., USA). Following 30-min incubation, the wells were washed five times with PBS-T to removed unbound material and 100 µl of substrate (TMB; Kirkegaard & Perry Laboratories, Inc., Gaithersburg, Md., USA) was added to each well. The reaction was allowed to proceed for 15 min in the dark and stopped by addition of 100 µl of TMB Stop Solution per well (Kirkegaard & Perry). Absorbance was determined at 450 nm.

ELISA for Anti-Wuhan Antibodies

Individual sera from day 0 and day 42 were tested at a final dilution of 1:100 (in PBS-T) on Nunc Maxisorp® plates coated with live Wuhan at a dilution of 1:500 in PBS (100 µl/well). The diluted sera were reacted on the coated plate for 30 to 60 min at room temperature, and unbound material was removed by washing three times with PBS-T. Anti-Wuhan antibodies were detected with peroxidase-labeled goat anti-mouse IgG (γ-specific), diluted 1:10000 in PBS-T (Jackson ImmunoResearch). Following 30 min incubation, the wells were washed five times with PBS-T to removed unbound material and substrate (TMB; Kirkegaard & Perry) was added. The reaction was allowed to proceed for 15 min in the dark, and stopped by addition of TMB Stop Solution (Kirkegaard & Perry). Absorbance was determined at 450 nm.

ELISA for IL-4 and IFN-γ

Assays for IL-4 (DuoSet®kit, R&D Systems, Inc., Minneapolis, Minn., USA) and IFN-γ (BioSource CytoSet® kit; Invitrogen Corp.) were performed on supernatants from pooled spleen cell cultures prepared from mice on experimental day 42. The pooled cultures were treated for 72 hours with the appropriate peptide at 20, 10, 5 or 2.5 µg/ml or Wuhan 0307 359/95 (1:50), or untreated.

IFN-γ Assay

1. Prepare coating solution by diluting the coating antibody.

2. Coat plates with 100 µL per well of the coating solution. Cover plates and incubate overnight (12-18 hr.) at 4° C.

3. Aspirate wells and wash once with >400 µL of Wash Buffer per well. Following wash, invert and tap on absorbent paper to remove excess liquid.

4. Block plate with 300 µL per well of Assay Buffer for 1 hour at room temperature.

5. Aspirate, invert, and tap on absorbent paper to remove excess liquid.

6. Prepare standards and sample dilutions in Assay Buffer.

7. Pipette 100 µL of standards (in duplicate), samples and controls into designated wells.

8. Immediately following step 7, add 50 µL of the working detection antibody into each well. Cover plate and incubate for 2 hours at room temperature.

9. Aspirate and wash 5 times using the method in step 3.

10. Add 100 µL of the working streptavidin-HRP solution into each well. Cover plate and incubate for 30 min. at room temperature.

11. Aspirate and wash 5 times using the method in step 3.

12. Add 100 µL of the TMB substrate to each well. Incubate plate without a plate cover for 30 min in the dark at room temperature.

13. Add 100 µL of Stop Solution to each well.

14. Measure absorbance at 450 nm (reference absorbance: 650 nm) within 30 min. of adding Stop Solution. Calculate results using a log-log or 4-parameter curve fit.

Reagents and Viral Stocks

PF2001-Pn14 conjugates and the Pn14 polysaccharide were provided by Fina BioSolutions, LLC (Rockville, Md., USA). Influenza A/Wuhan/359/95 was provided by Virion Systems, Inc. (Rockville, Md., USA). The virus stock was originally prepared by NovaVax from MDCK cells. The stocks were stored at −80° C. and had a titer of $10^8$ TCID$_{50}$ per mL.

All assays were performed according to manufacturers' instructions.

Exemplary Peptide Antigen Sequences of the Invention

The following is a non-limiting list of exemplary peptide epitopes that may be used in the practice of the present invention, and in particular, in the formulation of polyvalent antigenic peptides and polypeptides:

| | |
|---|---|
| DWSGYSGSFVQHPELTGLD | (SEQ ID NO: 1) |
| ETPIRNE | (SEQ ID NO: 2) |
| FVIREPFISCSHLEC | (SEQ ID NO: 3) |
| GNFIAP | (SEQ ID NO: 4) |
| GNLFIAP<br>(also referred to herein as "Peptide 5910") | (SEQ ID NO: 5) |
| GNLIAP | (SEQ ID NO: 6) |
| HYEECSCY<br>(also referred to herein as "Peptide 5911") | (SEQ ID NO: 7) |
| LLTEVETPIR | (SEQ ID NO: 8) |
| LLTEVETPIRN | (SEQ ID NO: 9) |
| LLTEVETPIRNE | (SEQ ID NO: 10) |
| DWSGYSGSFVQHPELTGL<br>(also referred to herein as "Peptide 5912") | (SEQ ID NO: 11) |
| EVETPIRNE | (SEQ ID NO: 12) |
| FLLPEDETPIRNEWGLLTDDETPIRYIKANSKFIGITE | (SEQ ID NO: 13) |
| GNLFIAPGNLFIAPHYEECSCYHYEECSCYQYIKANSKFIGITEHYEECSCYTPIRNETPIRNE | (SEQ ID NO: 14) |
| GNLFIAPGNLFIAPQYIKANSKFIGITEGNLFIAP<br>(also referred to herein as "Peptide 5907") | (SEQ ID NO: 15) |
| HYEECSCYDWSGYSGSFVQHPELTGLHYEECSCYQYIKANSKFIGITE<br>(also referred to herein as "Peptide 5908") | (SEQ ID NO: 16) |
| ITGFAPFSKDNSIRLSAGGDIWVTREPYVSCDP<br>(also referred to herein as "Peptide 5913") | (SEQ ID NO: 17) |
| IWGIHHP | (SEQ ID NO: 18) |
| IWGVHHP | (SEQ ID NO: 19) |
| KSCINRCFYVELIRGR<br>(also referred to herein as "Peptide 5914") | (SEQ ID NO: 20) |
| LLTEVETPIRNESLLTEVETPIRNEWG | (SEQ ID NO: 21) |
| LLTEVETPIRNEW | (SEQ ID NO: 22) |
| LLTEVETPIRNEWG | (SEQ ID NO: 23) |
| LTEVETPIRNE | (SEQ ID NO: 24) |
| LTEVETPIRNEW | (SEQ ID NO: 25) |
| LTEVETPIRNEWG | (SEQ ID NO: 26) |
| MSLLTEVET | (SEQ ID NO: 27) |
| MSLLTEVETP | (SEQ ID NO: 28) |
| MSLLTEVETPI | (SEQ ID NO: 29) |
| MSLLTEVETPIR | (SEQ ID NO: 30) |
| MSLLTEVETPIRN | (SEQ ID NO: 31) |
| MSLLTEVETPIRNE | (SEQ ID NO: 32) |
| MSLLTEVETPIRNETPIRNE | (SEQ ID NO: 33) |
| MSLLTEVETPIRNEW | (SEQ ID NO: 34) |
| MSLLTEVETPIRNEWG | (SEQ ID NO: 35) |
| MSLLTEVETPIRNEWGCRGNDSSD | (SEQ ID NO: 36) |
| SLLTEVET | (SEQ ID NO: 37) |

-continued

| | |
|---|---|
| SLLTEVETPIRNE | (SEQ ID NO: 38) |
| SLLTEVETPIRNEW | (SEQ ID NO: 39) |
| SLLTEVETPIRNEWG | (SEQ ID NO: 40) |
| SLLTEVETPIRNEWGTPIRNE | (SEQ ID NO: 41) |
| SLLTEVETPIRNEWGTPIRNETPIRNE | (SEQ ID NO: 42) |
| SLLTEVETPIRNEWGTPIRNETPIRNETPIRNE | (SEQ ID NO: 43) |
| SLLTEVETPIRNEWGLLTEVETPIRQYIKANSKLFIGITE<br>(also referred to herein alternatively as "PF2001" or "Peptide 5906") | (SEQ ID NO: 44) |
| TEVETPIRNE | (SEQ ID NO: 45) |
| TPIRNE | (SEQ ID NO: 46) |
| VETPIRNE | (SEQ ID NO: 47) |
| VTREPYVSCDPKSCINRCFYVELIRGRVTREPYVSCDPWYIKANSKFIGITE<br>(also referred to herein as "Peptide 5909") | (SEQ ID NO: 48) |
| WGIHHP | (SEQ ID NO: 49) |
| WGVHHP | (SEQ ID NO: 50) |
| YIWGIHHP | (SEQ ID NO: 51) |
| YIWGVHHP | (SEQ ID NO: 52) |
| QYIKANSKFIGITE | (SEQ ID NO: 53) |
| PIRNEWGCRCNDSSD | (SEQ ID NO: 54) |
| SIELE | (SEQ ID NO: 55) |
| MSLLTEVETYVLSIVP | (SEQ ID NO: 56) |
| MQRFK | (SEQ ID NO: 57) |
| NGNLIAPRYAFALSRGFGFGIITSNAPMDE | (SEQ ID NO: 58) |
| NGNLIAPRYAFALSRGFGFGIINSNAPMDK | (SEQ ID NO: 59) |
| NGNLIAPRYAFALSRGFGSGIINSNAPMDK | (SEQ ID NO: 60) |
| NGNLIAPRYAFALSRGFGSGIINSNAPMDK | (SEQ ID NO: 61) |
| NGNLIAPWYAFALSRGFGSGIITSNASMGE | (SEQ ID NO: 62) |
| NGNLIAPWYAFALSRGFGSGIITSNAPMNE | (SEQ ID NO: 63) |
| NGNLIAPRYAFALSRGFGSGIINSNAPMDE | (SEQ ID NO: 64) |
| NGNLIAPWYAFALSRGFGSGIITSNAPMDE | (SEQ ID NO: 65) |
| NGNLIAPRYAFALSRGFGSGIITSNAPMDE | (SEQ ID NO: 66) |
| NGNLIAPWYAFALSRGFGSGIITSNAPMDE | (SEQ ID NO: 67) |
| NGNLIAPWYAFALSRGFGSGIITSNSPMDE | (SEQ ID NO: 68) |
| NSTGNLIAPRGYFKIRSGKSSIMRSDAPIGKCN | (SEQ ID NO: 69) |
| NSTGNLIAPRGYFKIRSGKSSIMRSDAPIGKCK | (SEQ ID NO: 70) |
| DAINFESNGNFIAPEYAYKIVKKGDSTIMKSEL | (SEQ ID NO: 71) |
| DAINFESNGNFIAPEYAYKIVKKGDSAIMKSEV | (SEQ ID NO: 72) |
| DAINFESNGNFIAPENAYKIVKKGDSTIMKSEL | (SEQ ID NO: 73) |
| DAINFESNGNFIAPEYAYKIVKKGDSTIMKSEL | (SEQ ID NO: 74) |
| DAINFESNGNFIAPEYAYKIVKKGDSAIMKSEL | (SEQ ID NO: 75) |

REFERENCES

The following references, to the extent that they provide exemplary procedural or other details supplementary to those set forth herein, are specifically incorporated herein in their entirety by express reference thereto:

U.S. Pat. No. 7,357,936, entitled "Adjuvant systems and vaccines."
U.S. Pat. No. 7,223,409, entitled "DNA-based vaccine against the encephalitis alphaviruses."
U.S. Pat. No. 7,090,853, entitled "Noscapine derivatives as adjuvant compositions and methods of use thereof."
U.S. Pat. No. 6,793,928, entitled "Vaccines with an LTB adjuvant."
U.S. Pat. No. 6,780,421, entitled "Adjuvant for a vaccine composition."
U.S. Pat. No. 6,759,241, entitled "Adjuvant comprising a lipopolysaccharide antagonist."
U.S. Pat. No. 6,713,068, entitled "Live recombined vaccines injected with adjuvant."
U.S. Pat. No. 6,603,998, entitled "Delivery of macromolecules into cells."
U.S. Pat. No. 6,572,866, entitled "Nerve growth factor as a vaccine adjuvant."
U.S. Pat. No. 6,534,065, entitled "Influenza vaccine composition with chitosan adjuvant."
U.S. Pat. No. 6,500,432, entitled "Method to enhance an immune response of nucleic acid vaccination."
U.S. Pat. No. 6,451,325, entitled "Adjuvant formulation comprising a submicron oil droplet emulsion."
U.S. Pat. No. 6,440,423, entitled "Mutant enterotoxin effective as a non-toxic oral adjuvant."
U.S. Pat. No. 6,306,404, entitled "Adjuvant and vaccine compositions containing monophosphoryl lipid A."
U.S. Pat. No. 6,060,068, entitled "Human IL-2 as a vaccine adjuvant."
U.S. Pat. No. 6,033,673, entitled "Double mutant enterotoxin for use as an adjuvant."
U.S. Pat. No. 5,800,810, entitled "Human IL-2 as a vaccine adjuvant."
U.S. Pat. No. 5,795,582, entitled "Adjuvant properties of poly(amidoamine) dendrimers."
U.S. Pat. No. 5,785,975, entitled "Adjuvant compositions and vaccine formulations comprising same."
U.S. Pat. No. 5,679,356, entitled "Use of GM-CSF as a vaccine adjuvant."
U.S. Pat. No. 5,641,515, entitled "Controlled release biodegradable nanoparticles containing insulin."
U.S. Pat. No. 5,543,158, entitled "Biodegradable injectable nanoparticles."
U.S. Pat. No. 5,503,841, entitled "Human IL-2 as a vaccine adjuvant."
U.S. Pat. No. 5,399,363, entitled "Surface modified anticancer nanoparticles."
U.S. Pat. No. 5,186,898, entitled "Automated polypeptide synthesis apparatus."
U.S. Pat. No. 5,182,109, entitled "Vaccine preparation comprising a bacterial toxin adjuvant."
U.S. Pat. No. 4,816,513, entitled "Automated polypeptide synthesis process."
U.S. Pat. No. 4,746,490, entitled "Solid phase peptide synthesizer."
U.S. Pat. No. 4,668,476, entitled "Automated polypeptide synthesis apparatus."
U.S. Pat. No. 4,608,251, entitled "LHRH analogues useful in stimulating anti-LHRH antibodies and vaccines containing such analogues."
U.S. Pat. No. 4,601,903, entitled "Vaccine against *Neisseria meningitidis* Group B serotype 2 invasive disease."
U.S. Pat. No. 4,599,231, entitled "Synthetic hepatitis B virus vaccine including both T cell and B cell determinants."
U.S. Pat. No. 4,596,792, entitled "Safe vaccine for hepatitis containing polymerized serum albumin."
U.S. Pat. No. 4,474,757, entitled "Synthetic vaccine and process for producing same."
U.S. Pat. No. 4,372,945, entitled "Antigen compounds."
U.S. Pat. No. 4,356,170, entitled "Immunogenic polysaccharide-protein conjugates."
U.S. Patent Appl. Publ. No. 2008/0181914, entitled "Novel vaccine composition."
U.S. Patent Appl. Publ. No. 2008/0181905, entitled "Nanoemulsion vaccines."
U.S. Patent Appl. Publ. No. 2008/0145373, entitled "A-beta immunogenic peptide carrier conjugates and methods of producing same."
U.S. Patent Appl. Publ. No. 2008/0118531, entitled "Avian influenza viruses, vaccines, compositions, formulations, and methods."
U.S. Patent Appl. Publ. No. 2008/0107687, entitled "Feline vaccines against avian influenza."
U.S. Patent Appl. Publ. No. 2008/0107665, entitled "Extracellular matrix materials as vaccine adjuvants for diseases associated with infectious pathogens or toxins."
U.S. Patent Appl. Publ. No. 2008/0075708, entitled "Broad spectrum anti-viral therapeutics and prophylaxis."
U.S. Patent Appl. Publ. No. 2008/0069821, entitled "Influenza hemagglutinin and neuraminidase variants."
U.S. Patent Appl. Publ. No. 2008/0032921, entitled "Inducing immune responses to influenza virus using polypeptide and nucleic acid compositions."
U.S. Patent Appl. Publ. No. 2005/0169941, entitled "Use of amino-oxy functional groups in the preparation of protein-polysaccharide conjugate vaccines."
U.S. Patent Appl. Publ. No. 2004/0223976, entitled "Influenza virus vaccine."
PCT Intl. Pat. Appl. Publ. No. WO95/08348.
PCT Intl. Pat. Appl. Publ. No. WO 2003/53462.
PCT Intl. Pat. Appl. Publ. No. WO 2004/43407.
Altschul et al., *J. Mol. Biol.*, 215:403-410, 1990.
Conley et al., *Vaccine* 12:445-451, 1994.
Feng and Doolittle, *J. Mol. Evol.*, 35:351-360, 1987.
Henikoff and Henikoff, *Proc. Natl. Acad. Sci. USA*, 89:10915, 1989.
Higgins and Sharp, *Comput. Appl. Biosci.*, 5:151-153, 1989.
Karlin and Altschul, *Proc. Natl. Acad. Sci. USA*, 90:5873-5787, 1993.
Kohler and Milstein, *Nature*, 256:495-497, 1975.
Lou, M., *Nature*, 443:37-38, September 2006.
Needleman and Wunsch, *J. Mol. Biol.*, 48:443, 1970.
Pearson and Lipman, *Proc. Natl. Acad. Sci. USA*, 85:2444, 1988.
Smith and Waterman, *Adv. Appl. Math.*, 2:482, 1981.
Tolman et al., *Int. J. Pep. Prot. Res.*, 41:455-466, 1993.

All of the compositions and methods disclosed and claimed herein can be made and executed without undue experimentation in light of the present disclosure. While the compositions and methods of this invention have been described in terms of exemplary embodiments, it will be apparent to those of ordinary skill in the art that variations may be applied to the composition, methods and in the steps or in the sequence of steps of the method described herein without departing from the concept, spirit and scope of the invention. More specifically, it will be apparent that certain agents that are both chemically- and physiologically-related may be substituted for the agents described herein while the same or similar results would be achieved. All such similar substitutes and modifications apparent to those of ordinary skill in the art are deemed to be within the spirit, scope and concept of the invention as defined by the appended claims. Accordingly, the exclusive rights sought to be patented are as described in the claims below.

What is claimed is:

1. An immunogenic fusion peptide or polypeptide comprising:
   (a) at least two antigenic peptide epitopes each of 7 to about 70 amino acids in length wherein either comprises the amino acid sequence of any one of SEQ ID NO: 5, SEQ ID NO: 14, SEQ ID NO: 15, SEQ ID NO: 16, and SEQ ID NO: 44, and
   (b) at least one epitope of a tetanus toxoid, a diphtheria toxoid, a polysaccharide, a lipoprotein, or any combination thereof, wherein said at least one epitope is a T-cell stimulating epitope.

2. The immunogenic fusion peptide or polypeptide of claim 1, further comprising an amino acid sequence that is at least 95% identical to the sequence of any one of SEQ ID NO:1 to SEQ ID NO:52.

3. The immunogenic fusion peptide or polypeptide of claim 1, further comprising an amino acid sequence that is at least 98% identical to the sequence of any one of SEQ ID NO:1 to SEQ ID NO:52.

4. The immunogenic fusion peptide or polypeptide of claim 3, further comprising the amino acid sequence of any one of SEQ ID NO:1 to SEQ ID NO:52.

5. The immunogenic fusion peptide or polypeptide of claim 1, further comprising the amino acid sequence of any one of SEQ ID NO:5, SEQ ID NO:7, SEQ ID NO:11, SEQ ID NO:15, SEQ ID NO:16, SEQ ID NO:20, SEQ ID NO:44 or SEQ ID NO:48.

6. An immunogenic fusion peptide or polypeptide comprising:
   (a) at least two antigenic peptide epitopes, each of 7 to about 70 amino acids in length, wherein either comprises the amino acid sequence of any one of SEQ ID NO: 5, SEQ ID NO: 14, SEQ ID NO: 15, SEQ ID NO: 16 and SEQ ID NO: 44; and
   (b) a T-cell stimulating epitope comprising an amino acid sequence that is at least 90% identical to the amino acid sequence of SEQ ID NO: 53.

7. An isolated polynucleotide that encodes the immunogenic fusion peptide or polypeptide of claim 1.

8. An expression vector that comprises the isolated polynucleotide of claim 7.

9. The expression vector of claim 8, wherein the polynucleotide is operably linked to a promoter effective to produce at least a first antigenic peptide from the polynucleotide in a mammalian host cell that expresses the vector.

10. A reassortant, killed, or inactivated viral vector comprising a polynucleotide that encodes the immunogenic fusion peptide or polypeptide of claim 1.

11. A recombinant influenza virus comprising a polynucleotide that encodes the immunogenic fusion peptide or polypeptide of claim 1.

12. A live attenuated recombinant influenza virus comprising a polynucleotide that encodes the immunogenic fusion peptide or polypeptide of claim 1.

13. The immunogenic fusion peptide or polypeptide of claim 1, formulated for administration to an animal host cell.

14. The immunogenic fusion peptide or polypeptide of claim 1, formulated for administration to a mammalian host cell.

15. The immunogenic fusion peptide or polypeptide of claim 1, formulated for systemic or local administration to a human.

16. The immunogenic fusion peptide or polypeptide of claim 1, formulated for intradermal, intramuscular, intranasal, intravenous, oral, parenteral, subcutaneous, transcutaneous, or transdermal administration.

17. The immunogenic fusion peptide or polypeptide of claim 1, further comprising an adjuvant.

18. The immunogenic fusion peptide or polypeptide of claim 1, further comprising an ethosome, a lipid complex formed from at least one different lipid, a liposome, a niosome, a phospholipid, a sphingosome, a surfactant, a transferosome, or any combination thereof.

19. The immunogenic fusion peptide or polypeptide of claim 1, comprised within a microcapsule, microparticle, microsphere, nanocapsule, nanoparticle, nanosphere, or a combination thereof.

20. A method of eliciting an immunological response to an influenzavirus in an animal, comprising administering the immunogenic fusion peptide or polypeptide of claim 1 in an effective amount for eliciting the immunological response to the influenza virus in the animal.

21. A method of producing an immune response in a mammal, the method comprising administering the immunogenic fusion peptide or polypeptide of claim 1 in an amount effective to produce an immune response in the mammal.

22. An immunogenic fusion peptide or polypeptide comprising:

the amino acid sequence of any one of SEQ ID NO: 5, SEQ ID NO: 14, SEQ ID NO: 15, SEQ ID NO: 16, and SEQ ID NO: 44; and at least one epitope of a tetanus toxoid, a diphtheria toxoid, a polysaccharide, a lipoprotein, or any combination thereof, wherein the at least one epitope is a T-cell stimulating epitope.

23. The immunogenic fusion peptide or polypeptide of claim 1, wherein at least two of the antigenic epitopes are repeated and either multimeric, collinearly expressed, or chemically crosslinked.

24. The immunogenic fusion peptide or polypeptide of claim 1, wherein at least one antigenic peptide epitope is specific for an influenza virus HA, H1, H3, H5, NA, M1, or M2 protein.

25. The immunogenic fusion peptide or polypeptide of claim 1, wherein at least one antigenic peptide epitope is specific for H1N1, H3N2, H2N2 or H5N1 strain of influenza virus A.

26. The immunogenic fusion peptide or polypeptide of claim 1, conjugated to a type 14 pneumococcal polysaccharide.

27. The immunogenic fusion peptide or polypeptide of claim 1, comprising at least a first epitope specific for a *Streptococcus* or a *Staphylococcus* protein.

28. An immunogenic fusion peptide or polypeptide comprising:
   (a) an antigenic peptide epitope comprising the amino acid sequence of any one of SEQ ID NO: 5, SEQ ID NO: 14, SEQ ID NO: 15, SEQ ID NO: 16 and SEQ ID NO: 44 and
   (b) a T-cell stimulating epitope comprising an amino acid sequence that is at least 90% identical to the amino acid sequence of SEQ ID NO: 53.

29. A therapeutic or diagnostic kit in a suitable container, which kit comprises:

A) a composition comprising:
   (i) an immunogenic fusion peptide or polypeptide, comprising the amino acid sequence of SEQ ID NO: 5, SEQ ID NO: 14, SEQ ID NO: 15, SEQ ID NO: 16 and SEQ ID NO: 44: and an epitope derived from at least one of a tetanus toxoid, a diphtheria toxoid, a polysaccharide, a lipoprotein, or any combination thereof, wherein said epitope is a T-cell stimulating epitope;
   (ii) an isolated polynucleotide encoding the immunogenic fusion peptide or polypeptide;
   (iii) an expression vector or a reassortant, killed, attenuated, or inactivated virus, or viral vector comprising the polynucleotide;
   (iv) an antibody or antigen binding fragment that specifically binds to the immunogenic fusion peptide or polypeptide; or
   (v) any combination thereof; and
B) instructions for administering the composition to a mammal in need thereof.

30. A peptide comprising the sequence of SEQ ID NO 14.
31. A peptide comprising the sequence of SEQ ID NO 15.
32. A peptide comprising the sequence of SEQ ID NO 16.
33. A peptide comprising the sequence of SEQ ID NO 44.

* * * * *